(12) United States Patent
Hirvelä et al.

(10) Patent No.: US 9,850,272 B2
(45) Date of Patent: Dec. 26, 2017

(54) THERAPEUTICALLY ACTIVE ESTRATRIENTHIAZOLE DERIVATIVES AS INHIBITORS OF 17.BETA-HYDROXY-STEROID DEHYDROGENASE, TYPE 1

(71) Applicant: FORENDO PHARMA LTD, Turku (FI)

(72) Inventors: Leena Hirvelä, Oulu (FI); Lauri Kangas, Lieto (FI); Pasi Koskimies, Turku (FI); Risto Lammintausta, Turku (FI); Mikko Unkila, Piikkiö (FI)

(73) Assignee: FORENDO PHARMA LTD., Turku (FI)

( * ) Notice: Subject to any disclaimer, the term of this patent is extended or adjusted under 35 U.S.C. 154(b) by 0 days.

(21) Appl. No.: 14/392,290

(22) PCT Filed: Jun. 25, 2014

(86) PCT No.: PCT/FI2014/050519
§ 371 (c)(1),
(2) Date: Dec. 23, 2015

(87) PCT Pub. No.: WO2014/207311
PCT Pub. Date: Dec. 31, 2014

(65) Prior Publication Data
US 2017/0081356 A1    Mar. 23, 2017

(30) Foreign Application Priority Data
Jun. 25, 2013   (FI) .................................... 20135695

(51) Int. Cl.
*C07J 51/00*   (2006.01)
*C07J 43/00*   (2006.01)

(52) U.S. Cl.
CPC ............. *C07J 43/003* (2013.01); *C07J 51/00* (2013.01)

(58) Field of Classification Search
None
See application file for complete search history.

(56) References Cited

U.S. PATENT DOCUMENTS 8,030,298 B2 * 10/2011 Messinger ............... C07J 43/00
                                                              514/176
2006/0281710 A1   12/2006 Messinger et al.
2008/0255075 A1   10/2008 Messinger et al.

FOREIGN PATENT DOCUMENTS

| WO | WO 99/046279 | 9/1999 |
|---|---|---|
| WO | WO 01/042181 | 6/2001 |
| WO | WO 03/022835 | 3/2003 |
| WO | WO 03/033487 | 4/2003 |
| WO | WO 04/046111 | 6/2004 |
| WO | WO 04/060488 | 7/2004 |
| WO | WO 04/085345 | 10/2004 |
| WO | WO 04/085457 | 10/2004 |
| WO | WO 04/110459 | 12/2004 |
| WO | WO 05/032527 | 4/2005 |
| WO | WO 05/047303 | 5/2005 |
| WO | WO 05/084295 | 9/2005 |
| WO | WO 06/003012 | 1/2006 |
| WO | WO 06/003013 | 1/2006 |
| WO | WO 06/027347 | 3/2006 |
| WO | WO 06/125800 | 11/2006 |
| WO | WO 08/034796 | 3/2008 |
| WO | WO 08/065100 | 6/2008 |
| WO | WO 12/129673 | 10/2012 |

OTHER PUBLICATIONS

Koffman et al., "Evidence for Involvement of Tyrosine in Estradiol Binding by Rat Uterus Estrogen Receptor", *J. Steroid Biochem. Molec. Biol.*, vol. 38, No. 2, pp. 135-139, 1991.

Messinger et al., "Estrone C15 derivatives—A new class of 17β-hydroxysteroid dehydrogenase type 1 inhibitors", *Molecular and Cellular Endocrinology*, vol. 301, pp. 216-224, (2009).

Moller et al., "Structure-based design, synthesis and in vitro characterization of potent 17β-hydroxysteroid dehydrogenase type 1 inhibitors based on 2-substitutions of estrone and D-homo-estrone", *Bioorganic & Medicinal Chemistry Letters*, vol. 19, pp. 6740-6744, (2009).

(Continued)

*Primary Examiner* — Kamal Saeed
(74) *Attorney, Agent, or Firm* — Brinks Gilson & Lione

(57) ABSTRACT

The invention relates to compounds of formula (I) and pharmaceutically acceptable salts thereof wherein R2, R3, R4, R7 and R8 are as defined in the claims. The invention further relates to their use as inhibitors of 17β-HSD1 and in treatment or prevention of steroid hormone dependent diseases or disorders, such as steroid hormone dependent diseases or disorders requiring the inhibition of the 17β-HSD1 enzyme and/or requiring the lowering of the endogenous estradiol concentration. The present invention also relates to the preparation of the aforementioned compounds and to pharmaceutical compositions comprising as an active ingredient(s) one or more of the aforementioned compounds or pharmaceutically acceptable salts thereof.

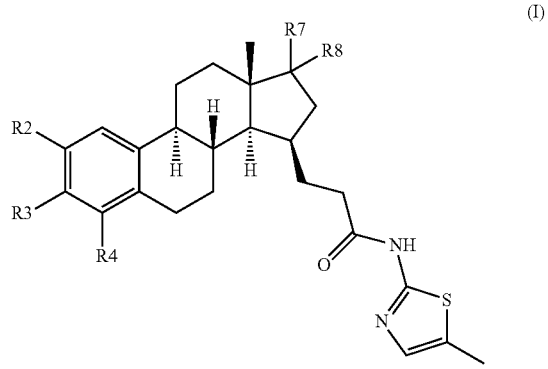

20 Claims, No Drawings

(56) References Cited

OTHER PUBLICATIONS

Möller et al., "Species Used for Drug Testing Reveal Different Inhibition Susceptibility for 17 beta-Hydroxysteroid Dehydrogenase Type 1", *PLoS ONE*, vol. 5, Issue 6, pp. 1-11; (Jun. 2010).

Poirier, Donald, "Inhibitors of 17β-Hydroxysteroid Dehydrogenases", *Current Medicinal Chemistry*, vol. 10, No. 6; pp. 453-477; (2003).

Poirier, Donald, "17β-Hydroxysteroid dehydrogenase inhibitors: a patent review", *Expert Opin. Ther. Patents*, 20(9), pp. 1123-1145; (2010).

Puranen et al., "Site-directed mutagenesis of the putative active site of human 17β-hydroxysteroid dehydrogenase type 1", *Biochem. J.*, 304; pp. 289-293; (1994).

Sam et al., "C16 and C17 Derivatives of Estradiol as Inhibitors of 17β—Hydroxysteroid Dehydrogenase Type 1: Chemical Synthesis and Structure-Activity Relationships", Drug Design and Discovery, vol. 15, pp. 157-180, (1998).

International Search Report and Written Opinion of PCT/FI2014/050519, dated Aug. 25, 2014.

Search Report for Finnish Patent Application No. 20135695, dated Feb. 12, 2014.

\* cited by examiner

THERAPEUTICALLY ACTIVE ESTRATRIENTHIAZOLE DERIVATIVES AS INHIBITORS OF 17.BETA-HYDROXY-STEROID DEHYDROGENASE, TYPE 1

FIELD OF THE INVENTION

The present invention relates to novel estradiol C-15 thiazole derivatives, to their pharmaceutically acceptable salts, and their use in therapy. The invention further relates to pharmaceutical compositions comprising these compounds as active ingredients and to methods for their preparation.

BACKGROUND OF THE INVENTION

17β-hydroxysteroid dehydrogenases (17β-HSDs), also known as 17-ketosteroid reductases (17-KSR) are NAD(H)- and/or NAPD(H)-dependent alcohol oxidoreductase enzymes which catalyse the last and key step in formation of all estrogens and androgens. More specifically 17β-HSDs catalyse the dehydrogenation (oxidation) of 17-hydroxysteroids into corresponding 17-ketosteroids or hydrogenation (reduction) of inactive 17-ketosteroids into corresponding active 17-hydroxysteroids.

As both estrogens and androgens have the highest affinity for their receptors in the 17β-hydroxy form, the 17β-HSD/KSRs regulate the biological activity of the sex hormones. At present, 15 human members of 17β-HSDs have been described (type 1-15). Different types of 17β-HSD/KSRs differ in their substrate and cofactor specificities. The 17KSR activities convert low-activity precursors to more potent forms while 17β-HSD activities decrease the potency of estrogens and androgens and consequently may protect tissues from excessive hormone action.

Each type of 17β-HSD has a selective substrate affinity and a distinctive, although in some cases overlapping, tissue distribution.

Type 1 17β-hydroxysteroid dehydrogenase (17β-HSD1) is most abundantly expressed in the ovarian granulosa cells of the developing follicles in ovaries and in human placenta, both being estrogen biosynthetic tissues. In addition 17β-HSD1 is expressed in estrogen target tissues, including breast, endometrium and bone. The human 17β-HSD1 is specific to estrogenic substrates and in vivo catalyzes the reduction of estrone to estradiol.

Type 2 17β-hydroxysteroid dehydrogenase (17β-HSD2) on the other hand converts estradiol, testosterone and 5a-dihydrotestrosterone to their less active forms estrone, androstenedione and 5a-androstanedione, respectively. Due to its wide and abundant expression in number of various estrogen and androgen target tissues, such as uterus, placenta, liver and the gastrointestinal and urinary tracts, it has been suggested that type 2 enzyme protects tissues from excessive steroid actions.

Estradiol (E2) is about 10 times as potent as estrone (E1) and about 80 times as potent as estratriol (E3) in its estrogenic effect. In contrast to certain other estrogens, estradiol binds well to both estrogen receptors ERα and ERβ, and thus regulates the expression of a variety of genes.

Although both 17β-HSD1 and 17β-HSD2 are present in healthy pre-menopausal humans, increased ratio of 17β-HSD1 to 17-HSD2 in the tumors of postmenopausal patients with hormone-dependent breast cancer has been shown in several studies. 17HSD1 gene amplification and loss of heterozygosity of 17HSD2 allele are potential mechanisms involved to increased reductive estrogen synthesis pathway in breast tumors. Increased ratio of type 1 enzyme to type 2 enzyme results in an increased level of estradiol that then promotes the proliferation of the cancerous tissue via the estrogen receptors (ER). High levels of estrogen thus support certain cancers such as breast cancer and cancer of the uterine lining i.e. endometrial cancer and uterine cancer.

Similarly it has been suggested that 17β-HSD2 is down-regulated in endometriosis while both aromatase and 17β-HSD1 are expressed or upregulated in comparison with normal endometrium. This again results in the presence of high concentration of estradiol (E2) which drives the proliferation of the tissue. Similar mechanism has been elucidated in uterine leiomyoma (uterine fibroids) and endometrial hyperplasia.

Reduction of the endogenous estradiol concentration in affected tissues will result in reduced or impaired proliferation of 17β-estradiol cells in said tissues and may thus be utilized in prevention and treatment of malign and benign estradiol dependent pathologies. Due to the proposed involvement of 17β-estradiol in a number of malign and benign pathologies, inhibitors of 17β-hydroxysteroid dehydrogenases, that can be used to impair endogenous production of estradiol from estrone, can have therapeutic value in the prevention or the treatment of such disorders or diseases are in great demand.

Some small-molecule inhibitors of 17β-HSD1 enzyme have been identified and reviewed in Poirier D. (2003) Curr Med Chem 10: 453-77 and Poirier D. (2010) Expert Opin. Ther. Patents 20(9): 1123-1145. Further, small molecule inhibitors of 17β-HSD's have been disclosed in WO 2001/42181, WO 2003/022835, WO 2003/033487, WO 2004/046111, WO 2004/060488, WO 2004/110459, WO 2005/032527, and WO 2005/084295.

WO2004/085457 discloses steroidal compounds capable of inhibiting 17β-hydroxysteroid dehydrogenase. WO2006/003012 discloses 2-substituted D-homo-estriene derivatives suitable for the treatment of estrogen-dependent diseases that can be influenced by the inhibition of the 17β-hydroxysteroid dehydrogenase type 1. Similarly WO2006/003013 presents 2-substituted estratrienones usable for preventing and treating estrogen-dependent diseases influenced by inhibiting 17β-hydroxysteroid dehydrogenase type 1.

15-substituted estradiol analogues acting as locally active estrogens are presented in WO2004/085345. WO2006/027347 discloses 15b-substituted estradiol derivatives having selective estrogenic activity for the treatment or prevention of estrogen receptor-related diseases and physiological conditions. Further, WO2005/047303 discloses 3, 15 substituted estrone derivatives capable of inhibiting the 17β-hydroxysteroid dehydrogenase type 1.

International application WO2008/034796 relates to estratrien triazoles suitable for use in treatment and prevention of steroid hormone dependent diseases or disorders requiring the inhibition of a 17β-hydroxysteroid dehydrogenases such as 17β-HSD type 1, type 2 or type 3 enzyme. Inhibitors of 17β-HSD type 3 enzyme have been disclosed in WO99/46279.

BRIEF DESCRIPTION [DISCLOSURE] OF THE INVENTION

An object of the present invention is to provide compounds useful in treating disorders and diseases associated with increased level of estradiol and/or treatable by inhibition of 17β-HSD1 enzyme. It is further an object of the present invention to provide compounds that show little or no inhibitory effect on 17β-HSD2 enzyme.

One of the problems associated with the known 17β-HSD1 inhibitors is the disposition, in particular the metabolic stability, of the compounds. It is therefore yet a further object of the present invention to provide compounds with improved metabolic stability.

The present invention provides a novel compound of formula (I)

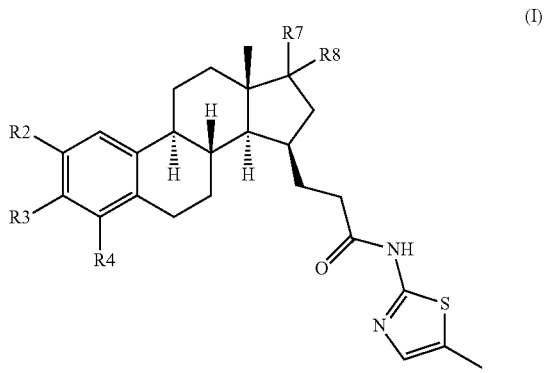

wherein (i-a) R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_nN(R')_2$, OR', $(CH_2)_nOR'$, $CO_2R'$, CONHR', NHCOR'', SCOR', or COR''; and R3 is selected from the group consisting of H, $C_{1-6}$-alkyl, $C_{1-3}$-haloalkyl, $C_{1-3}$-perhaloalkyl, $N(R')_2$, $N_3$, and $OR_3'$, wherein $R_3'$ is selected from the group consisting of R', benzyl, succinyl, optionally acylated glucuronyl, saturated 5 to 6 membered heterocyclic ring comprising 1 or 2 heteroatoms independently selected from N and O, $(CH_2)_nOH$, $SO_2OH$, $SO_2R''$, tosyl, $SO_2N(R')_2$, $PO(OR')_2$, $C(O)N(R')_2$, $C(O)(CH_2)_nN(R')_2$, and C(O)R'''; or (i-b) R2 and R3 or R3 and R4, together with the ring carbon atoms to which they are attached, form an unsaturated or aromatic 5-membered heterocyclic ring comprising 1 or 2 heteroatoms each independently selected from N and O, optionally substituted with methyl or oxo; and R4 or R2, respectively, is H and halogen;

(ii-a) one of R7 and R8 is OR7', wherein R7' is selected from the group consisting of H or $C_{1-6}$-alkyl and the other is selected from the group consisting of H, $C_{1-6}$-alkyl, $C_{1-3}$-haloalkyl, $C_{1-3}$-perhaloalkyl, $C_{2-6}$-alkenyl, $C_{2-6}$-alkynyl, benzyl, $(CH_2)_nCN$, $(CH_2)_nOH$, $N(R')_2$, $(CH_2)_nN(R')_2$, C(O)OR', $(CH_2)_nC(O)OR'$, $C(O)N(R')_2$, $(CH_2)_nC(O)NH_2$, OR7', COR', NHCO—$C_{1-6}$-alkyl, —$COCH_2O$—P$(O)(OH)_2$; or (ii-b) one of R7 and R8 is H and the other is selected from the group consisting of halogen, $C_{1-3}$-haloalkyl, $C_{1-3}$-perhaloalkyl, $(CH_2)_nCN$, $OSO_2OH$, $OSO_2R''$, O-tosyl, OC(O)R—, $OC(O)(CH_2)_nCOOR'$, $OC(O)(CH_2)_nN(R')_2$, OC(O)$CH_2NHC(O)OR'$, $OPO(OR')_2$, $N_3$, $N(R')_2$, $NH(CH_2)_mOR'$, $NH(CH_2)_mSR'$, $NH(CH_2)_mNR'_2$, NHOR', and NHC(O)R'; or (ii-c) R7 and R8 form together a group selected from the group consisting of =$CH_2$, =CHR8', and CHCOOR7', wherein R8' is $C_{1-6}$-alkyl, $C_{1-6}$-alkoxy, or phenyl;

R' is H or $C_{1-6}$-alkyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O;

R'' is $C_{1-6}$-alkyl, $C_{1-3}$-haloalkyl, or $C_{1-3}$-perhaloalkyl;

R''' is C1-18-alkyl, C2-18-alkenyl, —$(CH_2)_n$—$C_{3-6}$-cycloalkyl, or optionally substituted phenyl; and n is 0, 1 or 2;

m is 1, 2 or 3;

or a pharmaceutically acceptable salt thereof.

Compounds of the present invention may be useful in therapy, especially in the treatment or prevention of steroid hormone dependent diseases or disorders requiring the lowering of the endogenous estradiol concentration or the inhibition of 17β-HSD enzymes, in animals, in particular mammals, and humans. In particular, compounds of formula (I) represent inhibitors of the 17β-HSD1 enzyme, possessing pharmacological properties for the treatment and/or prophylaxis of malignant steroid dependent diseases or disorders such as breast cancer, prostate carcinoma, ovarian cancer, uterine cancer, endometrial cancer and endometrial hyperplasia, but also for the treatment and/or prophylaxis of benign steroid dependent diseases or disorders such as endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome or lower urinary tract syndrome. Further estrogen-dependent diseases which may be treated and/or prevented with an effective amount of a compound of the invention include multiple sclerosis, obesity, rheumatoid arthritis, colon cancer, tissue wounds, skin wrinkles and cataracts. The compounds of the present invention typically have an inhibitory activity at the 17-β-HSD1 enzyme in the IC50 range of 0.1 nM to 1 µM. The inhibitory activity can be measured as explained in context of the experimental examples.

The invention also relates to pharmaceutical compositions comprising an effective amount of one or more compound(s) of formula (I).

Further the invention relates to a compound of formula (I) or a pharmaceutically acceptable salt thereof for use as a medicament.

The invention also relates to a compound of formula (I) or a pharmaceutically acceptable salt thereof for use in the treatment of estradiol dependent malign or benign diseases and disorders.

DETAILED DESCRIPTION OF THE INVENTION

Compounds of the invention contain steroidal core structure having a defined stereochemistry that is the natural configuration of estrogens.

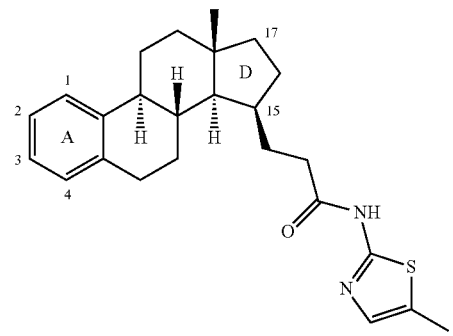

Compounds of the invention bear a methyl thiazolyl side chain at C15 in β-configuration which, together with the specific substitution pattern of the A and/or D ring(s), provides the inventive properties of the compounds of the present invention. Also, the C-17 carbon of the native estradiol core may further by substituted to further enhance the metabolic and/or inhibitory properties of the compounds of the present invention. Thus the compounds may exist in racemic form or optically active forms in respect to this carbon atom. All these forms are encompassed by the present invention.

The term "halogen" as used herein and hereafter by itself or as part of other groups refers to the Group VIIa elements and includes F, Cl, Br and I groups.

The term "alkyl" as used herein and hereafter as such or as part of haloalkyl, perhaloalkyl or alkoxy group is an aliphatic linear, branched or cyclic, especially linear or branched, hydrocarbon group having the indicated number of carbon atoms, for example $C_{1-6}$-alkyl has 1 to 6 carbon atoms in the alkyl moiety and thus, for example, $C_{1-4}$-alkyl includes methyl, ethyl, n-propyl, iso-propyl, n-butyl, sec-butyl, isobutyl, tert-butyl and $C_{1-6}$-alkyl additionally includes branched and straight chain pentyl and hexyl.

The term "haloalkyl" as used herein and hereafter refers to any of the above alkyl groups where one or more hydrogen atoms are replaced by halogen(s): in particular I, Br, F or Cl. Examples of haloalkyl groups include without limitation chloromethyl, fluoromethyl and —$CH_2CF_3$. The term "perhaloalkyl" is understood to refer to an alkyl group, in which all the hydrogen atoms are replaced by halogen atoms. Preferred examples include trifluoromethyl (—$CF_3$) and trichloromethyl (—$CCl_3$).

The term "$C_{3-6}$-cycloalkyl" as used herein and hereafter refers to cycloalkyl groups having 3 to 6 carbon atoms and thus includes cyclopropyl, cyclobutyl, cyclopentyl, and cyclohexyl.

The term "alkylenyl" as used herein and hereafter, is a divalent group derived from a straight or branched chain hydrocarbon of having suitably 1 to 6 carbon atoms. Representative examples of alkylenyl include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkenyl" as used herein and hereafter is an unsaturated linear or branched hydrocarbon group having at least one olefinic double bond between any two carbon atoms and having the indicated number of carbon atoms, for example $C_{2-6}$-alkenyl has 2 to 6 carbon atoms in the alkenyl moiety, such as ethenyl, propenyl, butenyl, pentenyl, and hexenyl. Examples of preferred alkenyls groups include, but are not limited to, linear alkenyl groups having a terminal double bond such as vinyl and allyl groups.

The term "$C_{2-6}$-alkynyl" as used herein is an unsaturated linear or branched hydrocarbon group having at least one olefinic triple bond between any two carbon atoms, such as ethynyl, propynyl, butynyl, pentynyl, and hexynyl. Examples of preferred alkynyl groups include, but are not limited to, linear alkynyls groups having a terminal triple bond.

The term "$C_{1-6}$-alkoxy" as used herein and hereafter refers to a —O—($C_{1-6}$-alkyl) group where the "$C_{1-6}$-alkyl" has the above-defined meaning. Examples of preferred alkoxy groups include, but are not limited to, methoxy, ethoxy, and iso-propyloxy.

The term "an 5 to 6 membered aliphatic or aromatic heterocyclic ring" refers to a monocyclic ring, which may be aliphatic or aromatic and comprises 1 or 2 heteroatoms each independently selected from N and O while the remaining ring atoms are carbon atoms. Representing groups include pyrrolidinyl, piperidinyl, morpholinyl, and piperazinyl, especially morpholinyl.

The term "an unsaturated or aromatic 5-membered heterocyclic ring" refers to a monocyclic ring which may be aromatic or unsaturated and comprises 1 or 2 heteroatoms each independently selected from N and O, while the remaining ring atoms are carbon atoms. The ring may be optionally substituted one or more times, in particular one time, with methyl at any suitable ring atom, including N, or with oxo at any suitable ring carbon atom. Preferred groups include, but are not limited to, oxazolone or and 1,3-oxazole, optionally substituted with methyl.

The term "optionally substituted" as used herein and hereafter in context of a phenyl group denotes phenyl that is either unsubstituted or substituted independently with one or more, in particular 1, 2, or 3, substituent(s) attached at any available atom to produce a stable compound, e.g. phenyl may be substituted once with a denoted substituent attached to o-, p- or m-position of the phenyl ring. In general "substituted" refers to a substituent group as defined herein in which one or more bonds to a hydrogen atom contained therein are replaced by a bond to a non-hydrogen atom unless otherwise denoted. The substituent groups are each independently selected from the group consisting of halogen, $C_{1-4}$-alkyl, in particular methyl; OH; $C_{1-4}$-alkoxy, in particular methoxy; CN; $NO_2$; and acetoxy. Preferably said phenyl is optionally substituted with acetoxy.

"Optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The expression "acid addition salt" includes any non-toxic organic and inorganic acid addition salts that compounds of formula (I) can form. Illustrative inorganic acids, which form suitable salts, include, but are not limited to, hydrogen chloride, hydrogen bromide, sulphuric and phosphoric acids. Illustrative organic acids, which form suitable salts, include, but are not limited to, acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. The term "acid addition salt" as used herein also comprises solvates which the compounds and salts thereof are able to form, such as, for example, hydrates, alcoholates, and the like. These salts also include salts useful for the chiral resolution of racemates.

The expression "base addition salt" includes any non-toxic base addition salts that the compound of formula (I) can form. Suitable base salts include, but are not limited to, those derived from inorganic bases such as aluminum, ammonium, calcium, copper, iron, lithium, magnesium, manganese, potassium, sodium, and zinc salts, in particular sodium and ammonium salts. Further examples of organic base addition salt include salts of trialkylamines, such as triethyl amine and trimethyl amine, and choline salts.

The present invention relates to an estrogen C-15 thiazole compound having a formula (I)

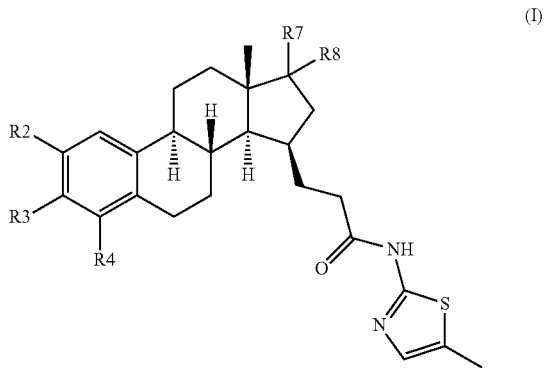

(I)

wherein (i-a) R2 and R4 are each independently selected from the group consisting of H, halogen, $C_{1-6}$-alkyl, $C_{1-2}$-haloalkyl, $C_{1-2}$-perhaloalkyl, CN, $NO_2$, $N_3$, $N(R')_2$, $(CH_2)_nN(R')_2$, OR', $(CH_2)_nOR'$, $CO_2R'$, CONHR', NHCOR", SCOR', or COR''', and R3 is selected from the group consisting of H, $C_{1-6}$-alkyl, $C_{1-3}$-haloalkyl, $C_{1-2}$-perhaloalkyl, $N(R')_2$, $N_3$, and $OR_3'$, wherein $R_3'$ is selected from the group consisting of R', benzyl, succinyl, optionally acylated glucuronyl, saturated 5 to 6 membered heterocyclic ring comprising 1 or 2 heteroatoms independently selected from N and O, $(CH_2)_nOH$, $SO_2OH$, $SO_2R"$, tosyl, $SO_2N(R')_2$, $PO(OR')_2$, $C(O)N(R')_2$, $C(O)(CH_2)_nN(R')_2$, and $C(O)R'''$; or (i-b) R2 and R3 or R3 and R4, together with the ring carbon atoms to which they are attached, form an unsaturated or aromatic 5-membered heterocyclic ring comprising 1 or 2 heteroatoms each independently selected from N and O, optionally substituted with methyl or oxo; and R4 or R2, respectively, is H and halogen;

(ii-a) one of R7 and R8 is OR7', wherein R7' is selected from the group consisting of H or $C_{1-6}$-alkyl and the other is selected from the group consisting of H, $C_{1-6}$-alkyl, $C_{1-2}$-haloalkyl, $C_{1-2}$-perhaloalkyl, $C_{2-6}$-alkenyl, $C_{2-6}$-alkynyl, benzyl, $(CH_2)_nCN$, $(CH_2)_nOH$, $N(R')_2$, $(CH_2)_nN(R')_2$, $C(O)OR'$, $(CH_2)_nC(O)OR'$, $C(O)N(R')_2$, $(CH_2)_nC(O)NH_2$, OR7', COR', NHCO—$C_{1-6}$-alkyl, —$COCH_2O$—$P(O)(OH)_2$; or (ii-b) one of R7 and R8 is H and the other is selected from the group consisting of halogen, $C_{1-3}$-haloalkyl, $C_{1-3}$-perhaloalkyl, $(CH_2)_nCN$, $OSO_2OH$, $OSO_2R"$, O-tosyl, $OC(O)R'''$, $OC(O)(CH_2)_nCOOR'$, $OC(O)(CH_2)_nN(R')_2$, $OC(O)CH_2NHC(O)OR'$, $OPO(OR')_2$, $N_3$, $N(R')_2$, $NH(CH_2)_mOR'$, $NH(CH_2)_mSR'$, $NH(CH_2)_mNR'_2$, NHOR', and NHC(O)R'; or (ii-c) R7 and R8 form together a group selected from the group consisting of =$CH_2$, =CHR8', and CHCOOR7', wherein R8' is $C_{1-6}$-alkyl, $C_{1-6}$-alkoxy, or phenyl;

R' is H or $C_{1-6}$-alkyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O, R" is $C_{1-6}$-alkyl, $C_{1-3}$-haloalkyl, or $C_{1-3}$-perhaloalkyl, R''' is C1-18-alkyl, C2-18-alkenyl, —$(CH_2)_n$—$C_{3-6}$-cycloalkyl, or optionally substituted phenyl, and n is 0, 1 or 2;

m is 1, 2 or 3;

or a pharmaceutically acceptable salt thereof.

In an embodiment of the invention, the invention relates to a compound of formula (I) wherein R2 and R4 are each independently selected from the group consisting of H, $C_{1-6}$-alkyl, $C_{1-2}$-haloalkyl, $C_{1-2}$-perhaloalkyl, CN, $NO_2$, $N_3$, $N(R')_2$, $(CH_2)_nN(R')_2$, OR', $(CH_2)_nOR'$, $CO_2R'$, CONHR', COR'', NHCOR" SCOR', or COR''' and R3 is selected from the group consisting of H, halogen, $C_{1-6}$-alkyl, $C_{1-2}$-haloalkyl, $C_{1-2}$-perhaloalkyl, $N(R')_2$, $(CH_2)_nNH_2$, $(CH_2)_nOR'$, $N_3$, and $OR_3'$, wherein $R_3'$ is selected from the group consisting of R', benzyl, succinyl, optionally acylated glucuronyl, saturated 5 to 6 membered heterocyclic ring comprising 1 or 2 heteroatoms independently selected from N and O, $(CH_2)_nOH$, $SO_2OH$, $SO_2R"$, tosyl, $SO_2N(R')_2$, $PO(OR')_2$, $C(O)N(R')_2$, $C(O)(CH_2)_nN(R')_2$, and $C(O)R'''$.

In an aspect of this embodiment R2 and R4 are each independently selected from the group consisting of H, halogen, $NO_2$, $NH_2$ and CN, in particular from the group consisting of H, F, Cl, Br, and I. In another aspect of this embodiment R3 is H, or OR3', wherein R3' is selected from the group consisting of H, $C_{1-4}$-alkyl, benzyl, saturated 5 to 6 membered heterocyclic ring comprising 1 or 2 heteroatoms independently selected from N and O, especially tetrahydropyranyl, $SO_2R"$, tosyl, $PO(OH)_2$, and $C(O)R'''$, wherein R''' is in particular $C_{1-12}$-alkyl, $C_{2-12}$-alkylenyl, or phenyl, yet in another aspect of the embodiment R3 is selected from the group consisting of H, OH, methoxy (OMe), benzyloxy (OBn), acyloxy (OAc), OC(O)Ph, mesyloxy (OMs), trifyloxy (OTf), tetrahydropyranyloxy, and $PO(OH)_2$.

In another aspect of this embodiment (ii-b) one of R7 and R8 is H and the other is selected from the group consisting of halogen, $C_{1-3}$-haloalkyl, $C_{1-3}$-perhaloalkyl, $(CH_2)_nCN$, $OSO_2OH$, $OSO_2R"$, O-tosyl, $OC(O)R'''$, $OC(O)(CH_2)_n$ COOR', $OC(O)(CH_2)_nN(R')_2$, $OC(O)CH_2NHC(O)OR'$, $OPO(OR)_2$, $N_3$, $N(R')_2$, NHOR', and NHC(O)R'.

In another embodiment of the present invention, the invention relates to a compound of formula (I) wherein R7 is OR7' and having the formula (Ia)

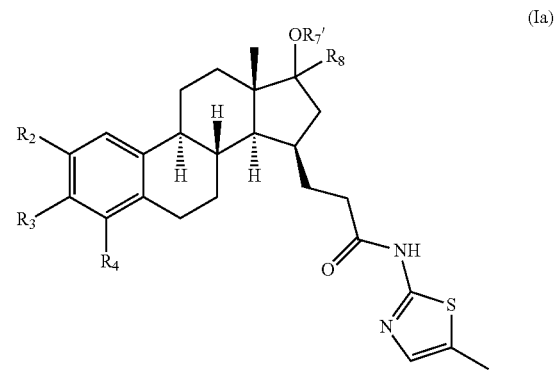

(Ia)

wherein R2 to R4 and R7' and R8 are as defined above.

In an aspect of this embodiment R2 and R4 are each independently is H or halogen. In another aspect of this embodiment R3 is selected from the group consisting of OH, $C_{1-6}$-alkoxy, and OAc. In yet another aspect of this embodiment R7' is H or methyl. In a further aspect of the embodiment R8 is selected from the group consisting of $C_{1-6}$-alkyl, $(CH_2)_nCN$ and $(CH_2)_nC(O)NH_2$.

In yet another embodiment of the present invention, the invention relates to a compound of formula (I) wherein R7 is OH and having the formula (Ib)

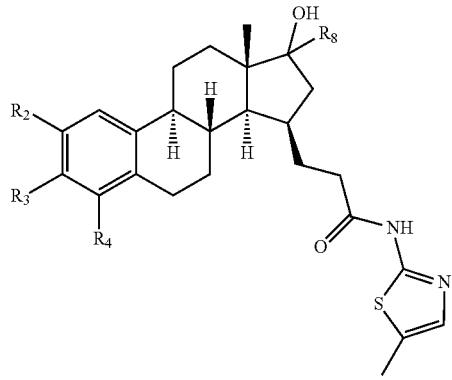

(Ib)

wherein R2 to R4 and R8 are as defined above.

In an aspect of embodiment are R8 is selected from the group consisting of $C_{1-6}$-alkyl, $C_{1-3}$-haloalkyl, $C_{1-3}$-perhaloalkyl, $(CH_2)_nCN$, $(CH_2)_nOH$, $(CH_2)_nN(R')_2$, $(CH_2)_nC(O)OR$, $C(O)N(R')_2$, and $(CH_2)_nC(O)NH_2$, in particular from $C_{1-6}$-alkyl, $(CH_2)_nCN$ and $(CH_2)_nC(O)NH_2$, wherein each R' is as defined above, especially H or methyl. Further in another aspect of this embodiment R2 and R4 are each independently H or halogen. In yet another aspect of this embodiment R3 is selected from the group consisting of OH, $C_{1-7}$-alkoxy, especially methoxy, and acyloxy.

In a further embodiment of the present invention, the invention relates to a compound of formula (I) or a pharmaceutically acceptable salt thereof wherein R7 is OH, R8 is H, and which compound has the formula (Ic)

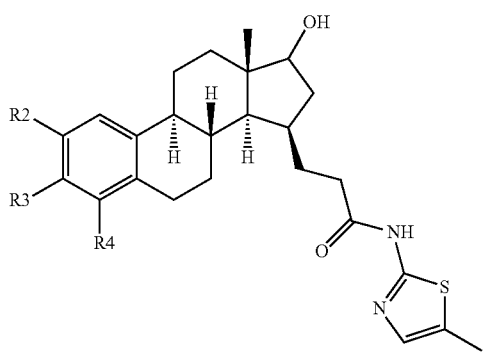

(Ic)

wherein R2 to R4 are as defined in above.

In an aspect of this embodiment R2 and R4 are each independently H or halogen. In another aspect of this invention R3 is selected from the group consisting of H, OH, $C_{1-7}$-alkoxy, especially methoxy, benzyloxy and acyloxy.

In yet a further embodiment of the present invention relates to a compound of formula (I) or a pharmaceutically acceptable salt thereof, wherein R7 is OMe, R8 is H, and which compound has the formula (Id)

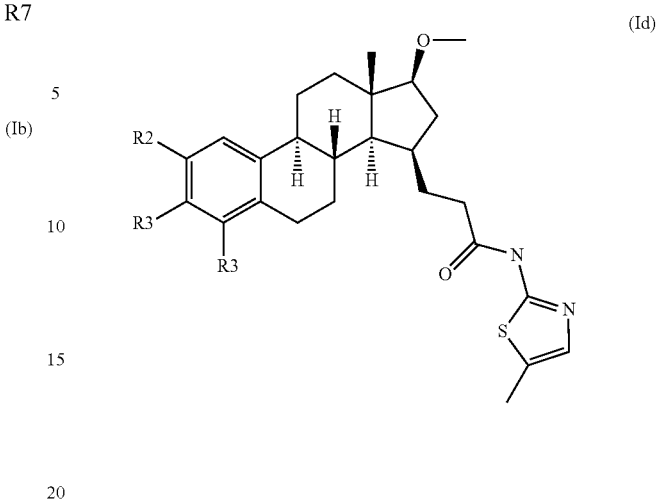

(Id)

wherein R2 to R4 are as defined in above.

In an aspect of this embodiment R2 and R4 are each independently H or halogen. In another aspect of this embodiment R3 is selected from the group consisting of OH, $C_{1-6}$-alkoxy, especially methoxy, benzyloxy and acyloxy.

In an alternative embodiment of the present invention, the invention relates to a compound of formula (I) or a pharmaceutically acceptable salt thereof wherein R7 is OR7' and R8 is H, and which compound has the formula (Ie)

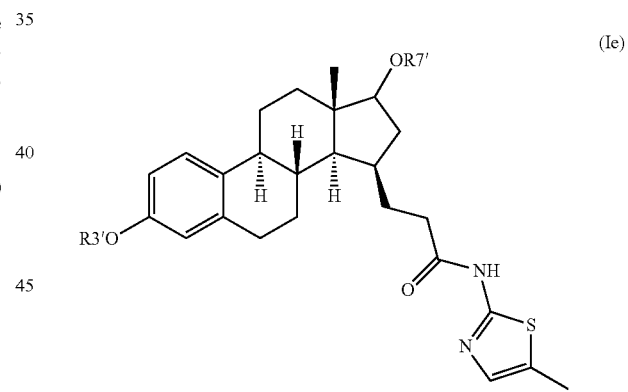

(Ie)

wherein R3' and R7' are as defined in above.

In an aspect of this embodiment one of R3' and R7' is H and the other one is selected from the group consisting of $SO_2OH$, $SO_2R''$, tosyl, $SO_2N(R')_2$, $PO(OR')_2$, $C(O)N(R')_2$, $C(O)(CH_2)_nN(R')_2$, and $C(O)R'''$. Alternatively both R3' and R7' are independently selected from the group consisting of $SO_2OH$, $SO_2R''$, tosyl, $SO_2N(R')_2$, $PO(OR')_2$, $C(O)N(R')_2$, $C(O)(CH_2)_nN(R')_2$, and $C(O)R'''$.

In a further alternative embodiment of the present invention, the invention relates to a compound of formula (I) or a pharmaceutically acceptable salt thereof wherein R7 is $NH(CH_2)_mOR'$, $NH(CH_2)_mSR'$, $NH(CH_2)_mNR'_2$ and R8 is H, and which compound has the formula (If)

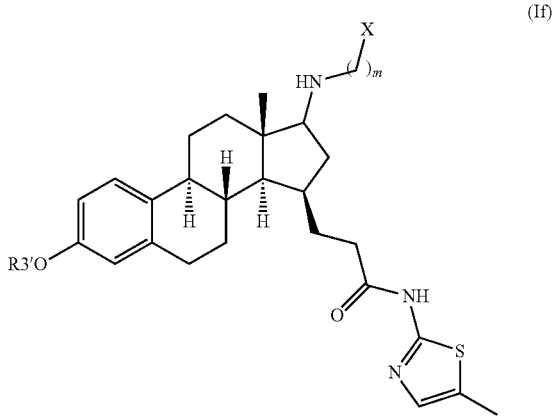

(If)

wherein m is 1, 2 or 3, X is OR', SR', NR'$_2$, and R' is as defined above. In a preferred aspect of this embodiment R' is selected from H and C$_{1-3}$-alkyl.

In an aspect of the present invention the invention relates to a compound of formula (I), selected from the group consisting of:

Compound 1 3-((13S,15R,17S)-3,17-Dihydroxy-13-methyl-7,8,9,11,12,13,14,15,16,17decahydro-6H-cyclopenta[a]phenanthren-15-yl)-N-(5-methylthiazol-2-yl)propanamide;

Compound 3 Acetic acid (13S,15R,17S)-17-hydroxyl-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 6 3-((13S,15R,17S)-17-Hydroxy-3-methoxy-13-methyl-7,8,9,11,12,13,14,15,16,17-decahydro-6H-cyclopenta[a]phenanthren-15-yl)-N-(5-methylthiazol-2-yl)propanamide;

Compound 8 3-((13S,15R,17S)-17-Hydroxy-3-methoxy-13-methyl-7,8,9,11,12,13,14,15,16,17-decahydro-6H-cyclopenta[a]phenanthren-15-yl)-propionic acid methyl ester;

Compound 9 3-((13S,15R,17S)-3,17-Dimethoxy-13-methyl-7,8,9,11,12,13,14,15,16,17-decahydro-6H-cyclopenta[a]phenanthren-15-yl)-propionic acid methyl ester;

Compound 10 3-((13S,15R,17S)-3,17-Dimethoxy-13-methyl-7,8,9,11,12,13,14,15,16,17-decahydro-6H-cyclopenta[a]phenanthren-15-yl)-propionic acid;

Compound 11 3-((13S,15R,17S)-3,17-Dimethoxy-13-methyl-7,8,9,11,12,13,14,15,16,17-decahydro-6H-cyclopenta[a]phenanthren-15-yl)-N-(5-methylthiazol-2-yl)propanamide;

Compound 13 Methyl 3-((13S,15R,17S)-3-(benzyloxy)-17-hydroxy-13-methyl-7,8,9,11,12,13,14,15,16,17-decahydro-6H-cyclopenta[a]phenanthren-15-yl)propanoate;

Compound 14 Methyl 3-((13S,15R,17S)-3-(benzyloxy)-17-methoxy-13-methyl-7,8,9,11,12,13,14,15,16,17-decahydro-6H-cyclopenta[a]phenanthren-15-yl)propanoate;

Compound 15 3-((13S,15R,17S)-3-(benzyloxy)-17-methoxy-13-methyl-7,8,9,11,12,13,14,15,16,17-decahydro-6H-cyclopenta[a]phenanthren-15-yl)propanoic acid;

Compound 16 3-((13S,15R,17S)-3-hydroxy-17-methoxy-13-methyl-7,8,9,11,12,13,14,15,16,17-decahydro-6H-cyclopenta[a]phenanthren-15-yl)propanoic acid;

Compound 17 3-((13S,15R,17S)-3-hydroxy-17-methoxy-13-methyl-7,8,9,11,12,13,14,15,16,17-decahydro-6H-cyclopenta[a]phenanthren-15-yl)-N-(5-methylthiazol-2-yl)propanamide;

Compound 18 (13S,15R,17S)-17-methoxy-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate;

Compound 19 3-((13S,15R,17S)-17-butyl-3,17-dihydroxy-13-methyl-7,8,9,11,12,13,14,15,16,17-decahydro-6H-cyclopenta[a]phenanthren-15-yl)-N-(5-methylthiazol-2-yl)propanamide;

Compound 20 3-((13S,15R,17S)-17-butyl-17-hydroxy-3-methoxy-13-methyl-7,8,9,11,12,13,14,15,16,17-decahydro-6H-cyclopenta[a]phenanthren-15-yl)-N-(5-methylthiazol-2-yl)propanamide;

Compound 21 3-((13S,15R,17S)-17-cyano-3,17-dihydroxy-13-methyl-7,8,9,11,12,13,14,15,16,17-decahydro-6H-cyclopenta[a]phenanthren-15-yl)-N-(5-methylthiazol-2-yl)propanamide;

Compound 22 (13S,15R,17S)-17-cyano-17-hydroxy-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate;

Compound 23 3-((13S,15R,17S)-17-cyano-17-hydroxy-3-methoxy-13-methyl-7,8,9,11,12,13,14,15,16,17-decahydro-6H-cyclopenta[a]phenanthren-15-yl)-N-(5-methylthiazol-2-yl)propanamide;

Compound 24 3-((13S,15R,17R)-17-(cyanomethyl)-3,17-dihydroxy-13-methyl-7,8,9,11,12,13,14,15,16,17-decahydro-6H-cyclopenta[a]phenanthren-15-yl)-N-(5-methylthiazol-2-yl)propanamide;

Compound 25 3-((13S,15R,17R)-17-(cyanomethyl)-17-hydroxy-3-methoxy-13-methyl-7,8,9,11,12,13,14,15,16,17-decahydro-6H-cyclopenta[a]phenanthren-15-yl)-N-(5-methylthiazol-2-yl)propanamide;

Compound 26 3-((13S,15R,17R)-17-(2-amino-2-oxoethyl)-3,17-dihydroxy-13-methyl-7,8,9,11,12,13,14,15,16,17-decahydro-6H-cyclopenta[a]phenanthren-15-yl)-N-(5-methylthiazol-2-yl)propanamide;

Compound 28 3-((13S,15R,17S)-2,4-dibromo-3,17-dihydroxy-13-methyl-7,8,9,11,12,13,14,15,16,17-decahydro-6H-cyclopenta[a]phenanthren-15-yl)-N-(5-methylthiazol-2-yl)propanamide;

Compound 29 3-((13S,15R,17S)-2,4-dibromo-3-hydroxy-17-methoxy-13-methyl-7,8,9,11,12,13,14,15,16,17-decahydro-6H-cyclopenta[a]phenanthren-15-yl)-N-(5-methylthiazol-2-yl)propanamide;

Compound 30 3-((13S,15R,17R)-2,4-dibromo-17-(cyanomethyl)-3,17-dihydroxy-13-methyl-7,8,9,11,12,13,14,15,16,17-decahydro-6H-cyclopenta[a]phenanthren-15-yl)-N-(5-methylthiazol-2-yl)propanamide;

Compound 31 3-((13S,15R,17S)-2,4-dibromo-17-butyl-3,17-dihydroxy-13-methyl-7,8,9,11,12,13,14,15,16,17-decahydro-6H-cyclopenta[a]phenanthren-15-yl)-N-(5-methylthiazol-2-yl)propanamide;

Compound 33 3-((13S,15R,17S)-17-hydroxy-13-methyl-3-((tetrahydro-2H-pyran-2-yl)oxy)-7,8,9,11,12,13,14,15,16,17-decahydro-6H-cyclopenta[a]phenanthren-15-yl)-N-(5-methylthiazol-2-yl)propanamide;

Compound 35 3-((13S,15R,17S)-3-(benzyloxy)-17-hydroxy-13-methyl-7,8,9,11,12,13,14,15,16,17-decahydro-6H-cyclopenta[a]phenanthren-15-yl)-N-(5-methylthiazol-2-yl)propanamide;

Compound 36 Acetic acid (13S,15R,17S)-3-hydroxy-13-methyl-15-[2-(5-methyl-thiazol-2-ylcarbamoyl)-ethyl]-17-oxo-7,8,9,11,12,13,14,15,16,17-decahydro-6H-cyclopenta[a]phenanthren-17-yl ester;

Compound 37 (13S,15R,17S)-3-(benzyloxy)-13-methyl-15-(3-((5-methylthiazol-2-yl)amino)-3-oxopropyl)-7,8,9,11,12,13,14,15,16,17-decahydro-6H-cyclopenta[a]phenanthren-17-yl pentanoate;

Compound 38 Pentanoic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 39 3-Cyclopentyl-propionic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 40 Dodecanoic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 41 Dodecanoic acid (13S,15R,17S)-17-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 42 Undec-10-enoic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 43 Succinic acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester;

Compound 44 Succinic acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester sodium salt;

Compound 45 Acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 46 Phosphoric acid mono-{(13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester;

Compound 47 Phosphoric acid mono-{(13S,15R,17S)-3-methoxy-13-methyl-15-[2-(5-methyl-thiazol-2-ylcarbamoyl)-ethyl]-17-oxo-7,8,9,11,12,13,14,15,16,17-decahydro-6H-cyclopenta[a]phenanthren-17-yl}ester disodium salt;

Compound 48 tert-Butoxycarbonylamino-acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 49 Amino-acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 50 Dimethylamino-acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 51 Methanesulphonic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 52 Acetic acid (13S,15R,17S)-17-acetoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 53 Pentanoic acid (13S,15R,17S)-13-methyl-15-[2-(5-methylthiazol-2-ylcarbamoyl)-ethyl]-3-pentanoyloxy-7,8,9,11,12,13,14,15,16,17-decahydro-6H-cyclopenta[a]phenanthren-17-yl ester;

Compound 54 Dodecanoic acid (13S,15R,17S)-3-dodecanoyloxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 55 Benzoic acid (13S,15R,17S)-17-acetoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 56 Undec-10-enoic acid (13S,15R,17S)-13-methyl-15-[2-(5-methylthiazol-2-yl carbamoyl)-ethyl]-3-undec-10-enoyloxy-7,8,9,11,12,13,14,15,16,17-decahydro-6H-cyclopenta[a]phenanthren-17-yl ester;

Compound 57 Phosphoric acid mono-{(13S,15R,17S)-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester;

Compound 58 Phosphoric acid mono-{(13S,15R,17S)-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester tetrasodium salt;

Compound 59 Acetic acid (13S,15R,17S)-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester;

Compound 60 Phosphoric acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester;

Compound 61 Phosphoric acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester trisodium salt;

Compound 62 3-Cyclopentyl-propionic acid (13S,15R)-3-acetoxy-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-17-yl ester;

Compound 63 p-Tosylsulphonic acid (13S,15R,17S)-13-methyl-15-[2-(5-methylthiazol-2-ylcarbamoyl)-ethyl]-17-p-tosylsulphonyloxy-7,8,9,11,12,13,14,15,16,17-decahydro-6H-cyclopenta[a]phenanthren-3-yl ester;

Compound 64 Methanesulphonic acid (13S,15R,17S)-17-methanesulphonyloxy-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester;

Compound 67 3-((13S,15R)-17-Hydroxy13-methyl-7,8,9,11,12,13,14,15,16,17-decahydro-6H-cyclopenta[a]phenanthren-15-yl)-N-(5-methylthiazol-2-yl)propanamide;

Compound 68 3-{(13S,15R)-17-Formylamino-3-hydroxy-13-methyl-7,8,9,11,12,13,14,15,16,17-decahydro-6H-cyclopenta[a]phenanthren-15-yl}-N-(5-methylthiazol-2-yl)propanamide;

or a pharmaceutically acceptable salt thereof.

A more preferred embodiment of the present invention relates to a compound of formula (I) selected from the group consisting of:

Compound 17 3-((13S,15R,17S)-3-hydroxy-17-methoxy-13-methyl-7,8,9,11,12,13,14,15,16,17-decahydro-6H-cyclopenta[a]phenanthren-15-yl)-N-(5-methylthiazol-2-yl)propanamide;

Compound 19 3-((13S,15R,17S)-17-butyl-3,17-dihydroxy-13-methyl-7,8,9,11,12,13,14,15,16,17-decahydro-6H-cyclopenta[a]phenanthren-15-yl)-N-(5-methylthiazol-2-yl)propanamide;

Compound 46 Phosphoric acid mono-{(13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester; and Compound 60 Phosphoric acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester;

or a pharmaceutically acceptable salt thereof.

Examples of the Invention

Representative examples of compounds of formula (I) are shown in Table 1.

TABLE 1

| # | Compound | NMR |
|---|----------|-----|
| 1 | 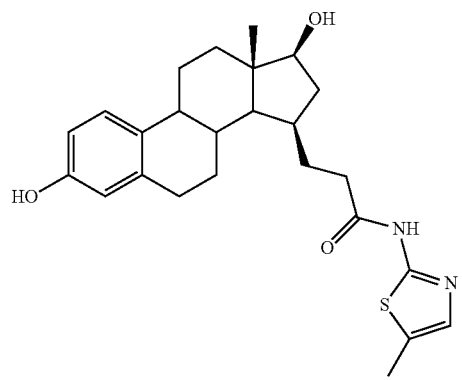 [SMILES: Cc1cnc(NC(=O)CC[C@@H]2C[C@H](O)[C@@]3(C)CCC4c5ccc(O)cc5CCC4C23)s1] | $^1$H-NMR (CDCl$_3$ + MeOH-d$_4$): 0.89 (s, 3H), 1.18-2.52 (m, 19H), 2.83 (m, 2H), 3.68 (t, 1H), 6.57-6.65 (m, 2H), 7.03 (d, 1H), 7.11 (d, 1H). |
| 3 | 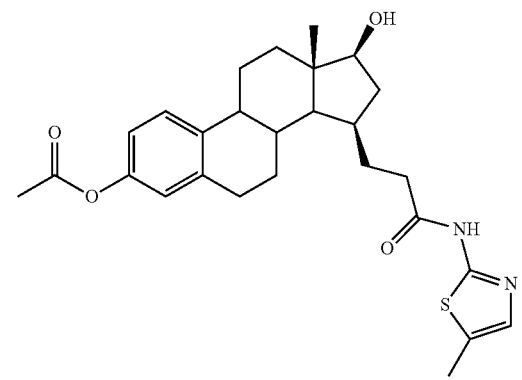 [SMILES: CC(=O)Oc1ccc2c(c1)CCC1C2CC[C@@]2(C)C1[C@H](CCC(=O)Nc1ncc(C)s1)C[C@@H]2O] | $^1$H-NMR (DMSO-d$_6$): 0.79 (s, 3H), 1.1-2.4 (m, 22H), 2.82 (m, 2H), 4.55 (d, 1H), 6.81 (s, 1H), 6.85 (s, 1H), 7.10 (s, 1H), 7.28 (d, 1H), 11.89 (s, 1H). |
| 6 | 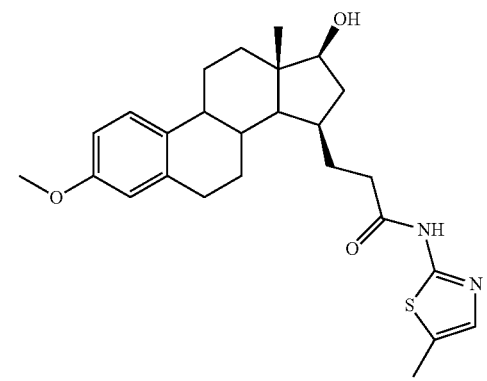 [SMILES: COc1ccc2c(c1)CCC1C2CC[C@@]2(C)C1[C@H](CCC(=O)Nc1ncc(C)s1)C[C@@H]2O] | $^1$H-NMR (DMSO-d$_6$): 0.78 (s, 3H), 1.23-2.32 (m, 22H), 2.79 (m, 2H), 3.69 (s, 3H), 4.56 (d, 1H), 6.63 (m, 2H), 7.10 (s, 1H), 7.15 (d, 1H), 11.90 (s, 1H). |

TABLE 1-continued

| # | Compound | NMR |
|---|---|---|
| 11 | | $^1$H-NMR (DMSO-$d_6$): 0.83 (s, 3H), 1.18-2.32 (m, 22H), 2.79 (m, 2H), 3.21 (t, 1H), 3.27 (s, 3H), 3.69 (s, 3H), 6.64 (m, 2H), 7.10 (s, 1H), 7.12 (d, 1H), 11.89 (s, 1H). |
| 17 | | $^1$H-NMR (DMSO-$d_6$): 0.84 (s, 3H), 1.10-2.60 (m, 20H), 2.73 (m, 2H), 3.28 (s, 3H), 6.45-6.48 (m, 2H), 7.03 (d, 1H), 7.11 (s, 1H), 9.02 (s, 1H), 11.90 (s, 1H). |
| 18 | | $^1$H-NMR (CDCl$_3$): 0.91 (s, 3H), 1.10-2.70 (m, 22H), 2.85 (m, 2H), 3.30 (t, 1H), 3.38 (s, 3H), 6.80-6.86 (m, 2H), 7.06 (s, 1H), 7.26 (d, 1H), 11.91 (s, 1H). |
| 19 | | $^1$H-NMR (DMSO-$d_6$): 0.88 (m, 6H), 1.14-2.30 (m, 22H), 2.33 (s, 3H), 2.73 (m, 2H), 3.88 (s, 1H), 6.47 (m, 2H), 7.02 (d, 1H), 7.11 (s, 1H), 9.00 (s, 1H), 11.89 (s, 1H). |

TABLE 1-continued

| # | Compound | NMR |
|---|---|---|
| 20 | | ¹H-NMR (CDCl₃): 0.94-1.05 (m, 6H), 1.25-2.52 (m, 25H), 2.85 (m, 2H), 3.78 (s, 3H), 6.64-6.75 (m, 2H), 7.07 (s, 1H), 7.19 (d, 1H), 11.66 (br s, 1H). |
| 21 | | ¹H-NMR (CDCl₃): 0.97 (s, 3H), 1.38-2.60 (m, 16H), 2.29 (s, 3H), 2.41 (s, 3H), 2.71-2.90 (m, 3H), 6.84 (m, 2H), 7.03 (s, 1H), 7.24 (d, 1H). |
| 22 | | ¹H-NMR (CDCl₃ + MeOH-d4): 0.97 (s, 3H), 1.30-2.80 (m, 21H), 6.57-6.65 (m, 2H), 7.04 (s, 1H), 7.09 (d, 1H). |
| 23 | | ¹H-NMR (CDCl₃): 1.01 (s, 3H), 1.40-2.90 (m, 21H), 3.77 (s, 3H), 6.63-6.73 (m, 2H), 7.03 (s, 1H), 7.18 (d, 1H). |

TABLE 1-continued

| # | Compound | NMR |
|---|---|---|
| 24 | | $^1$H-NMR (DMSO-d$_6$): 0.90 (s, 3H), 1.15-2.84 (m, 23H), 4.99 (s, 1H), 6.46-6.52 (m, 2H), 7.01-7.11 (m, 2H), 9.01 (s, 1H), 11.93 (s, 1H). |
| 25 | | $^1$H-NMR (DMSO-d$_6$): 0.90 (s, 3H), 1.20-2.84 (m, 23H), 3.69 (s, 3H), 4.99 (s, 1H), 6.63-6.68 (m, 2H), 7.12-7.17 (m, 2H), 11.94 (s, 1H). |
| 26 | | $^1$H-NMR (DMSO-d$_6$): 0.91 (s, 3H), 1.15-2.84 (m, 22H), 5.66 (br s, 1H), 6.46 (m, 2H), 7.05 (d, 1H), 7.11 (s, 1H), 7.23 (br s, 1H), 7.61 (br s, 1H), 9.03 (br s, 1H), 11.91 (s, 1H). |
| 28 | | $^1$H-NMR (DMSO-d$_6$): 0.76 (s, 3H), 1.06-1.50 (m, 8H), 1.65-1.95 (m, 3H), 2.05-2.90 (m, 10H), 3.45-3.60 (m, 1H), 4.56 (d, 1H), 7.10 (s, 1H), 7.39 (s, 1H), 9.52 (s, 1H), 11.90 (s, 1H). |

TABLE 1-continued
| # | Compound | NMR |
|---|---|---|
| 29 | 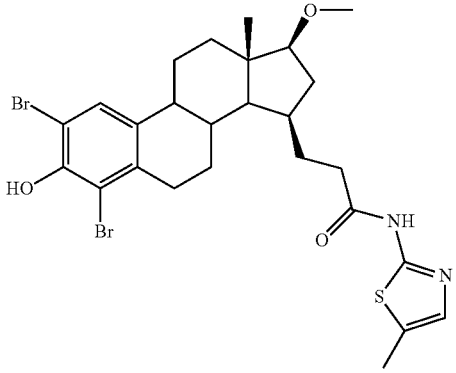 [SMILES: CO[C@H]1C[C@@H](CCC(=O)Nc2ncc(C)s2)C2C3CCc4c(cc(Br)c(O)c4Br)C3CC[C@@]21C] | ¹H-NMR (CDCl₃ + MeOH-d₄): 0.91 (s, 3H), 1.3-1.7 (m, 7H), 2.0-2.9 (m, 14H), 3.40 (s, 3H), 7.02 (s, 1H), 7.38 (s, 1H). |
| 30 | 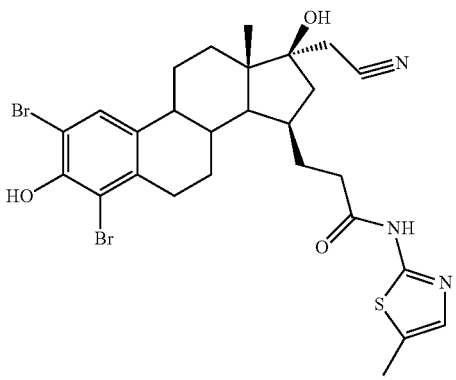 [SMILES: Cc1cnc(NC(=O)CC[C@@H]2C[C@@](O)(CC#N)[C@@]3(C)CCC4c5cc(Br)c(O)c(Br)c5CCC4C23)s1] | ¹H-NMR (DMSO-d₆): 0.88 (s, 3H), 1.15-2.84 (m, 23H), 5.00 (s, 1H), 7.11 (s, 1H), 7.38 (s, 1H), 9.54 (br s, 1H), 11.93 (s, 1H). |
| 31 | 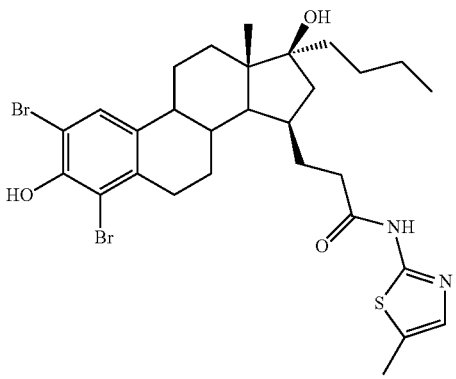 [SMILES: CCCC[C@]1(O)C[C@@H](CCC(=O)Nc2ncc(C)s2)C2C3CCc4c(cc(Br)c(O)c4Br)C3CC[C@@]21C] | ¹H-NMR (CDCl₃): 0.91 (t, 3H), 0.99 (s, 3H), 1.30-2.81 (m, 27H), 7.06 (s, 1H), 7.38 (s, 1H). |
| 33 | 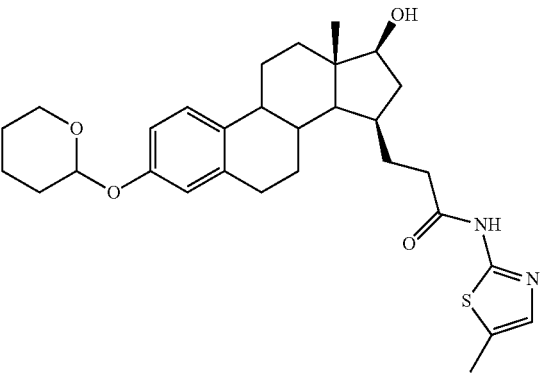 [SMILES: Cc1cnc(NC(=O)CC[C@@H]2C[C@H](O)[C@@]3(C)CCC4c5ccc(OC6CCCCO6)cc5CCC4C23)s1] | ¹H-NMR (DMSO-d₆): 0.78 (s, 3H), 1.23-2.32 (m, 22H), 2.78 (m, 2H), 3.50 and 3.74 (2 × m), 3.69 (s, 3H), 4.55 (d, 1H), 5.39 (s, 1H), 6.75 (m, 2H), 7.10 (s, 1H), 7.17 (d, 1H), 11.88 (s, 1H). |

TABLE 1-continued
| # | Compound | NMR |
|---|----------|-----|
| 35 | 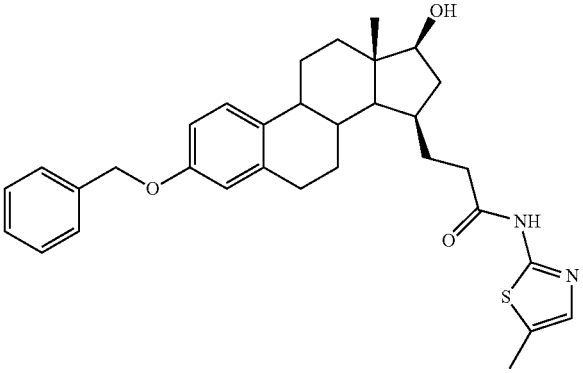 [SMILES: Cc1cnc(NC(=O)CC[C@@H]2C[C@H](O)[C@@]3(C)CCC4c5ccc(OCc6ccccc6)cc5CCC4C23)s1] | $^1$H-NMR (CDCl$_3$): 0.89 (s, 3H), 1.16-2.60 (m, 19H), 2.85 (m, 2H), 3.71 (t, 1H), 5.02 (s, 2H), 6.74 (m, 2H), 7.05 (d, 1H), 7.15-7.46 (m, 5H). |
| 36 | 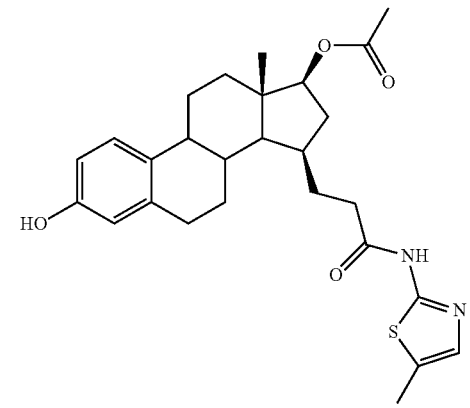 [SMILES: CC(=O)O[C@H]1C[C@@H](CCC(=O)Nc2ncc(C)s2)C2C3CCc4cc(O)ccc4C3CC[C@@]21C] | $^1$H-NMR (DMSO-d$_6$): 0.89 (s, 3H), 1.20-2.37 (m, 22H), 2.74 (m, 2H), 4.59 (t, 1H), 6.48 (m, 2H), 7.02 (d, 1H), 7.10 (s, 1H), 9.04 (s, 1H), 11.89 (s, 1H). |
| 37 | 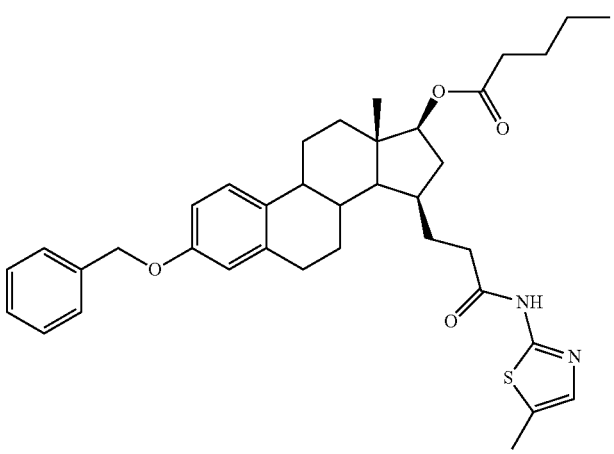 [SMILES: CCCCC(=O)O[C@H]1C[C@@H](CCC(=O)Nc2ncc(C)s2)C2C3CCc4cc(OCc5ccccc5)ccc4C3CC[C@@]21C] | $^1$H-NMR (CDCl$_3$): 0.93 (t, 3H), 0.96 (s, 3H), 1.34-2.59 (m, 25H), 2.87 (m, 2H), 4.72 (t, 3H), 5.03 (s, 2H), 6.73 (s, 1H), 6.78 (m, 1H), 6.98 (s, 1H), 7.18 (d, 1H), 7.41 (m, 5H). |

TABLE 1-continued
| # | Compound | NMR |
|---|---|---|
| 38 | 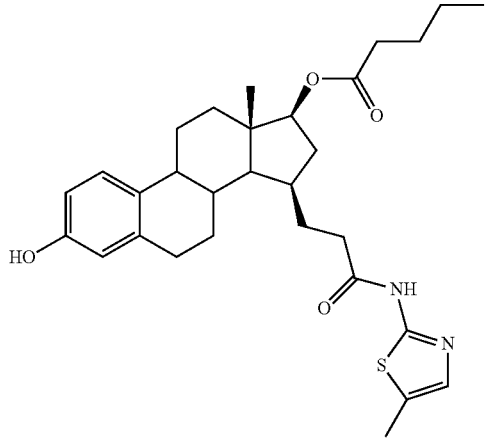 [SMILES: CCCCC(=O)O[C@H]1C[C@@H](CCC(=O)Nc2ncc(C)s2)C2C3CCc4cc(O)ccc4C3CC[C@@]21C] | $^1$H-NMR (DMSO-$d_6$): 0.86 (t, 3H), 0.88 (s, 3H), 1.23-2.36 (m, 25H), 2.73 (m, 2H), 4.60 (t, 1H), 6.48 (m, 2H), 7.01 (d, 1H), 7.10 (s, 1H), 9.11 (br s, 1H), 11.88 (s, 1H). |
| 39 | 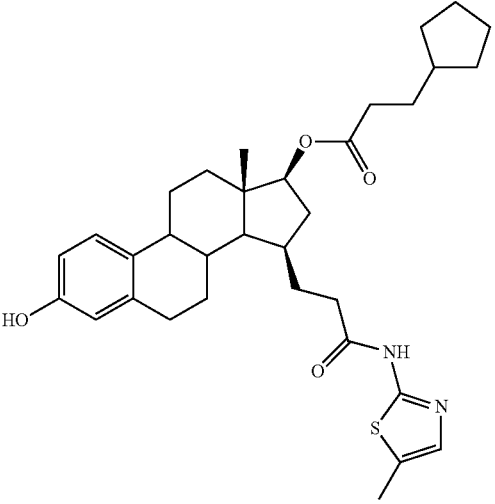 [SMILES: Cc1cnc(NC(=O)CC[C@@H]2C[C@H](OC(=O)CCC3CCCC3)[C@@]3(C)CCC4c5ccc(O)cc5CCC4C23)s1] | $^1$H-NMR (DMSO-$d_6$): 0.89 (s, 3H), 0.95-2.90 (m, 34H), 4.61 (m, 1H), 6.45-6.50 (m, 2H), 7.00-7.10 (m, 2H), 9.03 (s, 1H), 11.89 (s, 1H). |
| 40 | 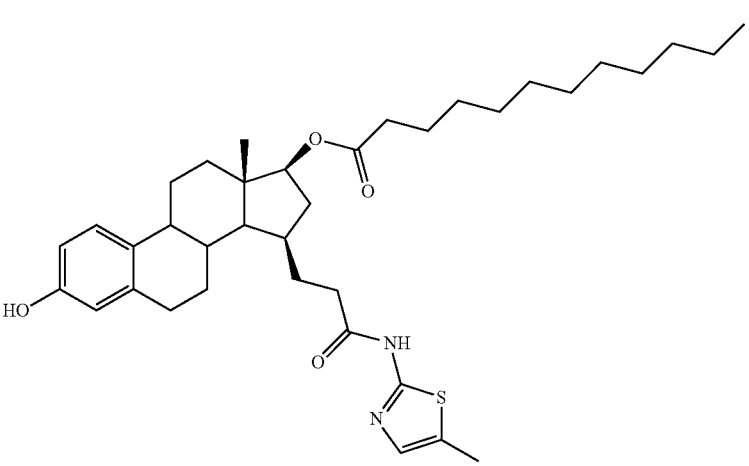 [SMILES: CCCCCCCCCCCC(=O)O[C@H]1C[C@@H](CCC(=O)Nc2ncc(C)s2)C2C3CCc4cc(O)ccc4C3CC[C@@]21C] | $^1$H-NMR (DMSO-$d_6$): 0.88 (m, 6H), 1.10-2.90 (m, 41H), 4.62 (m, 1H), 6.45-6.50 (m, 2H), 7.00-7.10 (m, 2H), 9.02 (s, 1H), 11.89 (s, 1H). |

| # | Compound | NMR |
|---|---|---|
| 41 | 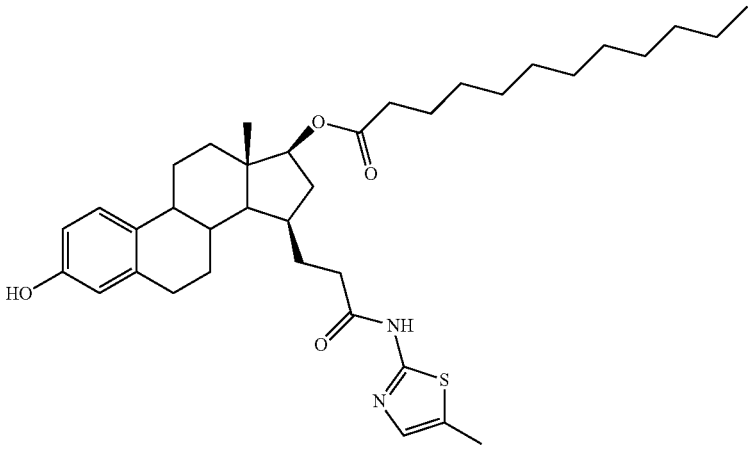 [SMILES: CCCCCCCCCCCC(=O)O[C@H]1C[C@@H](CCC(=O)Nc2ncc(C)s2)C2C3CCc4cc(O)ccc4C3CC[C@@]21C] | $^1$H-NMR (DMSO-$d_6$): 0.88 (m, 6H), 1.10-2.90 (m, 41H), 4.62 (m, 1H), 6.45-6.50 (m, 2H), 7.00-7.10 (m, 2H), 9.02 (s, 1H), 11.89 (s, 1H). |
| 42 | 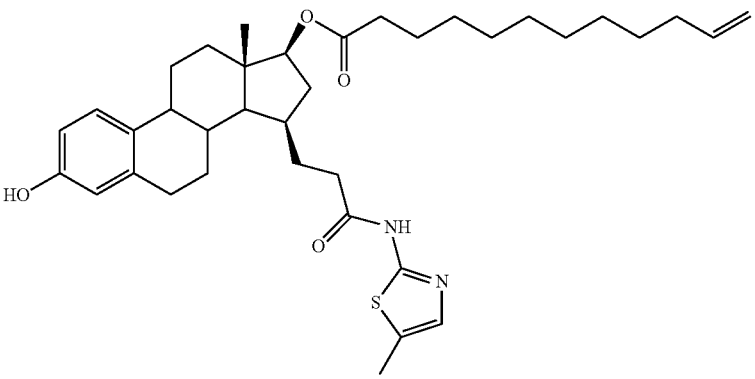 [SMILES: C=CCCCCCCCCCC(=O)O[C@H]1C[C@@H](CCC(=O)Nc2ncc(C)s2)C2C3CCc4cc(O)ccc4C3CC[C@@]21C] | $^1$H-NMR (DMSO-$d_6$): 0.89 (s, 3H), 1.10-2.50 (m, 35H), 2.74 (m, 2H), 4.61 (t, 1H), 4.90-5.02 (m, 2H), 5.65-5.90 (m, 1H), 6.45-6.51 (m, 2H), 7.00-7.10 (m, 2H), 9.01 (s, 1H), 11.89 (s, 1H). |
| 43 | 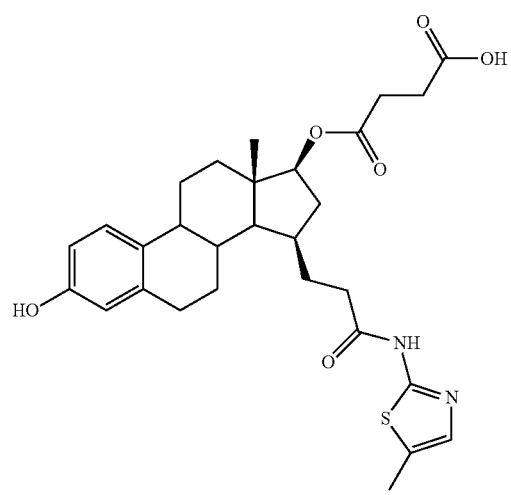 [SMILES: Cc1cnc(NC(=O)CC[C@@H]2C[C@H](OC(=O)CCC(=O)O)[C@@]3(C)CCC4c5ccc(O)cc5CCC4C23)s1] | 1H-NMR (DMSO-d6): 0.90 (t, 3H), 1.20-2.40 (m, 23H), 2.75 (m, 2H), 4.62 (t, 1H), 6.46 (s, 1H), 6.50 (d, 1H), 7.03 (d, 1H), 7.11 (s, 1H), 9.00 (s, 1H), 11.91 (s, 1H), 12.21 (s, 1H). |

TABLE 1-continued
| # | Compound | NMR |
|---|----------|-----|
| 44 | 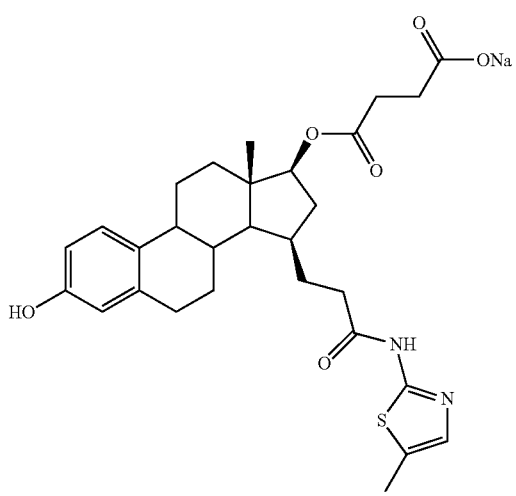 | 1H-NMR (DMSO-d6): 0.87 (s, 3H), 1.20-2.50 (m, 23 H), 2.65-2.80 (m, 2H), 4.57 (t, 1H), 6.45 (s, 1H), 6.50 (d, 1H), 7.00 (d, 1H), 7.10 (s, 1H), 11.97 (s, 1H). |
| 45 | 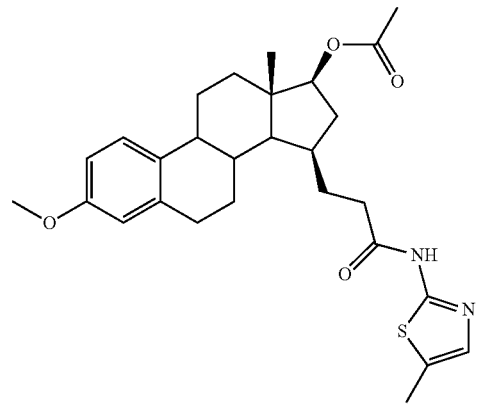 [SMILES: COc1ccc2c(c1)CCC1C2CC[C@@]2(C)C1[C@H](CCC(=O)Nc1ncc(C)s1)C[C@@H]2OC(C)=O] | $^1$H-NMR (DMSO-$d_6$): 0.90 (s, 3H), 1.20-2.38 (m, 23H), 2.80 (m, 2H), 3.69 (s, 3H), 4.60 (t, 1H), 6.65 (m, 2H), 7.11 (s, 1H), 7.18 (d, 1H), 11.90 (s, 1H). |
| 46 | 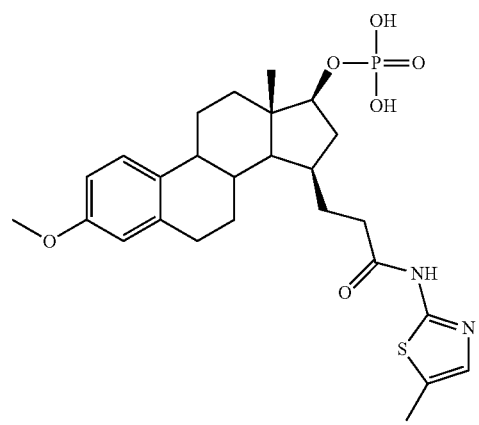 [SMILES: COc1ccc2c(c1)CCC1C2CC[C@@]2(C)C1[C@H](CCC(=O)Nc1ncc(C)s1)C[C@@H]2OP(=O)(O)O] | $^1$H-NMR (DMSO-$d_6$): 0.85 (s, 3H), 1.22-2.30 (m, 19H), 2.79 (m, 2H), 3.68 (s, 3H), 4.07 (m, 1H), 6.65 (m, 2H), 7.10 (s, 1H), 7.15 (d, 1H), 11.91 (s, 1H). |

TABLE 1-continued
| # | Compound | NMR |
|---|---|---|
| 47 | 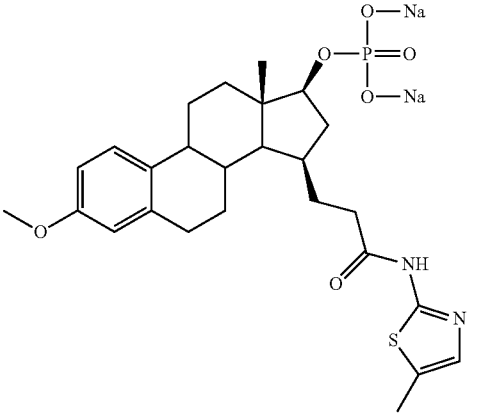 | $^1$H-NMR (D$_2$O): 0.72 (s, 3H), 1.15-2.50 (m, 21H), 3.64 (s, 3H), 3.94 (m, 1H), 6.56 (m, 2H), 7.04 (m, 2H). |
| 48 | 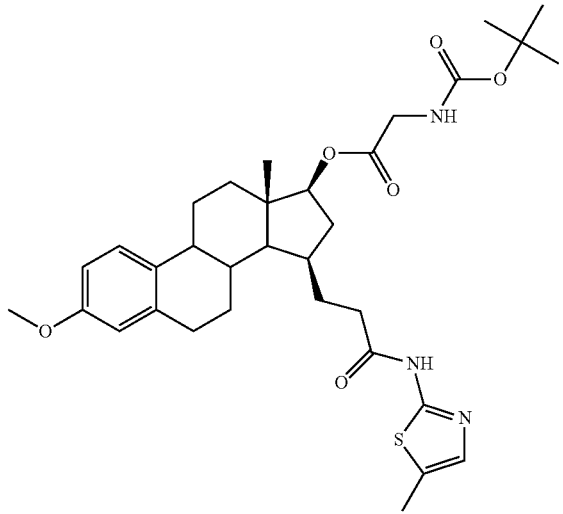 [SMILES: COc1ccc2c(c1)CCC1C2CC[C@@]2(C)C1[C@H](CCC(=O)Nc1ncc(C)s1)C[C@@H]2OC(=O)CNC(=O)OC(C)(C)C] | $^1$H-NMR (DMSO-d$_6$): 0.90 (s, 3H), 1.39 (s, 9H), 1.20-2.35 (m, 19H), 2.81 (m, 2H), 3.65 (m, 2H), 3.69 (s, 3H), 4.65 (t, 1H), 6.66 (m, 2H), 7.10 (s, 1H), 7.23 (d, 1H), 11.90 (s, 1H). |
| 49 | 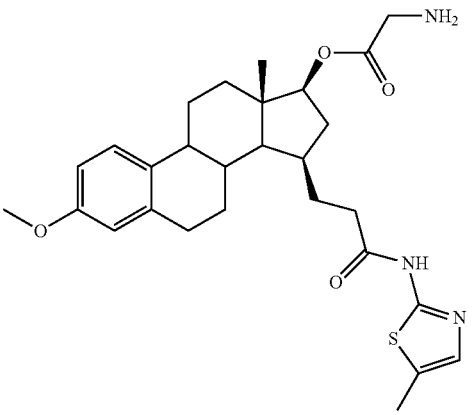 [SMILES: COc1ccc2c(c1)CCC1C2CC[C@@]2(C)C1[C@H](CCC(=O)Nc1ncc(C)s1)C[C@@H]2OC(=O)CN] | $^1$H-NMR (DMSO-d$_6$): 0.94 (s, 3H), 1.20-2.35 (m, 19H), 2.85 (m, 2H), 3.64 (m, 2H), 3.70 (s, 3H), 4.78 (t, 1H), 6.68 (m, 2H), 7.12 (s, 1H), 7.14 (d, 1H), 8.21 (br s, 2H), 11.93 (s, 1H). |

TABLE 1-continued

| # | Compound | NMR |
|---|---|---|
| 50 | | $^1$H-NMR (DMSO-$d_6$): 0.91 (s, 3H), 1.20-2.35 (m, 19H), 2.27 (2 × s, 6H), 2.81 (m, 2H), 3.20 (m, 2H), 3.69 (s, 3H), 4.66 (t, 1H), 6.65 (m, 2H), 7.10 (s, 1H), 7.13 (d, 1H), 11.90 (s, 1H). |
| 51 | | $^1$H-NMR (CDCl$_3$): 1.00 (s, 3H), 1.20-2.60 (m, 19H), 2.87 (m, 2H), 3.02 (s, 3H), 3.78 (s, 3H), 4.55 (t, 1H), 6.68 (m, 2H), 7.06 (s, 1H), 7.18 (d, 1H). |
| 52 | | $^1$H-NMR (DMSO-$d_6$): 0.91 (s, 3H), 1.30-2.40 (m, 25H), 2.83 (m, 2H), 6.82-6.86 (m, 2H), 7.11 (s, 1H), 7.28 (d, 1H), 11.89 (s, 1H). |

TABLE 1-continued

| # | Compound | NMR |
|---|---|---|
| 53 | | $^1$H-NMR (DMSO-d$_6$) 0.82-0.92 (m, 9H) 1.25-2.58 (m, 33H) 2.84 (m, 2H), 4.63 (t 1H), 6.83 (m, 2H) 7.11 (s, 1H), 7.27 (d 1H), 11.89 (s, 1H). |
| 54 | | $^1$H-NMR (DMSO-d$_6$): 0.82-0.92 (m, 9H), 1.10-2.57 (m, 59H), 2.85 (m, 2H), 4.64 (m, 1H), 6.80-6.84 (m, 2H), 7.11 (s, 1H), 7.25-7.29 (m, 1H), 11.90 (s, 1H). |
| 55 | | $^1$H-NMR (DMSO-d$_6$): 0.94 (s, 3H), 1.20-2.50 (m, 22H), 2.88 (m, 2H), 4.63 (t, 1H), 7.00-7.04 (m, 2H), 7.11 (s, 1H), 7.35 (d, 1H), 7.57-7.65 (m, 2H), 7.70-7.79 (m, 1H), 8.10-8.14 (m, 2H), 11.91 (s, 1H). |
| 56 | | $^1$H-NMR (DMSO-d$_6$): 0.91 (s, 3H), 1.10-2.56 (m, 51H), 2.84 (m, 2H), 4.63 (t, 1H), 4.90-5.03 (m, 4H), 5.65-5.90 (m, 2H), 6.80-6.84 (m, 2H), 7.10 (s, 1H), 7.25-7.29 (m, 1H), 11.90 (s, 1H). |

TABLE 1-continued
| # | Compound | NMR |
|---|----------|-----|
| 57 | 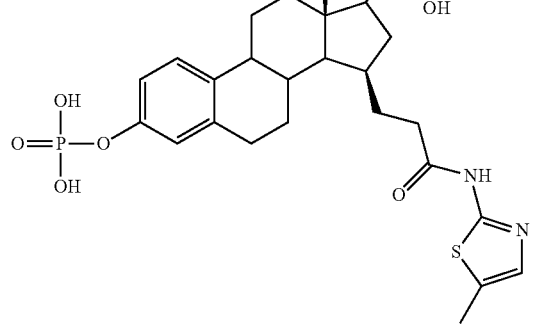 | $^1$H-NMR (DMSO-$d_6$): 0.86 (s, 3H), 1.10-2.80 (m, 21H), 4.10 (m, 1H), 6.87 (m, 2H), 7.10 (s, 1H), 7.22 (d, 1H), 11.93 (s, 1H). |
| 58 | 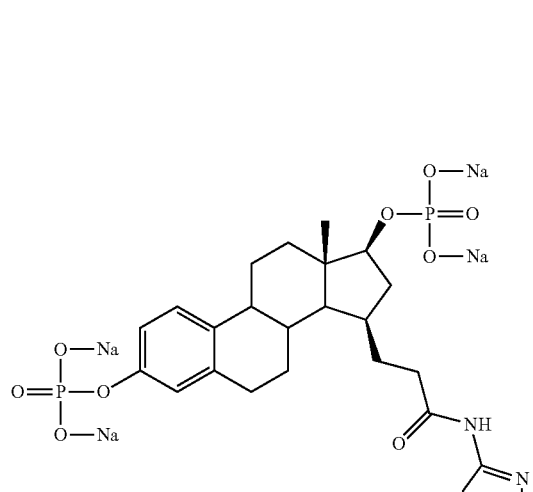 | $^1$H-NMR (DMSO-$d_6$ + $D_2O$): 0.74 (s, 3H), 1.10-2.70 (m, 21H), 3.91 (m, 1H), 6.79 (m, 2H), 6.99 (s, 1H), 7.09 (d, 1H). |
| 59 | 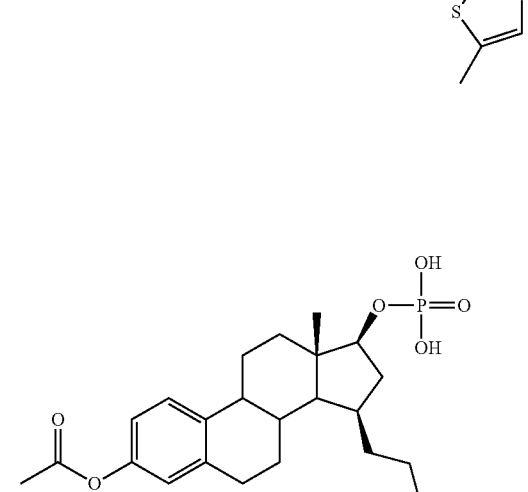 | $^1$H-NMR (DMSO-$d_6$): 0.87 (s, 3H), 1.20-2.50 (m, 24H), 2.83 (m, 2H), 4.06 (m, 1H), 6.82-6.90 (m, 2H), 7.10 (s, 1H), 7.28 (d, 1H), 11.92 (s, 1H). |

TABLE 1-continued
| # | Compound | NMR |
|---|---|---|
| 60 | 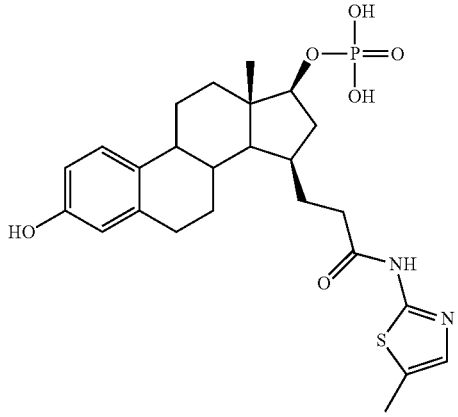 [SMILES: Cc1cnc(NC(=O)CC[C@@H]2C[C@H](OP(=O)(O)O)[C@@]3(C)CCC4c5ccc(O)cc5CCC4C23)s1] | ¹H-NMR (DMSO-d$_6$): 0.85 (s, 3H), 1.20-2.40 (m, 19H), 2.74 (m, 2H), 4.05 (t, 1H), 6.47 (m, 2H), 7.06 (d, 1H), 7.10 (s, 1H), 8.93 (br s, 1H), 11.91 (s, 1H). |
| 61 | 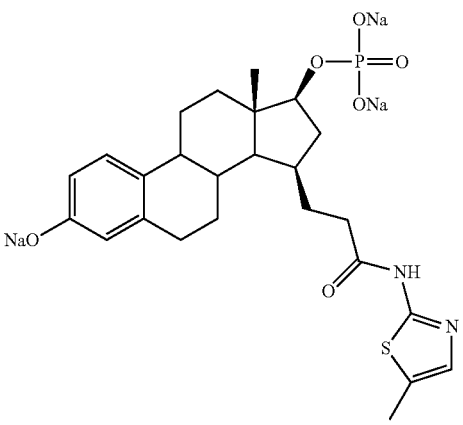 | ¹H-NMR (D$_2$O): 0.80 (s, 3H), 1.15-2.50 (m, 19H), 2.68 (m, 2H), 3.96 (m, 1H), 6.41 (m, 2H), 7.02 (s, 1H), 7.08 (d, 1H). |
| 62 | 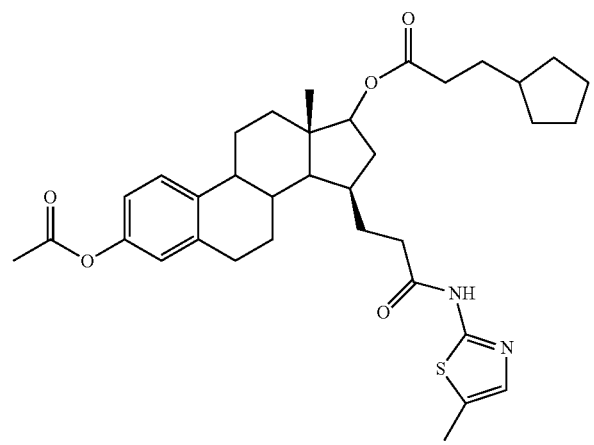 [SMILES: CC(=O)Oc1ccc2c(c1)CCC1C2CC[C@]2(C)C(OC(=O)CCC3CCCC3)C[C@@H](CCC(=O)Nc3ncc(C)s3)C12] | ¹H-NMR (DMSO-d$_6$): 0.91 (s, 3H), 1.00-2.50 (m, 35H), 2.83 (m, 2H), 4.62 (t, 1H), 6.82-6.86 (m, 2H), 7.10 (s, 1H), 7.27 (d, 1H), 11.90 (s, 1H). |

TABLE 1-continued
| # | Compound | NMR |
|---|---|---|
| 63 | 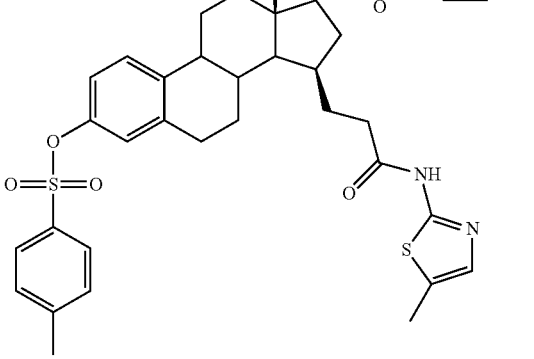 | $^1$H-NMR (DMSO-$d_6$): 0.86 (s, 3H), 1.20-2.50 (m, 27H), 2.74 (m, 2H), 4.31 (t, 1H), 6.68 (m, 2H), 7.10 (s, 1H), 7.19 (d, 1H), 7.47 (m, 4H), 7.78 (m, 4H), 11.86 (s, 1H). |
| 64 | 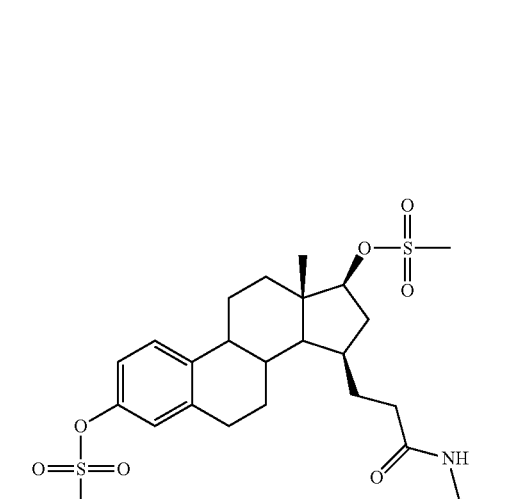 | $^1$H-NMR (DMSO-$d_6$): 0.93 (s, 3H), 1.20-2.50 (m, 27H), 2.88 (m, 2H), 4.54 (t, 1H), 7.09 (m, 3H), 7.38 (d, 1H), 11.92 (s, 1H). |
| 67 | 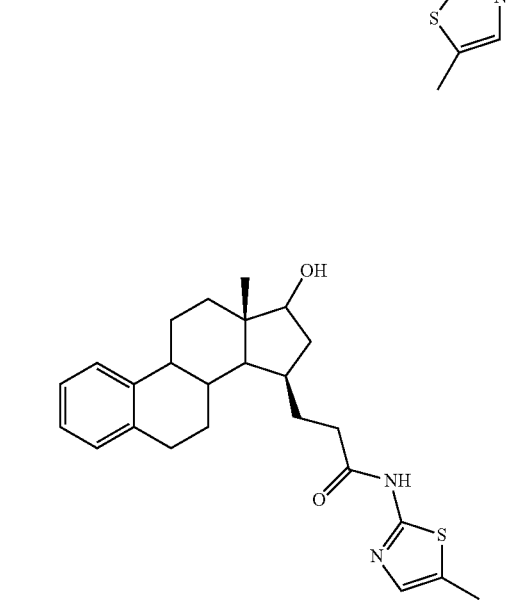 | $^1$H-NMR (CDCl$_3$ + MeOD-$d_4$): 0.90 (s, 3H), 1.2-2.6 (m, 21H), 3.69 (t, 1H), 7.02 (s, 1H), 7.05-7.2 (m, 3H), 7.30 (m, 1H). |

TABLE 1-continued
| # | Compound | NMR |
|---|---|---|
| 68 | 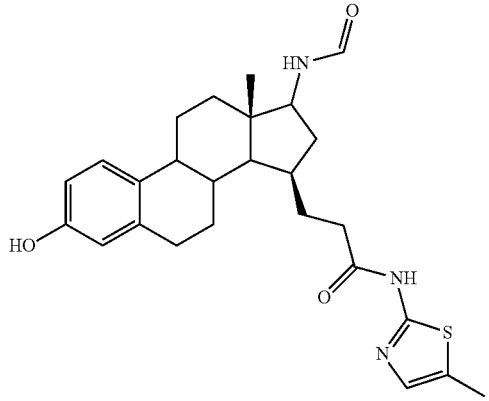 [SMILES: Cc1cnc(NC(=O)CC[C@@H]2CC(NC=O)[C@@]3(C)CCC4c5ccc(O)cc5CCC4C23)s1] | $^1$H-NMR (CDCl$_3$ + MeOH-d$_4$): 0.87 (s, 3H), 1.20-2.50 (m, 21H), 2.7-2.9 (m, 2H), 2.39 (s, 3H), 4.0 (t, 1H), 6.57 (s, 2H), 6.62 (d, 1H), 7.03 (d, 1H), 7.10 (d, 1H), 7.41 (s, 1H), 8.14 (s, 1H), 9.49 (s, 1H), 11.94 (br s, 1H). |
| 71 | 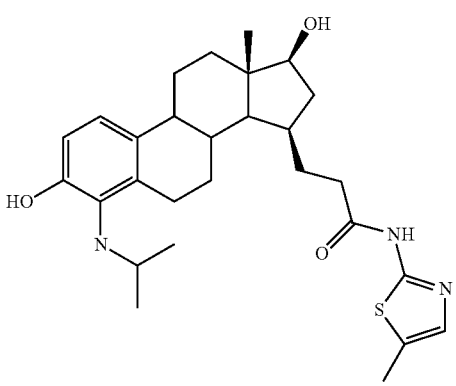 [SMILES: Cc1cnc(NC(=O)CC[C@@H]2C[C@H](O)[C@@]3(C)CCC4c5ccc(O)c(NC(C)C)c5CCC4C23)s1] | $^1$H-NMR (CDCl$_3$): 0.89 (s, 3H), 1.10 & 1.16 (2 × d, 6H), 1.27-1.75 (m, 8H), 1.87-2.30 (m, 14H), 2.76 (m, 2H), 3.25 (m, 1H), 3.72 (t, 1H), 6.74 (d, 1H), 7.0 (d, 1H), 7.06 (s, 1H). |
| 72 | 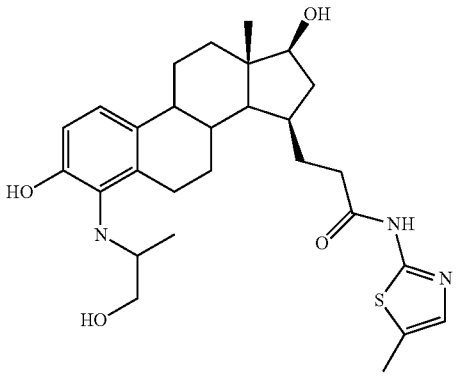 [SMILES: Cc1cnc(NC(=O)CC[C@@H]2C[C@H](O)[C@@]3(C)CCC4c5ccc(O)c(NC(C)CO)c5CCC4C23)s1] | $^1$H-NMR (CDCl$_3$): 1.04 (s, 3H), 1.14 (d, 3H), 1.30-1.92 (m, 8H), 2.10-2.90 (m, 15H), 3.24 (m, 1H), 3.49 (s, 2H), 3.65-3.78 (m, 1H), 6.75 (d, 1H), 6.95 (d, 1H), 7.05 (s, 1H). |
| 73 | 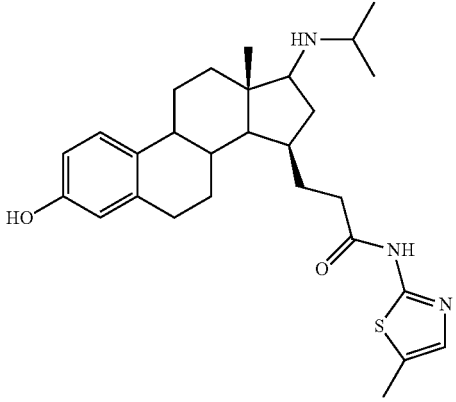 [SMILES: Cc1cnc(NC(=O)CC[C@@H]2CC(NC(C)C)[C@@]3(C)CCC4c5ccc(O)cc5CCC4C23)s1] | $^1$H-NMR (CDCl$_3$ + MeOH-d$_4$): 0.86 (s, 3H), 1.11 (dd, 6H), 1.20-1.65 (m, 11H), 1.85-2.85 (m, 14H), 3.03 (t, 1H), 6.56-6.80 (m, 2H), 7.04-7.10 (m, 2H). |

TABLE 1-continued
| # | Compound | NMR |
|---|---|---|
| 75b | 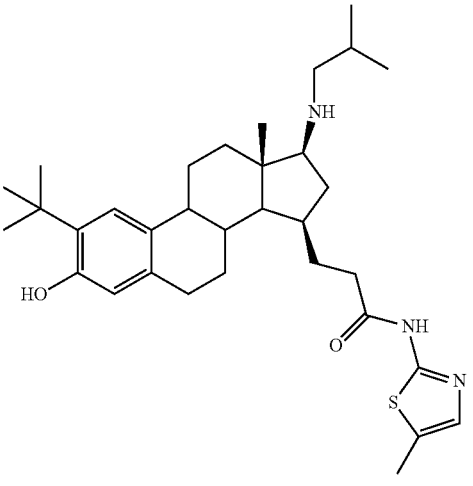 [SMILES: Cc1cnc(NC(=O)CC[C@@H]2C[C@H](NCC(C)C)[C@@]3(C)CCC4c5cc(C(C)(C)C)c(O)cc5CCC4C23)s1] | $^1$H-NMR (CDCl$_3$): 1.06 & 1.09 (2 × s, 6H), 1.37 (s, 9H), 1.54-1.77 (m, 3H), 1.80-3.05 (m, 25H), 6.49 (s, 1H), 7.00 (s, 1H), 7.12 (s, 1H). |
| 76 | 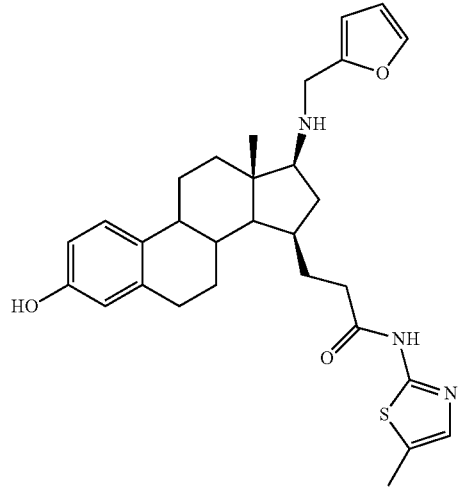 [SMILES: Cc1cnc(NC(=O)CC[C@@H]2C[C@H](NCc3ccco3)[C@@]3(C)CCC4c5ccc(O)cc5CCC4C23)s1] | $^1$H-NMR (CDCl$_3$ + MeOH-d4): 1.04 (s, 3H), 1.35-1.79 (s, 8H), 2.00-2.89 (m, 17H), 4.06 (d, 2H), 6.42 (s, 1H), 6.53-6.63 (m, 3H), 7.05 (s, 1H), 7.47 (s, 1H). |
| 77 | 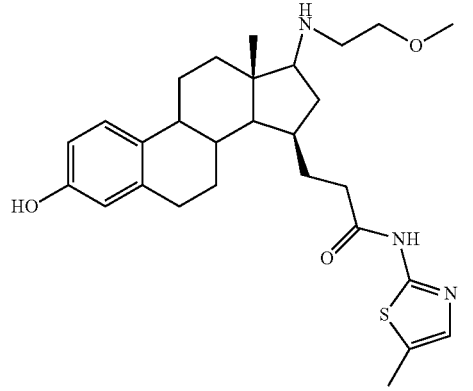 [SMILES: COCCNC1C[C@@H](CCC(=O)Nc2ncc(C)s2)C2C3CCc4cc(O)ccc4C3CC[C@]12C] | $^1$H-NMR (CDCl$_3$): 0.86 (s, 3H), 1.25-1.65 (m, 7H), 1.75-2.86 (m, 17H), 3.34 (s, 4H), 3.51 (m, 2H), 6.54 (s, 1H), 6.59 (d, 1H), 7.04-7.08 (m, 2H). |

TABLE 1-continued
| # | Compound | NMR |
|---|----------|-----|
| 78 | 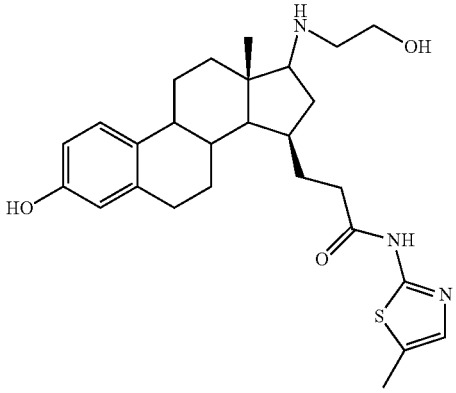 [SMILES: Cc1cnc(NC(=O)CC[C@@H]2CC(NCCO)[C@@]3(C)CCC4c5ccc(O)cc5CCC4C23)s1] | ¹H-NMR (CDCl₃ + MeOH-d4): 0.91 (s, 3H), 1.23-1.61 (m, 8H), 1.95-2.89 (m, 17H), 3.70 (m, 2H), 6.57-6.64 (m, 2H), 7.03 (d, 1H), 7.09 (d, 1H). |
| 79 | 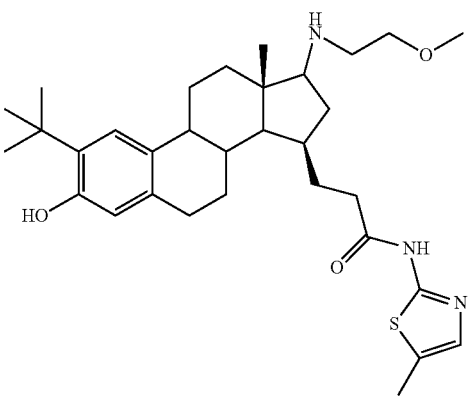 [SMILES: COCCNC1C[C@@H](CCC(=O)Nc2ncc(C)s2)C2C3CCc4cc(O)c(C(C)(C)C)cc4C3CC[C@]12C] | ¹H-NMR (CDCl₃): 0.88 (s, 3H), 1.23-1.62 (m, 17H), 1.94-2.86 (m, 20H), 3.50 (s, 2H), 6.40 (s, 1H), 7.03 (d, 1H), 7.15 (s, 1H). |
| 80 | 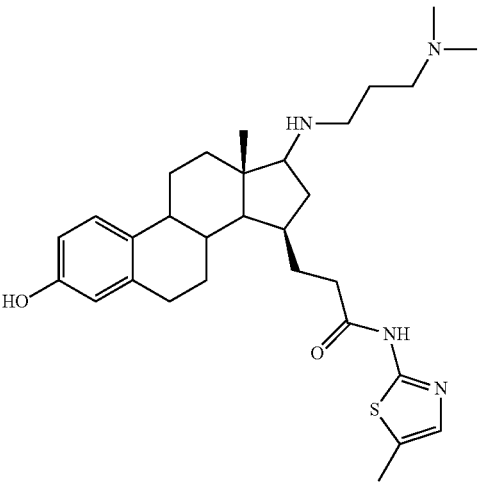 [SMILES: Cc1cnc(NC(=O)CC[C@@H]2CC(NCCCN(C)C)[C@@]3(C)CCC4c5ccc(O)cc5CCC4C23)s1] | ¹H-NMR (CDCl₃): 0.83 (s, 3H), 1.25-2.20 (m, 20H), 2.41 (s, 3H), 2.56 (s, 6H), 2.60-2.84 (m, 6H), 6.54 (s, 1H), 6.60 (d, 1H) 7.05-7.08 (m, 2H). |

| # | Compound | NMR |
|---|---|---|
| 81 | (structure shown) | ¹H-NMR (CDCl₃ + MeOH-d4): 0.82 (s, 3H), 1.18-1.48 (m, 7H), 1.91-2.10 (m, 13H), 2.25 (s, 3H), 2.39 (s, 6H), 2.58-2.77 (m, 4H), 6.53 (s, 1H), 6.58 (d, 1H) 7.04 (s, 1H), 7.06 (m, 1H). |

General Preparation Methods

Compounds of the present invention may be prepared by methods known in the art.

The following examples illustrate the preparation of compounds of formula (I).

General Information

Commercial grade reagents and solvents were used without further purification. Thin-layer chromatography (TLC) was performed on Merck-plates; pre-coated aluminum sheets. Visualization of plates was done the following techniques: 1) ultraviolet illumination (254 nm), 2) dipping the plate into anisaldehyde or vanillin solution followed by heating. 1H-NMR spectra were measured with a Bruker DPX (200 MHz) spectrometer with the solvent as indicated.

Preparation of Synthesis Starting Materials and Precursors

Compound VII may be synthesized as disclosed in Messinger et al. Mol Cell Endocrinol. 2009 (301) 216-224. The detailed synthesis of compound VII starting from estrone has been described in the Solvay Pharmaceuticals' PCT applications WO2005/047303 and WO2006/125800.

Benzyl-C15-C16-dehydroestrone II was prepared in five steps from estrone according to previously described methods. The compound II was treated with an allylic Grignard reagent in the presence of cuprous iodide and lithium chloride in temperature −78° C. Hydroboration by borane tetrahydrofuran complex at room temperature to compound III and following hydrogen peroxide oxidation in alkaline conditions produced diol IV in over 90% yields. Jones oxidation in acetone-water afforded acid V, which was debenzylated by hydrogenation to compound VI by using Pd/C as a catalyst. The final step was the amide formation affording the β-thiazole VII.

The phenolic VII was treated with a suitable acid anhydride or an acid halide and pyridine to C-17 ester VIII.

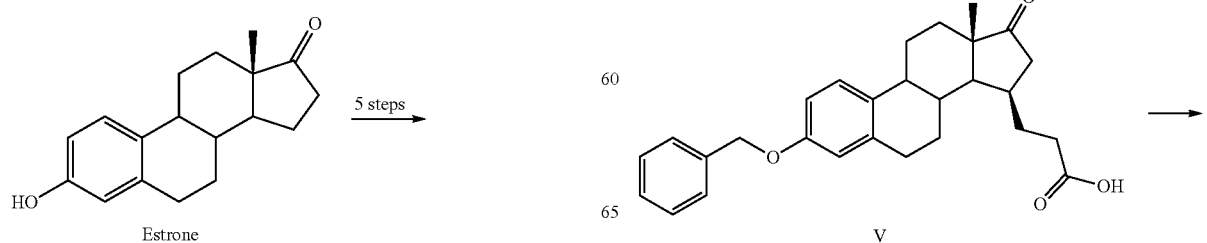

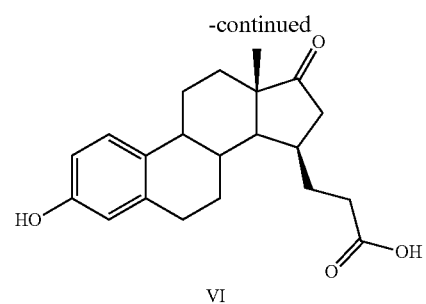

VI

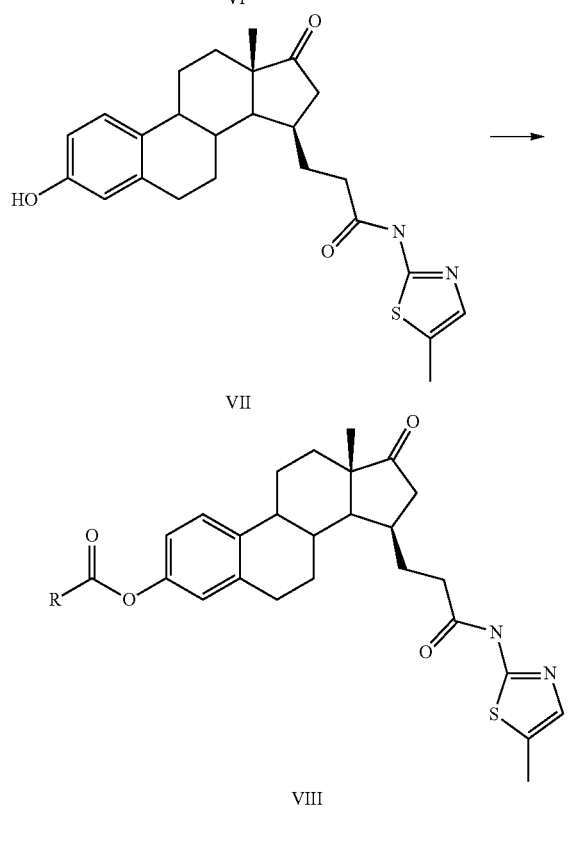

VII

VIII

Compound 1

3-((13S,15R,17S)-3,17-Dihydroxy-13-methyl-7,8,9,
11,12,13,14,15,16,17decahydro-6H-cyclopenta[a]
phenanthren-15-yl)-N-(5-methylthiazol-2-yl)pro-
panamide The compound VII (3.0 g, 100 mol-%) was dissolved in tetrahydrofuran (THF) (75 ml) and water (10.5 ml). NaBH$_4$ (400 mol-%) was added to cooled mixture, stirring was continued at room temperature (rt) for two hours. Saturated NH$_4$Cl-solution (75 ml) was carefully added to the cooled reaction mixture and stirred for an hour. The phases were separated, and the water phase was extracted with EtOAc (3×30 ml). Organic phases were combined and washed finally with brine. The crude precipitate was co-evaporated with toluene. The yield of the product 1 was 2.4 g (78%).

$^1$H-NMR (CDCl$_3$+MeOH-d$_4$): 0.89 (s, 3H), 1.18-2.52 (m, 19H), 2.83 (m, 2H), 3.68 (t, 1H), 6.57-6.65 (m, 2H), 7.03 (d, 1H), 7.11 (d, 1H). MS m/z (TOF ES$^+$): 463 (M+Na).

Compound 2

Acetic acid (13S,15R)-13-methyl-15-[2-(5-methyl-
thiazol-2-ylcarbamoyl)-ethyl]-17-oxo-7,8,9,11,12,
13,14,15,16,17-decahydro-6H-cyclopenta[a]phenan-
thren-3-yl ester

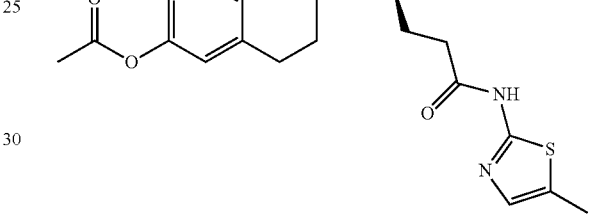

The compound VII (100 mol-%) was dissolved in dichloromethane (DCM) (15 ml). Pyridine (1000 mol-%) and acetic anhydride (500 mol-%) were added. The reaction was refluxed for 1-4 hours followed by TLC. DCM was added and reaction mixture washed with water, 1N HCl, water and brine. The reaction was dried with Na$_2$SO$_4$ and the solvent was evaporated. The crude product was purified by flash chromatography. The yield of the C-3 acetylated 2 was 86%.

$^1$H-NMR (DMSO-d$_6$): 0.98 (s, 3H), 1.35-2.40 (m, 22H), 2.86 (m, 2H), 6.83-6.87 (m, 2H), 7.11 (s, 1H), 7.29 (d, 1H), 11.91 (s, 1H). MS m/z (TOF ES$^+$): 503 (M+Na).

Compound 3

Acetic acid (13S,15R,17S)-17-hydroxyl-13-methyl-
15-[2-(5-methylthiazol-2-ylcarbamoyl)-ethyl]-7,8,9,
11,12,13,14,15,16,17-decahydro-6H-cyclopenta[a]
phenanthren-3-yl ester

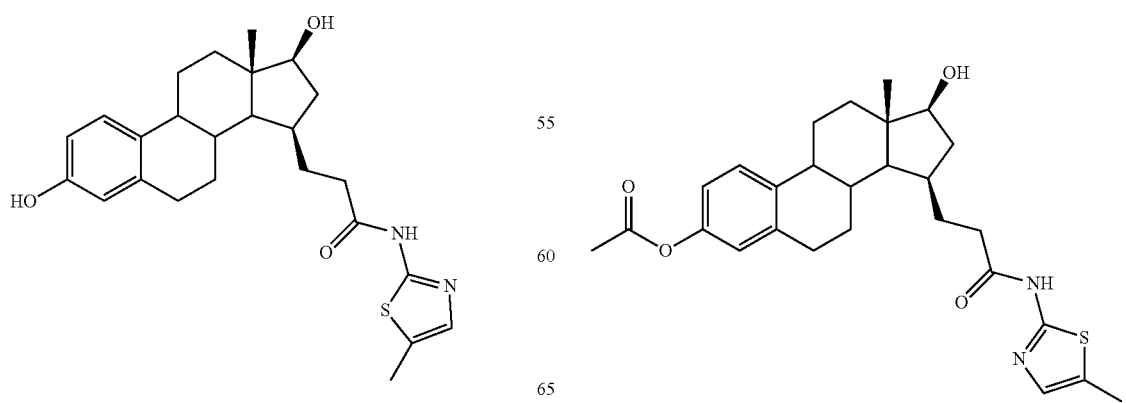

The compound 2 (2.6 g, 5.41 mmol) was dissolved in THF (40 ml) and water (8 ml). Reaction was cooled to 0° C. and NaBH₄ (0.82 g, 21.64 mmol) was added slowly. Reaction mixture was stirred at rt for 45 min. Saturated NH₄Cl (100 ml) was added carefully in to the cold reaction mixture and reaction agitated at rt overnight. Phases were separated and NH₄Cl layer extracted with EtOAc. Combined organic layers were extracted with brine and water and dried with Na₂SO₄. Solvents were evaporated. Crude product (2.6 g) was purified with flash chromatography (eluent: DCM: MeOH 98:2). The yield of the product 3 was 1.2 g (43%).

¹H-NMR (DMSO-d₆): 0.79 (s, 3H), 1.1-2.4 (m, 22H), 2.82 (m, 2H), 4.55 (d, 1H), 6.81 (s, 1H), 6.85 (s, 1H), 7.10 (s, 1H), 7.28 (d, 1H), 11.89 (s, 1H). MS m/z (TOF ES⁺): 505 (M+Na).

Compounds 4 to 6

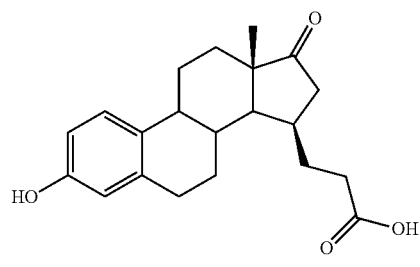

VI

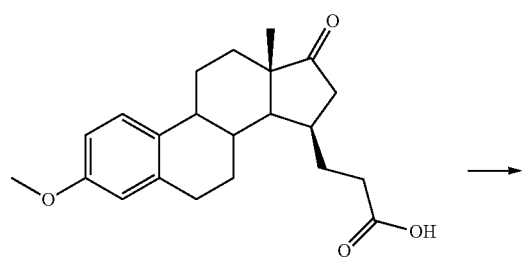

4

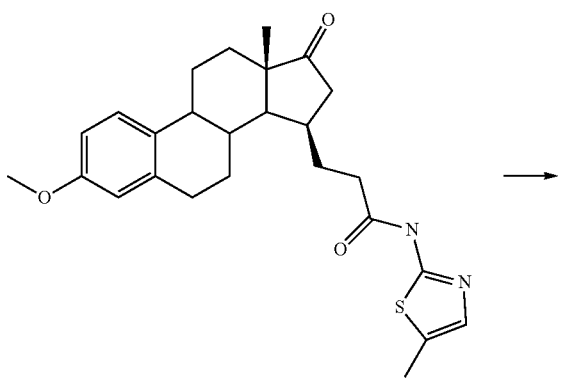

5

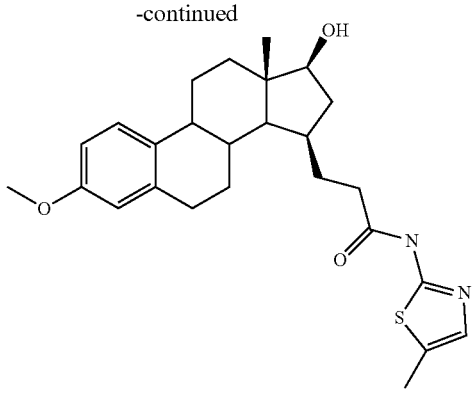

Compound 4

3-((13S,15R)-3-Methoxy-13-methyl-17-oxo-7,8,9,11,12,13,14,15,16,17-decahydro-6H-cyclopenta[a]phenanthren-15-yl)-propionic acid The compound VI (2.0 g, 100 mol-%) was dissolved in acetone (40 ml). Potassium carbonate (200 mol-%) and methyl iodide (500 mol-%) were added and stirred at rt overnight. Additional amounts of methyl iodide (200 mol-%) and potassium carbonate (100 mol-%) were added and refluxed for 10 hours. The solvent was evaporated. The precipitate was dissolved in methanol (50 ml) and 2M NaOH-solution was added until pH was >12. The reaction mixture was stirred at rt for 4 hours. The reaction mixture was acidified by HCl. The product was extracted with DCM (3×30 ml), washed several times with water and finally with brine. The amount of the product 4 was 1.95 g; the yield was 94%.

¹H-NMR (CDCl₃): 1.05 (s, 3H), 1.45-2.48 (m, 19H), 2.93 (m, 2H), 3.79 (s, 3H), 6.70 (m, 2H), 7.20 (d, 1H).

Compound 5

3-((13S,15R)-3-Methoxy-13-methyl-17-oxo-7,8,9,11,12,13,14,15,16,17-decahydro-6H-cyclopenta[a]phenanthren-15-yl)-N-(5-methylthiazol-2-yl)propanamide

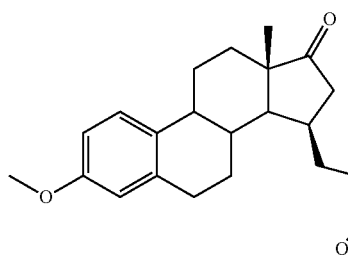
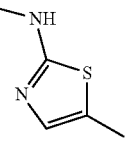

The compound 4 (2.0 g, 100 mol-%) was dissolved in dry DCM (80 ml). 2-Amino-5-methylthiazol (200 mol-%), N-methylmorpholine (NMM) (300 mol-%) ja 1-hydroxy-1H-benzotriazole (HOBT) (170 mol-%) were added. The reaction mixture was stirred for five minutes, cooled to 0 to 5° C. and 1-ethyl-3-(3'dimethylaminopropyl)carbodiimide hydrochloride (EDCl) (220 mol-%) was added. The reaction mixture was stirred at rt overnight and then diluted with DCM, washed with 1N HCl-solution and 5% KOH-solution. The organic phase was finally washed with water and brine. The crude product was purified by chromatography affording 1.85 (73%) of the product 5.

$^1$H-NMR (CDCl$_3$): 1.06 (s, 3H), 1.37-2.60 (m, 22H), 2.90 (m, 2H), 3.79 (s, 3H), 6.70 (m, 2H), 7.05 (s, 1H), 7.19 (d, 1H), 12.11 (s, 1H).

Compound 6

3-((13S,15R,17S)-17-Hydroxy-3-methoxy-13-methyl-7,8,9,11,12,13,14,15,16,17-decahydro-6H-cyclopenta[a]phenanthren-15-yl)-N-(5-methylthiazol-2-yl)propanamide

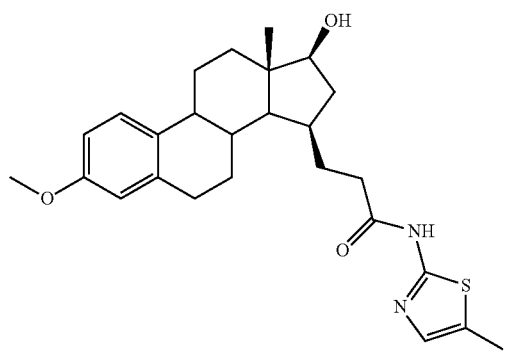

Prepared according to the method described for the compound 1 using the compound 5 as a starting material.

$^1$H-NMR (DMSO-d$_6$): 0.78 (s, 3H), 1.23-2.32 (m, 22H), 2.79 (m, 2H), 3.69 (s, 3H), 4.56 (d, 1H), 6.63 (m, 2H), 7.10 (s, 1H), 7.15 (d, 1H), 11.90 (s, 1H).

Compounds 7 to 11

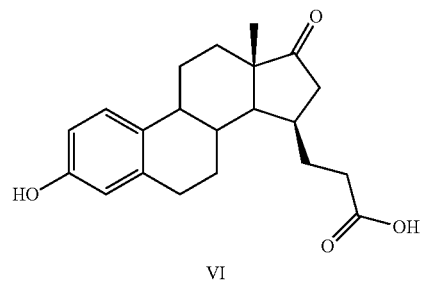

VI

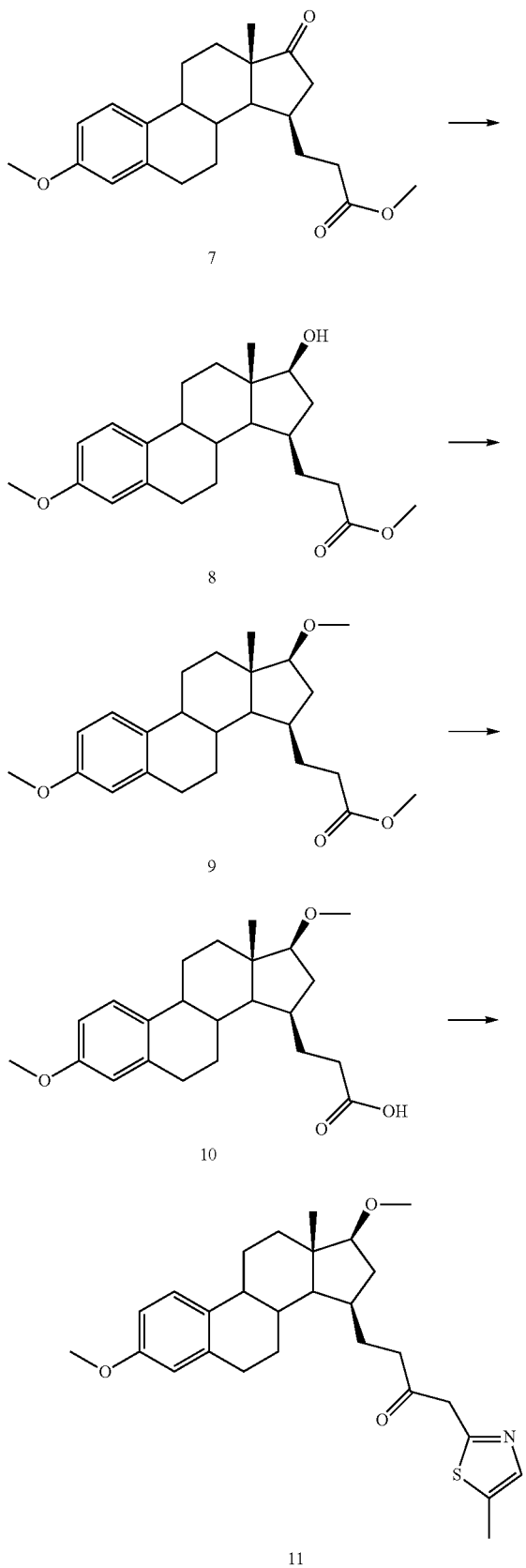

7

8

9

10

11

Compound 7

3-((13S,15R)-3-Methoxy-13-methyl-17-oxo-7,8,9,11,12,13,14,15,16,17-decahydro-6H-cyclopenta[a]phenanthren-15-yl)-propionic acid methyl ester

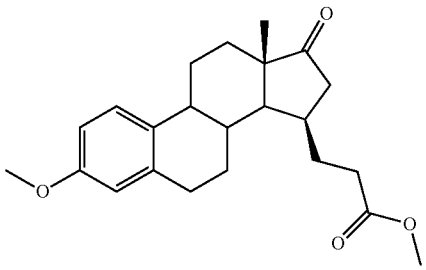

The compound 7 was prepared in 72% yield from the compound VI as a starting material by the method used for 4 without hydrolysis step.

$^1$H-NMR (CDCl$_3$): 1.05 (s, 3H), 1.44-2.40 (m, 19H), 2.93 (m, 2H), 3.70 (s, 3H), 3.79 (s, 3H), 6.70 (m, 2H), 7.20 (d, 1H).

Compound 8

3-((13S,15R,17S)-17-Hydroxy-3-methoxy-13-methyl-7,8,9,11,12,13,14,15,16,17-decahydro-6H-cyclopenta[a]phenanthren-15-yl)-propionic acid methyl ester

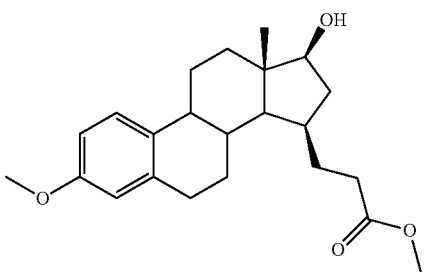

The compound 7 (0.5 g, 100 mol-%) was dissolved in THF (13 ml) and water (1.75 ml). NaBH$_4$ (400 mol-%) was added to cooled mixture, stirring was continued at rt for two hours. Saturated NH$_4$Cl-solution (15 ml) was carefully added to the cooled reaction mixture and stirred for an hour. The phases were separated, the water phase was extracted with EtOAc (3×30 ml). Organic phases were combined and washed with brine. The crude precipitate was co-evaporated with toluene.

$^1$H-NMR (DMSO-d$_6$): 0.76 (s, 3H), 1.18-2.32 (m, 19H), 2.80 (m, 2H), 3.58 (s, 3H), 3.69 (s, 3H), 4.54 (d, 1H), 6.65 (m, 2H), 7.13 (s, 1H). MS m/z (TOF ES$^+$): 395 (M+Na).

Compound 9

3-((13S,15R,17S)-3,17-Dimethoxy-13-methyl-7,8,9,11,12,13,14,15,16,17-decahydro-6H-cyclopenta[a]phenanthren-15-yl)-propionic acid methyl ester

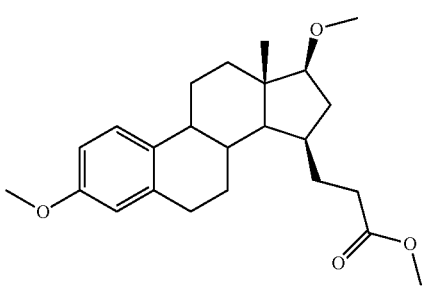

The compound 8 (250 mg, 100 mol-%) was dissolved in dry DMF (5 ml). NaH (250 mol-%) was added and stirred at rt for 30 minutes. Methyl iodide was added (1000 mol-%) and stirred at rt until the reaction was completed. The reaction mixture was poured into dilute 1N HCl-solution. The product 9 was extracted with EtOAc, which was washed with water and brine.

$^1$H-NMR (DMSO-d$_6$): 0.80 (s, 3H), 1.22-2.33 (m, 19H), 2.78 (m, 2H), 3.21 (t, 1H), 3.25 (s, 3H), 3.57 (s, 3H), 3.68 (s, 3H), 6.65 (m, 2H), 7.12 (s, 1H). MS m/z (TOF ES$^+$): 409 (M+Na).

Compound 10

3-((13S,15R,17S)-3,17-Dimethoxy-13-methyl-7,8,9,11,12,13,14,15,16,17-decahydro-6H-cyclopenta[a]phenanthren-15-yl)-propionic acid

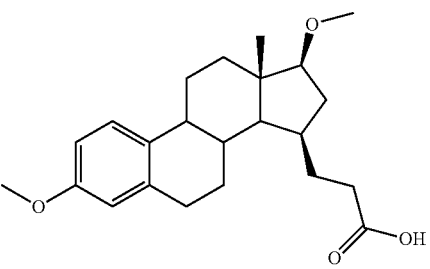 [SMILES: COc1ccc2c(c1)CCC1C2CC[C@@]2(C)C1[C@H](CCC(=O)O)C[C@@H]2OC]

The compound 9 was dissolved in methanol (2 ml) and 2 M KOH-solution was added until pH was 12. The reaction mixture was stirred at rt for 5 hours. The reaction mixture was acidified by HCl. The product 10 was extracted with DCM (3×30 ml), washed several times with water and finally with brine.

$^1$H-NMR (CDCl$_3$): 0.91 (s, 3H), 1.25-2.50 (m, 19H), 2.88 (m, 2H), 3.31 (t, 1H), 3.39 (s, 3H), 3.78 (s, 3H), 6.67 (m, 2H), 7.19 (d, 1H). MS m/z (TOF ES$^+$): 395 (M+Na).

Compound 11
3-((13S,15R,17S)-3,17-Dimethoxy-13-methyl-7,8,9,11,12,13,14,15,16,17-decahydro-6H-cyclopenta[a]phenanthren-15-yl)-N-(5-methylthiazol-2-yl)propanamide
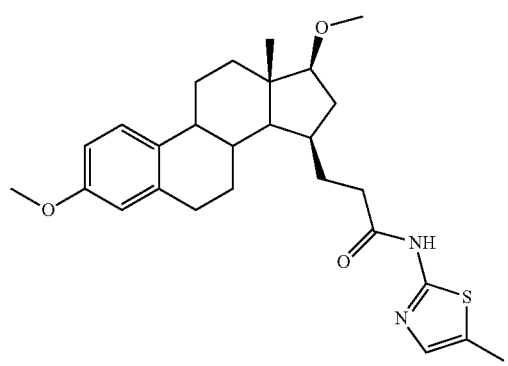
The compound 11 was prepared from the compound 10 as a starting material by the method used for the compound 5.
$^1$H-NMR (DMSO-d$_6$): 0.83 (s, 3H), 1.18-2.32 (m, 22H), 2.79 (m, 2H), 3.21 (t, 1H), 3.27 (s, 3H), 3.69 (s, 3H), 6.64 (m, 2H), 7.10 (s, 1H), 7.12 (d, 1H), 11.89 (s, 1H). MS m/z (TOF ES$^+$): 469 (M+1).
Compounds 12 to 18
C-17 O-alkylation
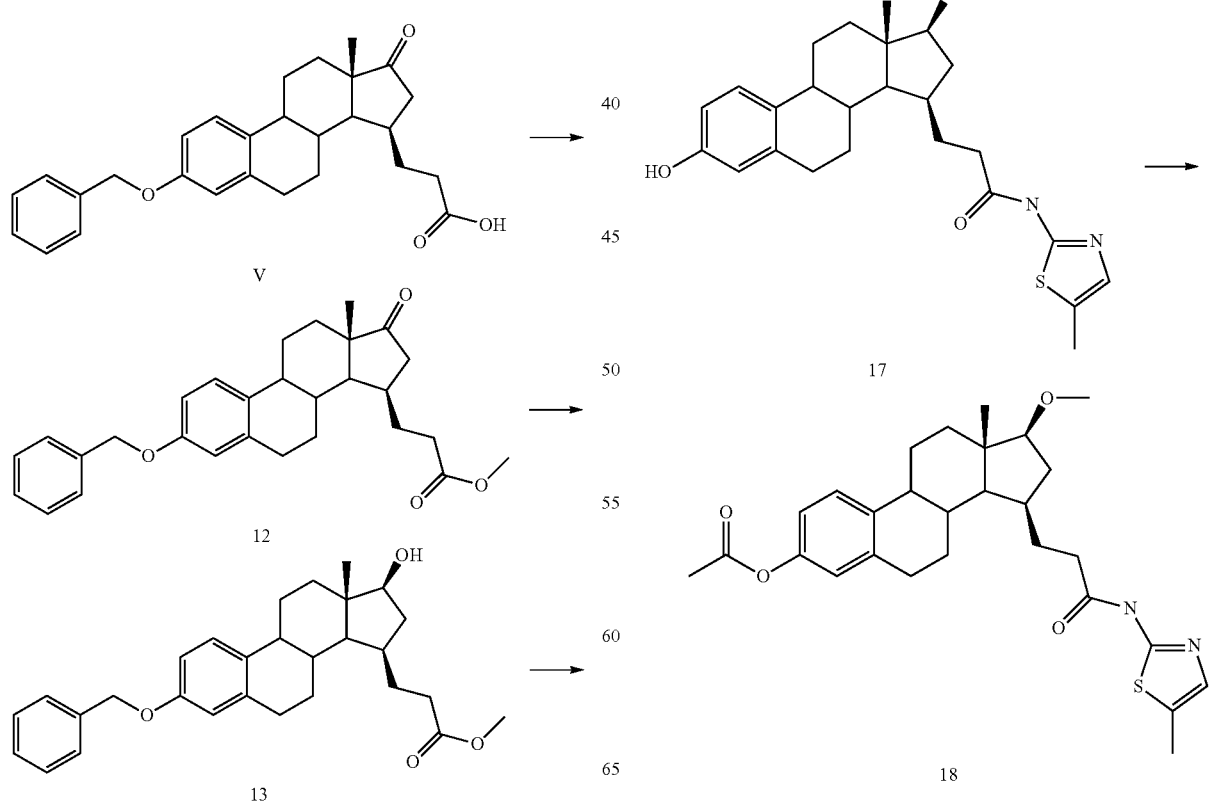
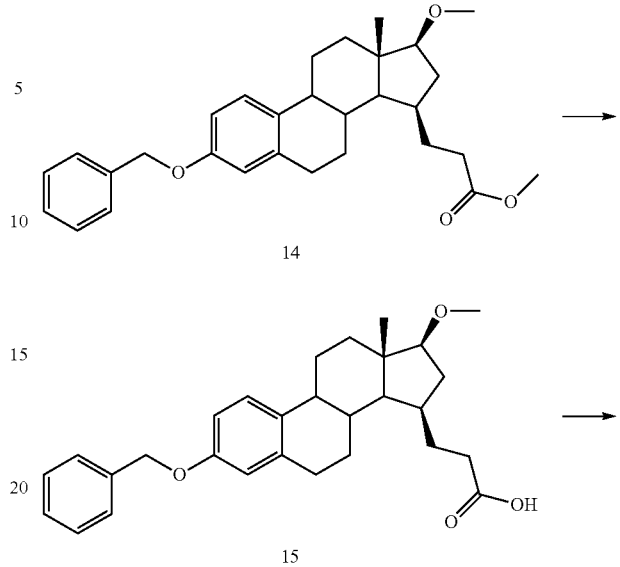

Compound 12

Methyl 3-((13S,15R)-3-(benzyloxy)-13-methyl-17-oxo-7,8,9,11,12,13,14,15,16,17-decahydro-6H-cyclopenta[a]phenanthren-15-yl)propanoate

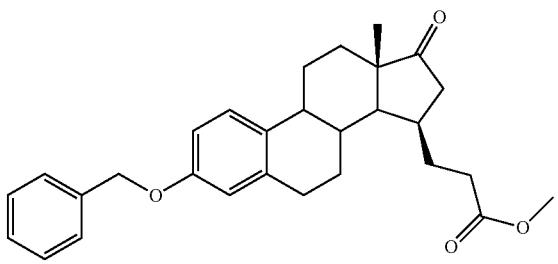 [SMILES: COC(=O)CC[C@@H]1CC(=O)[C@@]2(C)CCC3c4ccc(OCc5ccccc5)cc4CCC3C12]

Iodomethane (2.7 g, 500 mol-%) was added to suspension of the compound V (2.0 g, 100, mol-%) and $K_2OC_3$ (0.5 g, 100 mol-%) in dry acetone (40 ml) under nitrogen atmosphere. The reaction was refluxed for 3.5 h and then stirred overnight at rt. The solvents were evaporated and EtOAc was added. The organic phase was washed with water and brine, dried over $Na_2SO_4$ and evaporated to give a crude product which was purified by column chromatography. The yield of the product 12 was 1.80 g (quant.).

$^1$H-NMR (DMSO-$d_6$): 0.94 (s, 3H), 1.21-2.55 (m, 16H), 3.60 (s, 3H), 5.04 (s, 2H), 6.67-6.85 (m, 2H), 7.16 (d, 1H), 7.28-7.50 (m, 5H); MS m/z (TOF ES+): 496 (M+Na).

Compound 13

Methyl 3-((13S,15R,17S)-3-(benzyloxy)-17-hydroxy-13-methyl-7,8,9,11,12,13,14,15,16,17-decahydro-6H-cyclopenta[a]phenanthren-15-yl)propanoate

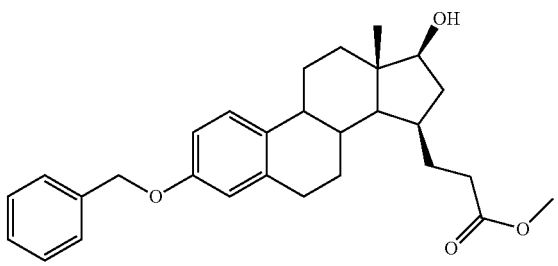 [SMILES: COC(=O)CC[C@@H]1C[C@H](O)[C@@]2(C)CCC3c4ccc(OCc5ccccc5)cc4CCC3C12]

The compound 12 (1.8 g, 100 mol-%) was dissolved in of THF (10 ml) and water (2 ml). The mixture was cooled to 0° C. and $NaBH_4$ (0.6 g, 400 mol-%) was added slowly to reaction. The reaction mixture was stirred 3.5 h at rt. Saturated $NH_4Cl$-solution (60 ml) was added to cold reaction mixture and stirring was continued overnight. The phases were separated and aqueous phase was extracted with EtOAc. The combined organic phases were washed with water and brine, dried over $Na_2SO_4$ and evaporated to give oil which was treated with heptane/DCM/EtOAc to give crystalline solid. Yield of the product 13 was 1.70 g (97%).

$^1$H-NMR (DMSO-$d_6$): 0.76 (s, 3H), 1.05-2.40 (m, 17H), 2.70-2.87 (m, 2H), 3.58 (s, 3H), 4.54 (d, 1H), 5.04 (s, 2H), 6.67-6.80 (m, 2H), 7.15 (d, 1H), 7.28-7.50 (m, 5H); MS m/z (TOF ES+): 471 (M+Na).

Compound 14

Methyl 3-((13S,15R,17S)-3-(benzyloxy)-17-methoxy-13-methyl-7,8,9,11,12,13,14,15,16,17-decahydro-6H-cyclopenta[a]phenanthren-15-yl)propanoate

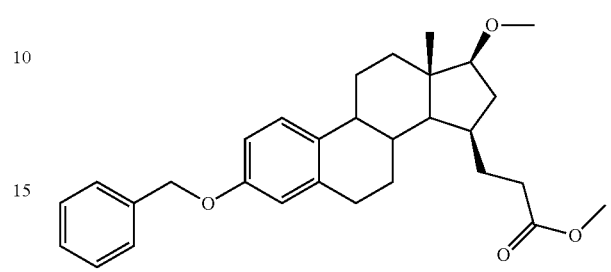

Iodomethane (4.0 g, 900 mol-%) was added to suspension of the compound 13 (1.4 g, 100 mol-%) and sodium hydride (50% dispersion, 0.5 g, 340 mol-%) in dry dimethylformamide (DMF) (30 ml). The reaction was stirred overnight and 1N HCl (10 ml) was added to the reaction. The aqueous phase was extracted with DCM and evaporated. EtOAc was added to the residue. The organic phase was washed with brine and water, dried over $Na_2SO_4$. The crude product was purified by column chromatography. The yield of the compound 14 was 0.9 g (63%).

$^1$H-NMR (DMSO-$d_6$+few drops of MeOH-$d_4$): 0.81 (s, 3H), 1.00-2.51 (m, 16H), 2.78 (m, 2H), 3.25 (m, 1H), 3.26 (s, 3H), 3.58 (s, 3H), 5.04 (s, 2H), 6.72 (m, 2H), 7.12-7.44 (m, 6H). MS m/z (TOF ES+): 485 (M+Na).

Compound 15

3-((13S,15R,17S)-3-(benzyloxy)-17-methoxy-13-methyl-7,8,9,11,12,13,14,15,16,17-decahydro-6H-cyclopenta[a]phenanthren-15-yl)propanoic acid

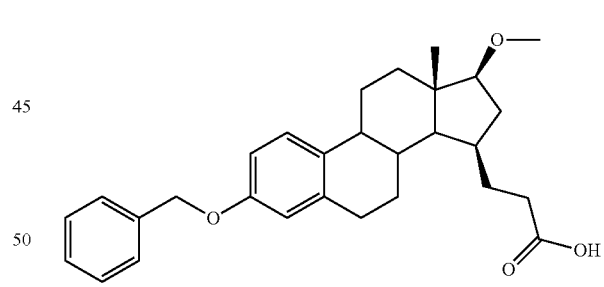

2 M NaOH (5 ml) was added to suspension of the compound 14 (0.9 g, 1.95 mmol) in methanol (30 ml) and THF (15 ml), and stirred overnight at rt. The reaction mixture was acidified with 2 N HCl and the solvents were removed under reduced pressure. Water was added, and the product was extracted with EtOAc. The combined organic layers were washed with water and brine and dried with $Na_2SO_4$. The solvent was evaporated and the precipitate was purified by column chromatography. The yield of the compound 15 was 0.6 g (69%).

$^1$H-NMR (DMSO-$d_6$): 0.82 (s, 3H), 1.11-2.36 (m, 17H), 2.75-2.87 (m, 2H), 3.27 (s, 3H), 5.05 (s, 2H), 6.70-6.80 (m, 2H), 7.10-7.45 (m, 6H), 12.06 (br, 1H); MS m/z (TOF ES+): 471 (M+Na).

Compound 16

3-((13S,15R,17S)-3-hydroxy-17-methoxy-13-methyl-7,8,9,11,12,13,14,15,16,17-decahydro-6H-cyclopenta[a]phenanthren-15-yl)propanoic acid

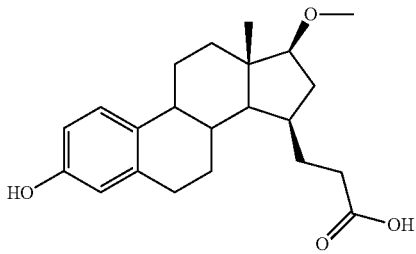 [SMILES: CO[C@H]1C[C@@H](CCC(=O)O)C2C3CCc4cc(O)ccc4C3CC[C@@]21C]

Pd/C (0.1 g, 20 w-%) was added to a solution of the compound 15 (0.5 g, 1.11 mmol) in THF. The mixture was stirred under $H_2$ atmosphere for 5 h before catalyst was filtered off, and solvents were evaporated. EtOAc was added to the residue and extracted with KOH-solution (5%, 3×10 ml). The combined aqueous layers were acidified with 2 N HCl. The aqueous layers were extracted with EtOAc (3×10 ml). The combined organic layers were washed with water (3×10 ml) and brine (3×10 ml), dried with $Na_2SO_4$, and the solvents were evaporated under reduced pressure. The yield of the compound 15 was 0.2 g (50%).

$^1$H-NMR (DMSO-$d_6$): 0.80 (s, 3H), 1.11-2.34 (m, 17H), 2.68-2.75 (m, 2H), 3.26 (s, 3H), 6.40-6.55 (m, 2H), 7.02 (d, 1H), 8.99 (br, 1H), 11.99 (br, 1H); MS m/z (TOF ES-F): 381 (M+Na).

Compound 17

3-((13S,15R,17S)-3-hydroxy-17-methoxy-13-methyl-7,8,9,11,12,13,14,15,16,17-decahydro-6H-cyclopenta[a]phenanthren-15-yl)-N-(5-methylthiazol-2-yl)propanamide

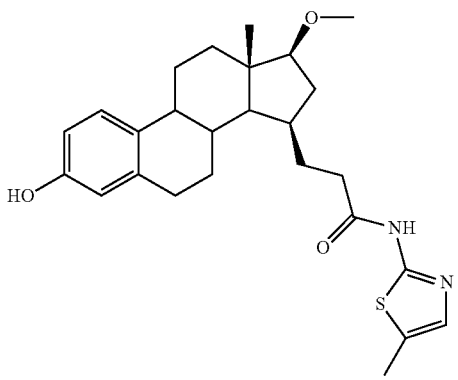

2-Amino-5-methylthiazole (110 mg, 200 mol-%), NMM (150 mg, 300 mol-%) and HOBT (130 mg, 170 mol-%) was added to suspension of the compound 16 (180 mg, 100 mol-%) in DCM. The reaction mixture was stirred 5 min at rt and EDCl (220 mol-%) was added at 0° C. The reaction mixture was stirred overnight at rt. DCM was added and organic layer was washed with 1 N HCl (3×10 ml), water (3×10 ml) and brine (10 ml). The solvents were evaporated. The crude product was purified by column chromatography. The yield of the thiazole 17 was 0.1 g (44%).

$^1$H-NMR (DMSO-$d_6$): 0.84 (s, 3H), 1.10-2.60 (m, 20H), 2.73 (m, 2H), 3.28 (s, 3H), 6.45-6.48 (m, 2H), 7.03 (d, 1H), 7.11 (s, 1H), 9.02 (s, 1H), 11.90 (s, 1H). MS m/z (TOF ES+): 477 (M+Na).

Compound 18

(13S,15R,17S)-17-methoxy-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate

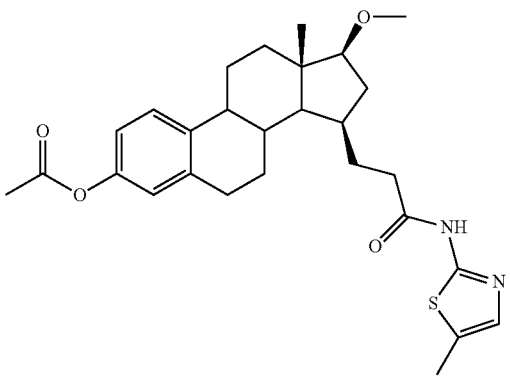 [SMILES: CO[C@H]1C[C@@H](CCC(=O)Nc2ncc(C)s2)C2C3CCc4cc(OC(C)=O)ccc4C3CC[C@@]21C]

Acetic anhydride (34 mg, 500 mol-%) and pyridine (26 mg, 500 mol-%) was added to the solution of the compound 17 (30 mg, 100 mol-%) in DCM (3 ml). The reaction mixture was stirred 3 h at rt. The organic layer was washed with water, 1 N HCl and water and dried with $Na_2SO_4$. The solvents were evaporated. The precipitate was purified by column chromatography. The yield of the compound 18 was 20 mg (61%).

$^1$H-NMR (CDCl$_3$): 0.91 (s, 3H), 1.10-2.70 (m, 22H), 2.85 (m, 2H), 3.30 (t, 1H), 3.38 (s, 3H), 6.80-6.86 (m, 2H), 7.06 (s, 1H), 7.26 (d, 1H), 11.91 (s, 1H). MS m/z (TOF ES+): 519 (M+Na).

Compound 19

3-((13S,15R,17S)-17-butyl-3,17-dihydroxy-13-methyl-7,8,9,11,12,13,14,15,16,17-decahydro-6H-cyclopenta[a]phenanthren-15-yl)-N-(5-methylthiazol-2-yl)propanamide

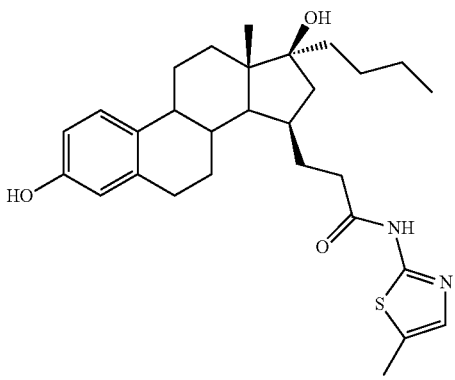 [SMILES: CCCC[C@]1(O)C[C@@H](CCC(=O)Nc2ncc(C)s2)C2C3CCc4cc(O)ccc4C3CC[C@@]21C]

The compound VII (200 mg, 100 mol-%) was dissolved in dry THF (4 ml), and the reaction mixture was cooled to 0° C. n-BuLi (300 mol-%, 2.5 M solution in THF) was added dropwise to the reaction mixture under nitrogen atmosphere. After stirring at 0° C. for two hours, stirring was continued at rt overnight. The reaction mixture was poured into water (10 ml), neutralized with 2 N HCl-solution. The product was extracted with EtOAc (3×10 ml). The organic phase was washed with saturated NaHCO$_3$ (3×10 ml) and brine (3×10 ml). After drying with Na$_2$SO$_4$, the solvent was evaporated. The crude product 19 was purified by chromatography using DCM-EtOAc as an eluent (gradient 9:1->1:1).

$^1$H-NMR (DMSO-d$_6$): 0.88 (m, 6H), 1.14-2.30 (m, 22H), 2.33 (s, 3H), 2.73 (m, 2H), 3.88 (s, 1H), 6.47 (m, 2H), 7.02 (d, 1H), 7.11 (s, 1H), 9.00 (s, 1H), 11.89 (s, 1H). MS m/z (TOF ES$^+$): 519 (M+Na).

Compound 20

3-((13S,15R,17S)-17-butyl-17-hydroxy-3-methoxy-13-methyl-7,8,9,11,12,13,14,15,16,17-decahydro-6H-cyclopenta[a]phenanthren-15-yl)-N-(5-methyl-thiazol-2-yl)propanamide

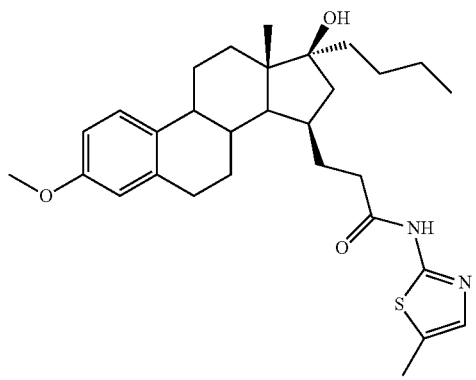 [SMILES: CCCC[C@]1(O)C[C@@H](CCC(=O)Nc2ncc(C)s2)C2C3CCc4cc(OC)ccc4C3CC[C@@]21C]

Synthesis procedure like for the compound 19 using the compound 5 as a starting material and n-BuLi as 1.6 M solution in hexane.

$^1$H-NMR (CDCl$_3$): 0.94-1.05 (m, 6H), 1.25-2.52 (m, 25H), 2.85 (m, 2H), 3.78 (s, 3H), 6.64-6.75 (m, 2H), 7.07 (s, 1H), 7.19 (d, 1H), 11.66 (br s, 1H). MS m/z (TOF ES$^+$): 511 (M+1).

Compound 21

3-((13S,15R,17S)-17-cyano-3,17-dihydroxy-13-methyl-7,8,9,11,12,13,14,15,16,17-decahydro-6H-cyclopenta[a]phenanthren-15-yl)-N-(5-methylthi-azol-2-yl)propanamide

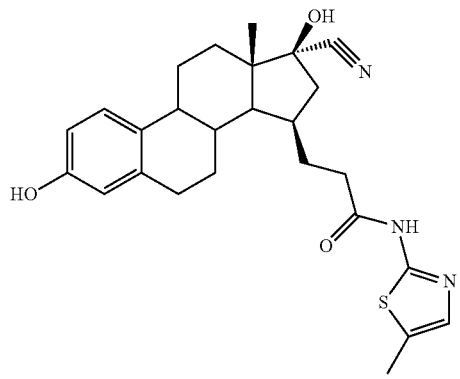 [SMILES: Cc1cnc(NC(=O)CC[C@@H]2C[C@@](O)(C#N)[C@@]3(C)CCC4c5ccc(O)cc5CCC4C23)s1]

The acetylated compound 2 (50 mg, 100 mol-%) and KCN (1200 mol-%) were dissolved in a mixture of methanol (1 ml) and acetic acid (250 µl). The reaction was stirred rt for three weeks. Ice-water was added to the reaction mixture (5 ml). The solid material formed was filtered and washed several times with water. The product was dissolved in EtOAc, washed with water and brine. After drying with Na$_2$SO$_4$ the solvent was evaporated. The product 21 was purified by chromatography using DCM-methanol as an eluent (gradient: 10:0.1->4:1). The C-3 acetylated compound 22 was isolated as a by-product.

$^1$H-NMR (CDCl$_3$): 0.97 (s, 3H), 1.38-2.60 (m, 16H), 2.29 (s, 3H), 2.41 (s, 3H), 2.71-2.90 (m, 3H), 6.84 (m, 2H), 7.03 (s, 1H), 7.24 (d, 1H). MS m/z (TOF ES-F): 508 (M+1).

Compound 22

(13S,15R,17S)-17-cyano-17-hydroxy-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate

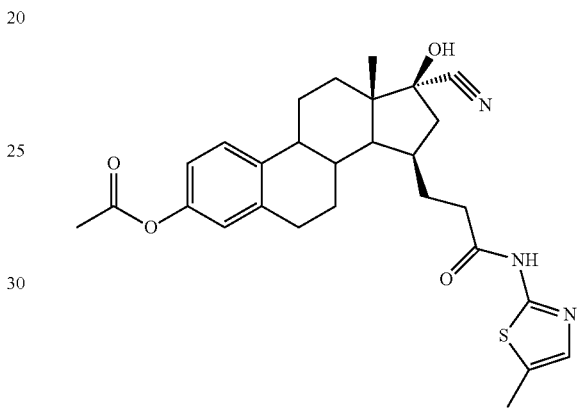

$^1$H-NMR (CDCl$_3$+MeOH-d4): 0.97 (s, 3H), 1.30-2.80 (m, 21H), 6.57-6.65 (m, 2H), 7.04 (s, 1H), 7.09 (d, 1H). MS m/z (TOF ES-F): 466 (M+1).

Compound 23

3-((13S,15R,17S)-17-cyano-17-hydroxy-3-methoxy-13-methyl-7,8,9,11,12,13,14,15,16,17-decahydro-6H-cyclopenta[a]phenanthren-15-yl)-N-(5-methyl-thiazol-2-yl)propanamide

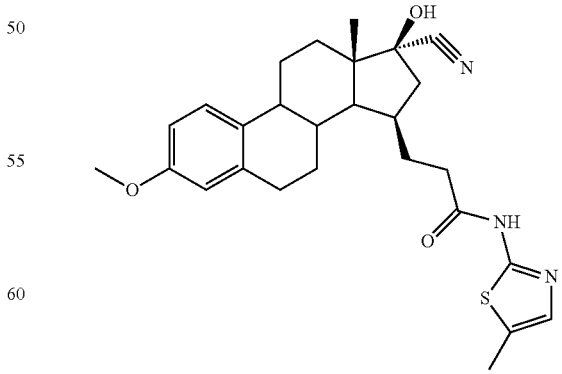

The compound 23 was prepared according to method used for the compound 21 using the compound 5 as a starting material.

¹H-NMR (CDCl₃): 1.01 (s, 3H), 1.40-2.90 (m, 21H), 3.77 (s, 3H), 6.63-6.73 (m, 2H), 7.03 (s, 1H), 7.18 (d, 1H). MS m/z (TOF ES+): 502 (M+Na), 480 (M+1).

Compound 24

3-((13S,15R,17R)-17-(cyanomethyl)-3,17-dihydroxy-13-methyl-7,8,9,11,12,13,14,15,16,17-decahydro-6H-cyclopenta[a]phenanthren-15-yl)-N-(5-methylthiazol-2-yl)propanamide

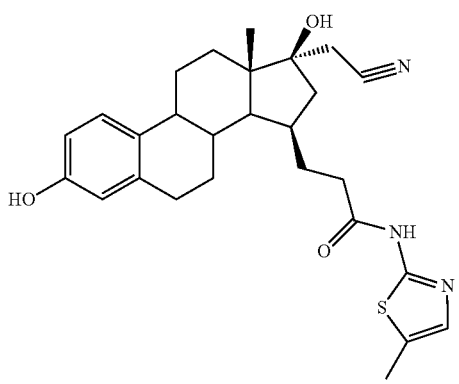 [SMILES: Cc1cnc(NC(=O)CC[C@@H]2C[C@@](O)(CC#N)[C@@]3(C)CCC4c5ccc(O)cc5CCC4C23)s1]

Dry THF (15 ml) was cooled to −60° C., and n-BuLi (500 mol-%) was added under nitrogen atmosphere. Dry acetonitrile (1000 mol-%) in dry THF (2.5 ml) was added. Stirring was continued in cold for 30 minutes. The compound VII (1.0 g, 100 mol-%) dissolved in THF (20 ml) was added dropwise to the reaction mixture, followed by stirring at −60° C. for 30 minutes. Stirring was continued at rt overnight. Saturated ammonium chloride solution (25 ml) was added carefully and stirred for 15 minutes. Then water (25 ml) was added and the product was extracted with EtOAc (3×30 ml), washed with water (3×30 ml) and finally with brine (3×30 ml). The crude product was dried with Na₂SO₄ and the solvent was evaporated. The product 24 was purified by chromatography.

¹H-NMR (DMSO-d₆): 0.90 (s, 3H), 1.15-2.84 (m, 23H), 4.99 (s, 1H), 6.46-6.52 (m, 2H), 7.01-7.11 (m, 2H), 9.01 (s, 1H), 11.93 (s, 1H). MS m/z (TOF ES+): 502 (M+Na), 480 (M+1).

Compound 25

3-((13S,15R,17R)-17-(cyanomethyl)-17-hydroxy-3-methoxy-13-methyl-7,8,9,11,12,13,14,15,16,17-decahydro-6H-cyclopenta[a]phenanthren-15-yl)-N-(5-methylthiazol-2-yl)propanamide

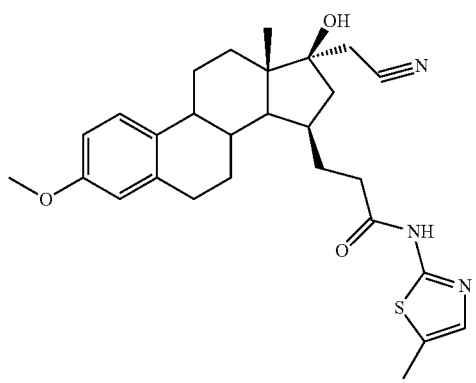 [SMILES: COc1ccc2c(c1)CCC1C2CC[C@@]2(C)C1[C@H](CCC(=O)Nc1ncc(C)s1)C[C@@]2(O)CC#N]

The compound 25 was prepared according to method used for the compound 24 using the compound 5 as a starting material.

¹H-NMR (DMSO-d₆): 0.90 (s, 3H), 1.20-2.84 (m, 23H), 3.69 (s, 3H), 4.99 (s, 1H), 6.63-6.68 (m, 2H), 7.12-7.17 (m, 2H), 11.94 (s, 1H). MS m/z (TOF ES+): 516 (M+Na), 494 (M+1).

Compound 26

3-((13S,15R,17R)-17-(2-amino-2-oxoethyl)-3,17-dihydroxy-13-methyl-7,8,9,11,12,13,14,15,16,17-decahydro-6H-cyclopenta[a]phenanthren-15-yl)-N-(5-methylthiazol-2-yl)propanamide

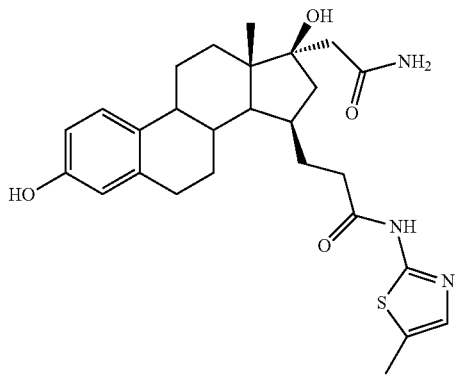 [SMILES: Cc1cnc(NC(=O)CC[C@@H]2C[C@@](O)(CC(N)=O)[C@@]3(C)CCC4c5ccc(O)cc5CCC4C23)s1]

NaOH-solution (6M, 1.2 ml) and TBAB (40 mol-%) were added to the solution of the compound 24 (100 mg, 100 mol-%) in DCM (5 ml). Hydrogen peroxide (30%-solution, 3.0 ml) was added dropwise, and stirred at rt overnight. Water (5 ml) was added, the organic phase was separated. The water phase was acidified to pH 3 with dilute HCl-solution. The precipitated product was filtered. The crude product was purified by flash-chromatography using DCM:MeOH 98:2 as an eluent.

¹H-NMR (DMSO-d₆): 0.91 (s, 3H), 1.15-2.84 (m, 22H), 5.66 (br s, 1H), 6.46 (m, 2H), 7.05 (d, 1H), 7.11 (s, 1H), 7.23 (br s, 1H), 7.61 (br s, 1H), 9.03 (br s, 1H), 11.91 (s, 1H). MS m/z (TOF ES+): 520 (M+Na).

Compound 27

3-((13S,15R)-2,4-dibromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

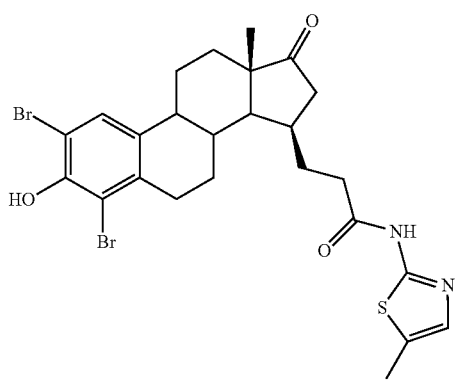 [SMILES: Cc1cnc(NC(=O)CC[C@@H]2CC(=O)[C@@]3(C)CCC4c5cc(Br)c(O)c(Br)c5CCC4C23)s1]

The compound VII (1.0 g, 2.3 mmol) was dissolved in DCM (13 ml), the mixture was cooled to 8° C. and N-bromosuccinimide (NBS) (1.0 g, 5.6 mmol) was added. Reaction mixture was let to warm to rt and stirring was continued for 2.5 h. Water was added and precipitated product was filtered, yielding 1.2 g of crystalline material 27.

$^1$H-NMR (DMSO-$d_6$): 0.95 (s, 3H), 1.22-2.32 (m, 19H), 2.79 (m, 2H), 7.12 (s, 1H), 7.40 (s, 1H), 9.55 (s, 1H), 11.92 (s, 1H). MS m/z (TOF ES$^+$): 617/619/621 (M+Na).

Compound 28

3-((13S,15R,17S)-2,4-dibromo-3,17-dihydroxy-13-methyl-7,8,9,11,12,13,14,15,16,17-decahydro-6H-cyclopenta[a]phenanthren-15-yl)-N-(5-methylthiazol-2-yl)propanamide

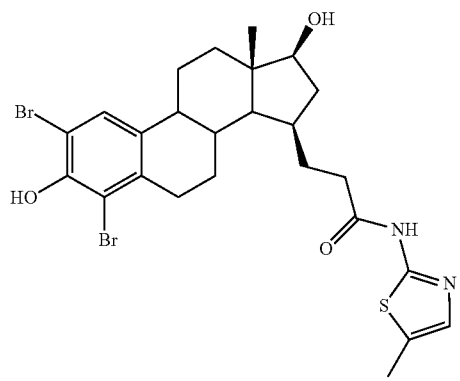 [SMILES: Cc1cnc(NC(=O)CC[C@@H]2C[C@H](O)[C@@]3(C)CCC4c5cc(Br)c(O)c(Br)c5CCC4C23)s1]

The compound 27 (200 mg, 0.335 mmol, 100 mol-%) was dissolved in THF (5 ml) and water (0.7 ml). The mixture was cooled to 0° C. and NaBH$_4$ (51 mg, 1.34 mmol, 400 mol-%) was added slowly to reaction. The reaction mixture was stirred overnight at rt. Saturated NH$_4$Cl-solution (10 ml) was added to cold reaction mixture and stirring was continued overnight. The phases were separated and aqueous phase was extracted with EtOAc (3×15 ml). The combined organic phases were washed with water (3×10 ml) and brine (3×20 ml), dried over Na$_2$SO$_4$ and evaporated. Crude product was triturated with abs. ethanol. The yield of the compound 28 was 102 mg (51%).

$^1$H-NMR (DMSO-$d_6$): 0.76 (s, 3H), 1.06-1.50 (m, 8H), 1.65-1.95 (m, 3H), 2.05-2.90 (m, 10H), 3.45-3.60 (m, 1H), 4.56 (d, 1H), 7.10 (s, 1H), 7.39 (s, 1H), 9.52 (s, 1H), 11.90 (s, 1H). MS m/z (TOF ES$^+$): 599 (M+1)

Compound 29

3-((13S,15R,17S)-2,4-dibromo-3-hydroxy-17-methoxy-13-methyl-7,8,9,11,12,13,14,15,16,17-decahydro-6H-cyclopenta[a]phenanthren-15-yl)-N-(5-methylthiazol-2-yl)propanamide

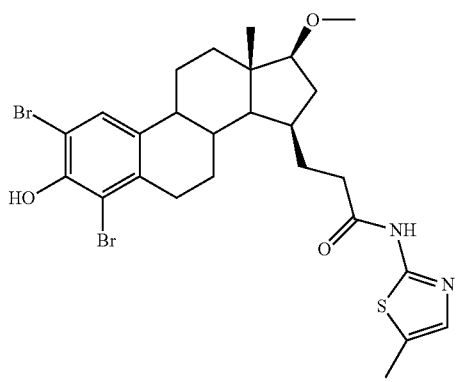 [SMILES: CO[C@H]1C[C@@H](CCC(=O)Nc2ncc(C)s2)C2C3CCc4c(cc(Br)c(O)c4Br)C3CC[C@@]21C]

The compound 29 was prepared using the same method as for the compound 27 using the compound 17 as a starting material.

$^1$H-NMR (CDCl$_3$+MeOH-$d_4$): 0.91 (s, 3H), 1.3-1.7 (m, 7H), 2.0-2.9 (m, 14H), 3.40 (s, 3H), 7.02 (s, 1H), 7.38 (s, 1H). MS m/z (TOF ES$^+$): 633/635/637 (M+Na)

Compound 30

3-((13S,15R,17R)-2,4-dibromo-17-(cyanomethyl)-3,17-dihydroxy-13-methyl-7,8,9,11,12,13,14,15,16,17-decahydro-6H-cyclopenta[a]phenanthren-15-yl)-N-(5-methylthiazol-2-yl)propanamide

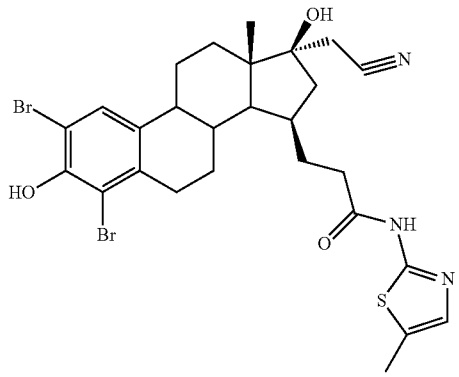 [SMILES: Cc1cnc(NC(=O)CC[C@@H]2C[C@@](O)(CC#N)[C@@]3(C)CCC4c5cc(Br)c(O)c(Br)c5CCC4C23)s1]

The compound 30 was prepared according to method used for the compound 27 using the compound 24 as a starting material.

$^1$H-NMR (DMSO-$d_6$): 0.88 (s, 3H), 1.15-2.84 (m, 23H), 5.00 (s, 1H), 7.11 (s, 1H), 7.38 (s, 1H), 9.54 (br s, 1H), 11.93 (s, 1H). MS m/z (TOF ES$^+$): 658/660/662 (M+Na).

Compound 31

3-((13S,15R,17S)-2,4-dibromo-17-butyl-3,17-dihydroxy-13-methyl-7,8,9,11,12,13,14,15,16,17-decahydro-6H-cyclopenta[a]phenanthren-15-yl)-N-(5-methylthiazol-2-yl)propanamide

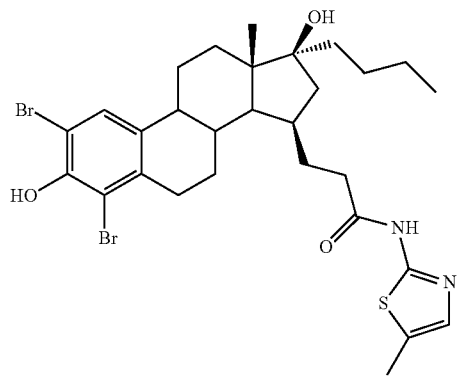 [SMILES: CCCC[C@]1(O)C[C@@H](CCC(=O)Nc2ncc(C)s2)C2C3CCc4c(cc(Br)c(O)c4Br)C3CC[C@@]21C]

The compound 31 was prepared according to method used for the compound 27 using the compound 19 as a starting material.

$^1$H-NMR (CDCl$_3$): 0.91 (t, 3H), 0.99 (s, 3H), 1.30-2.81 (m, 27H), 7.06 (s, 1H), 7.38 (s, 1H). MS m/z (TOF ES$^+$): 675/677/679 (M+Na).

THP-Protection of the C-3 Position

Compound 32

3-[(13S,15R)-13-Methyl-17-oxo-3-(tetrahydropyran-2-yloxy)-7,8,9,11,12,13,14,15,16,17-decahydro-6H-cyclopenta[a]phenanthren-15-yl]-N-(5-methylthiazol-2-yl)propanamide

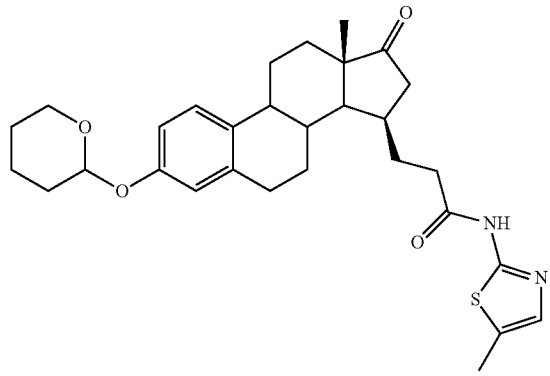 [SMILES: Cc1cnc(NC(=O)CC[C@@H]2CC(=O)[C@@]3(C)CCC4c5ccc(OC6CCCCO6)cc5CCC4C23)s1]

The compound VII (2.0 g, 4.56 mmol) was partly dissolved in 3,4-dihydro-2H-pyran (5 ml, 54.8 mmol) in nitrogen atmosphere using heating (60° C.). p-Toluenesulfonic acid (86 mg, 0.456 mmol) was added. Additional amount of 3,4-dihydro-2H-pyran (7.2 ml, 78.9 mmol) was added at 60-70° C. until the starting material was dissolved. Reaction was finished right after the starting material was dissolved (~30 min). DCM was added to the reaction mixture and washed with half brine, 5% aqueous KOH and water and dried with Na$_2$SO$_4$. Solvent was evaporated. The crude product was crystallized from heptane by trituration. The yield of the product 32 was 2.1 g (88%).

$^1$H-NMR (DMSO-d$_6$): 0.97 (s, 3H), 1.35-2.50 (m, 22H), 2.84 (m, 2H), 3.54 (m), 3.75 (m), 5.40 (s, 1H), 6.74 (m, 2H), 7.11 (s, 1H), 7.16 (d, 1H), 11.91 (s, 1H). MS m/z (TOF ES$^+$): 545 (M+Na).

Compound 33

3-((13S,15R,17S)-17-hydroxy-13-methyl-3-((tetrahydro-2H-pyran-2-yl)oxy)-7,8,9,11,12,13,14,15,16,17-decahydro-6H-cyclopenta[a]phenanthren-15-yl)-N-(5-methylthiazol-2-yl)propanamide

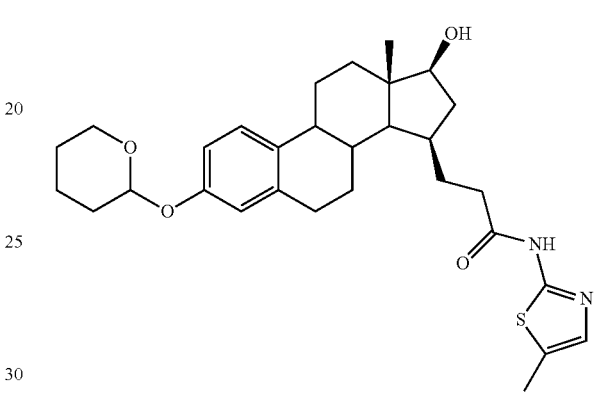

Prepared according to the method described for the compound 1 using the compound 32 as a starting material.

$^1$H-NMR (DMSO-d$_6$): 0.78 (s, 3H), 1.23-2.32 (m, 22H), 2.78 (m, 2H), 3.50 and 3.74 (2×m), 3.69 (s, 3H), 4.55 (d, 1H), 5.39 (s, 1H), 6.75 (m, 2H), 7.10 (s, 1H), 7.17 (d, 1H), 11.88 (s, 1H). MS m/z (TOF ES$^+$): 547 (M+Na).

Compound 34

3-((13S,15R)-3-Benzyloxy-13-methyl-17-oxo-7,8,9,11,12,13,14,15,16,17-decahydro-6H-cyclopenta[a]phenanthren-15-yl)-N-(5-methylthiazol-2-yl)propanamide

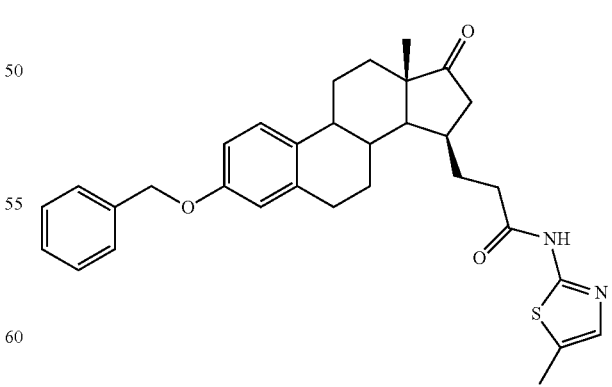

The compound V (2.0 g, 100 mol-%) was dissolved in DCM (80 ml). 2-Amino-5-methylthiazol (200 mol-%), NMM (300 mol-%) and HOBT (170 mol-%) were added to the reaction mixture and stirred for five minutes. The reaction mixture was cooled to 0-5° C. EDCl (220 mol-%) was added and stirred at rt overnight. The reaction mixture was diluted with DCM, washed several times with 1N HCl-solution and brine, and finally with 5% KOH-solution. The organic phase was washed with water and brine. The product 34 was triturated with ethanol-water (8:2).

¹H-NMR (DMSO-d$_6$): 0.97 (s, 3H), 1.37-2.50 (m, 19H), 2.85 (m, 2H), 5.06 (s, 2H), 6.74 (m, 2H), 7.11 (d, 1H), 7.16 (d, 1H), 11.92 (s, 1H). MS m/z (TOF ES$^+$): 551 (M+Na).

Compound 35

3-((13S,15R,17S)-3-(benzyloxy)-17-hydroxy-13-methyl-7,8,9,11,12,13,14,15,16,17-decahydro-6H-cyclopenta[a]phenanthren-15-yl)-N-(5-methylthiazol-2-yl)propanamide

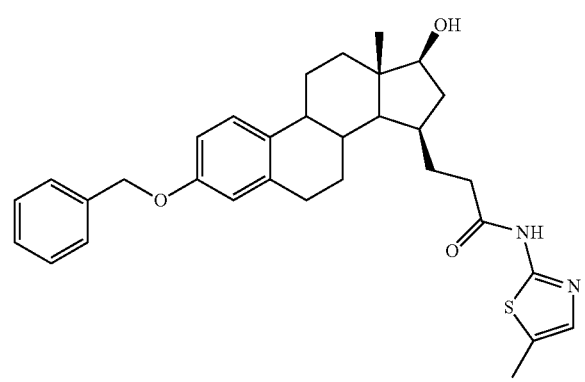 [SMILES: Cc1cnc(NC(=O)CC[C@@H]2C[C@H](O)[C@@]3(C)CCC4c5ccc(OCc6ccccc6)cc5CCC4C23)s1]

Prepared according to the method described for the compound 1 using the compound 34 as a starting material.

¹H-NMR (CDCl$_3$): 0.89 (s, 3H), 1.16-2.60 (m, 19H), 2.85 (m, 2H), 3.71 (t, 1H), 5.02 (s, 2H), 6.74 (m, 2H), 7.05 (d, 1H), 7.15-7.46 (m, 5H).

Method for the Deprotection of Benzylic Protection Group by Using TMSI

The benzylated compound was treated with iodotrimethylsilane (TMSI) in the presence of N-methylimidazole and thiourea, described in detail for the compound VII from the compound 34.

Compound VII from the Compound 34

The compound 34 (100 mg, 100 mol-%), N-methylimidazole (200 mol-%) and thiourea (250 mol-%) were dissolved in dry acetonitrile (2 ml). The reaction mixture was cooled with ice-bath under nitrogen atmosphere. TMSI (700 mol-%) was added slowly dropwise to the reaction mixture, and stirred overnight in dark. After cooling with ice-bath, water (1 ml) was added dropwise. Sat. NaHCO$_3$ was added carefully, followed by addition of EtOAc (10 ml). The organic phase was washed with 5% KOH-solution (3×10 ml). The KOH-phases were combined and acidified with HCl. The product VII was extracted with DCM, which was washed with water and finally with brine.

¹H-NMR (DMSO-d$_6$): 0.95 (s, 3H), 1.21-2.40 (m, 19H), 2.75 (m, 2H), 6.49 (m, 2H), 7.04 (d, 1H), 7.10 (s, 1H), 9.04 (s, 1H), 11.91 (s, 1H). MS m/z (TOF ES$^+$): 462 (M+Na).

General Method for the C-3 Deprotection of the THP-Protection

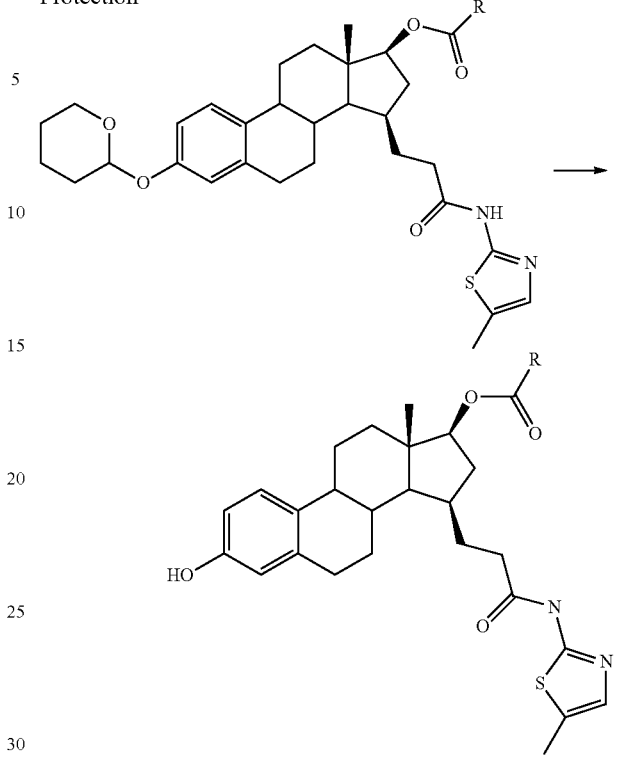

C-3 THP-protected compound (0.5 mmol) was dissolved in ethanol (10 ml) and solution was made mildly acidic with 1.5 N HCl. Reaction was stirred at rt overnight. Ethanol was evaporated, water added and extracted with DCM. DCM phase was extracted with brine and water and dried with Na$_2$SO$_4$. Solvent was evaporated. Crude product was purified with flash chromatography.

Compound 36

Acetic acid (13S,15R,17S)-3-hydroxy-13-methyl-15-[2-(5-methyl-thiazol-2-ylcarbamoyl)-ethyl]-17-oxo-7,8,9,11,12,13,14,15,16,17-decahydro-6H-cyclopenta[a]phenanthren-17-yl ester

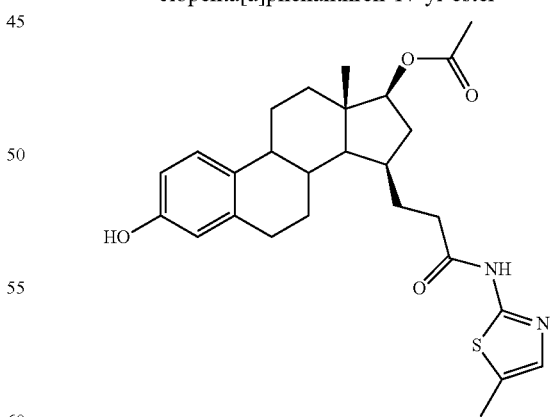

Prepared from the compound 33 using the general esterification method followed by the deprotection method for THP described above.

¹H-NMR (DMSO-d$_6$): 0.89 (s, 3H), 1.20-2.37 (m, 22H), 2.74 (m, 2H), 4.59 (t, 1H), 6.48 (m, 2H), 7.02 (d, 1H), 7.10 (s, 1H), 9.04 (s, 1H), 11.89 (s, 1H). MS m/z (TOF ES$^+$): 505 (M+Na).

Compound 37

(13S,15R,17S)-3-(benzyloxy)-13-methyl-15-(3-((5-methylthiazol-2-yl)amino)-3-oxopropyl)-7,8,9,11,12,13,14,15,16,17-decahydro-6H-cyclopenta[a]phenanthren-17-yl pentanoate

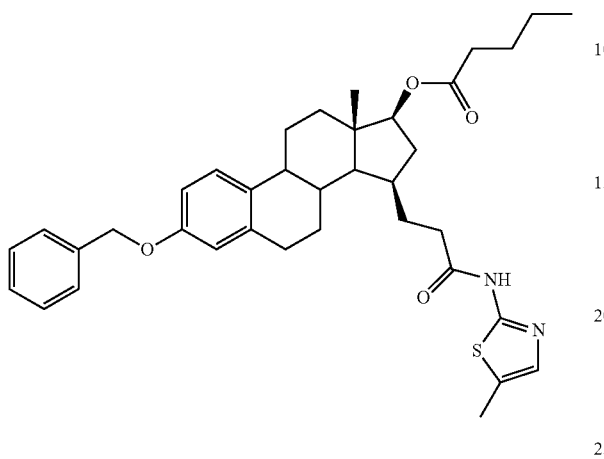

Prepared according to the general esterification method using valeroyl chloride as a reagent and the compound 35 as a starting material.

$^1$H-NMR (CDCl$_3$): 0.93 (t, 3H), 0.96 (s, 3H), 1.34-2.59 (m, 25H), 2.87 (m, 2H), 4.72 (t, 3H), 5.03 (s, 2H), 6.73 (s, 1H), 6.78 (m, 1H), 6.98 (s, 1H), 7.18 (d, 1H), 7.41 (m, 5H). MS m/z (TOF ES$^+$): 637 (M+Na).

Compound 38

Pentanoic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester

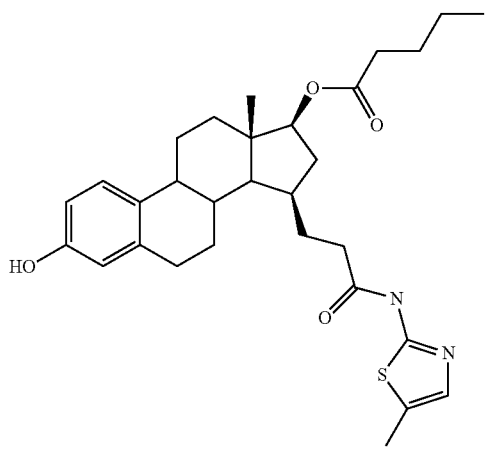 [SMILES: CCCCC(=O)O[C@H]1C[C@@H](CCC(=O)Nc2ncc(C)s2)C2C3CCc4cc(O)ccc4C3CC[C@@]21C]

Prepared from the compound 37 using the debenzylation method described for the compound VII (TMSI, thiourea, N-methylimidazole).

$^1$H-NMR (DMSO-d$_6$): 0.86 (t, 3H), 0.88 (s, 3H), 1.23-2.36 (m, 25H), 2.73 (m, 2H), 4.60 (t, 1H), 6.48 (m, 2H), 7.01 (d, 1H), 7.10 (s, 1H), 9.11 (br S, 1H), 11.88 (s, 1H). MS m/z (TOF ES$^+$): 547 (M+Na).

Compound 39

3-Cyclopentyl-propionic acid (13S,15R,17S)-3-hydroxy-13-methyl-15-[2-(5-methylthiazol-2-yl carbamoyl)-ethyl]-17-oxo-7,8,9,11,12,13,14,15,16,17-decahydro-6H-cyclopenta[a]phenanthren-17-yl ester

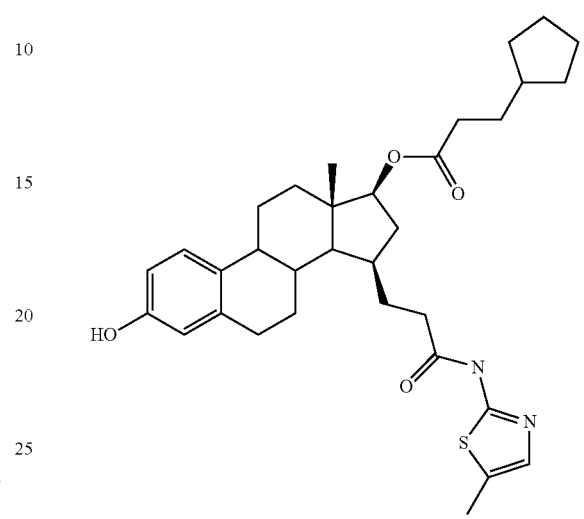

The compound VII was C-3 protected as THP-protection using 3,4-dihydro-2H-pyran in the presence of p-TsOH using the method described for the compound 32, followed by reduction of the C-17 carbonyl with NaBH$_4$ in THF described for the compound 1. Esterification done according to the general method using cyclopentanepropionyl chloride as a reagent.

$^1$H-NMR (DMSO-d$_6$): 0.89 (s, 3H), 0.95-2.90 (m, 34H), 4.61 (m, 1H), 6.45-6.50 (m, 2H), 7.00-7.10 (m, 2H), 9.03 (s, 1H), 11.89 (s, 1H). MS m/z (TOF ES$^+$): 565 (M+1).

Compound 40

Dodecanoic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester

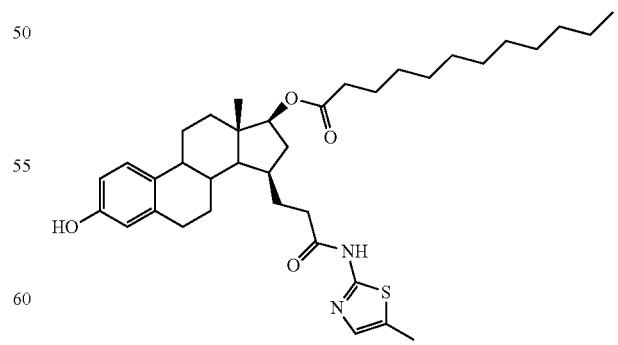

Prepared according to the method described for the compound 39 starting from the compound VII using lauroyl chloride as an esterification reagent. The compound 41 was isolated as a by-product.

¹H-NMR (DMSO-d₆): 0.88 (m, 6H), 1.10-2.90 (m, 41H), 4.62 (m, 1H), 6.45-6.50 (m, 2H), 7.00-7.10 (m, 2H), 9.02 (s, 1H), 11.89 (s, 1H). MS m/z (TOF ES⁺): 623 (M+1).

Compound 41

Dodecanoic acid (13S,15R,17S)-17-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

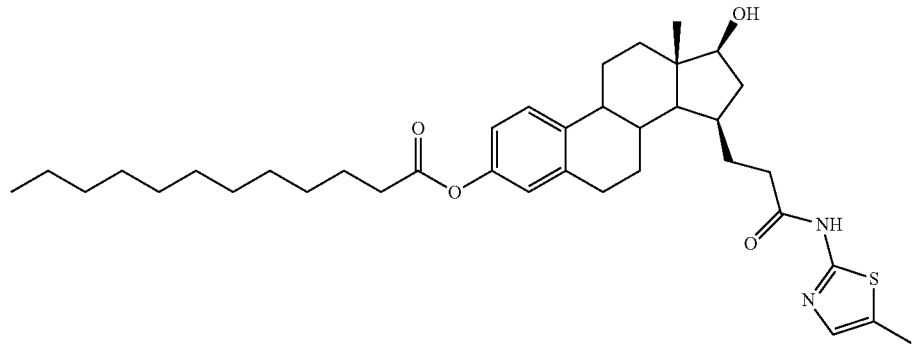 [SMILES: CCCCCCCCCCCC(=O)Oc1ccc2c(c1)CCC1C2CC[C@@]2(C)C1[C@H](CCC(=O)Nc1ncc(C)s1)C[C@@H]2O]

¹H-NMR (DMSO-d₆): 0.88 (m, 6H), 1.10-2.90 (m, 41H), 4.62 (m, 1H), 6.45-6.50 (m, 2H), 7.00-7.10 (m, 2H), 9.02 (s, 1H), 11.89 (s, 1H). MS m/z (TOF ES+): 623 (M+1).

Compound 42

Undec-10-enoic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester

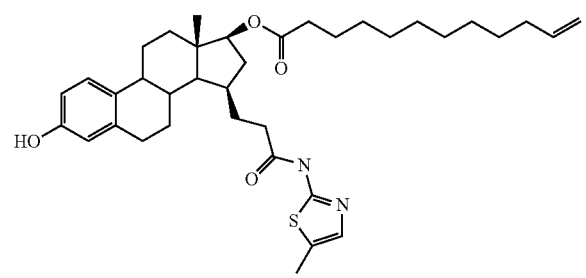 [SMILES: C=CCCCCCCCCCC(=O)O[C@H]1C[C@@H](CCC(=O)Nc2ncc(C)s2)C2C3CCc4cc(O)ccc4C3CC[C@@]21C]

Prepared according to the method described for the compound 39 starting from the compound VII using 10-undecenoyl chloride as an esterification reagent.

¹H-NMR (DMSO-d₆): 0.89 (s, 3H), 1.10-2.50 (m, 35H), 2.74 (m, 2H), 4.61 (t, 1H), 4.90-5.02 (m, 2H), 5.65-5.90 (m, 1H), 6.45-6.51 (m, 2H), 7.00-7.10 (m, 2H), 9.01 (s, 1H), 11.89 (s, 1H). MS m/z (TOF ES⁺): 607 (M+1).

Compound 43

Succinic acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester

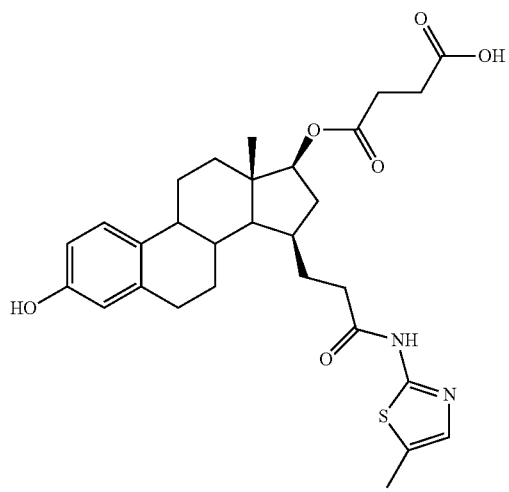 [SMILES: Cc1cnc(NC(=O)CC[C@@H]2C[C@H](OC(=O)CCC(=O)O)[C@@]3(C)CCC4c5ccc(O)cc5CCC4C23)s1]

Succinic anhydride (500 mg, 5 mmol) was dissolved into pyridine (5.7 ml) at 50° C., the compound 1 (500 mg, 1.1 mmol) was added and the reaction mixture stirred at 90-95° C. for 13 hours. Reaction mixture was poured into cold 4% NaCl-solution. The product was extracted trice with EtOAc, washed with water, dried and evaporated. The mixture was then dissolved into 6 ml of methanol. pH was adjusted to 8.5-9 with 10% K₂OC₃ and stirred at rt for 21 hours. pH was adjusted to 6 with 50% acetic acid and solvents were evaporated. 4% NaCl solution was added and the product was extracted trice with EtOAc, washed with ice-cold water, dried and evaporated giving 540 mg (1.0 mmol, 90%) of the compound 43.

1H-NMR (DMSO-d6): 0.90 (t, 3H), 1.20-2.40 (m, 23H), 2.75 (m, 2H), 4.62 (t, 1H), 6.46 (s, 1H), 6.50 (d, 1H), 7.03 (d, 1H), 7.11 (s, 1H), 9.00 (s, 1H), 11.91 (s, 1H), 12.21 (s, 1H). MS m/z (TOF ES+): 563 (M+Na).

Compound 44

Succinic acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester sodium salt

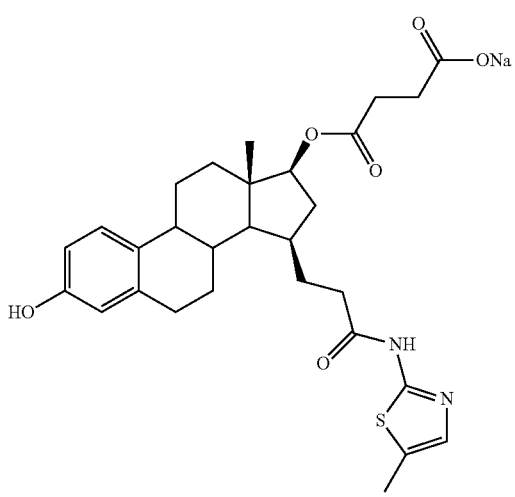

Prepared from the compound 43 by treatment with NaOH solution in EtOH. The precipitated product was filtered from the solution and washed carefully with several amounts of cold ethanol.

1H-NMR (DMSO-d6): 0.87 (s, 3H), 1.20-2.50 (m, 23H), 2.65-2.80 (m, 2H), 4.57 (t, 1H), 6.45 (s, 1H), 6.50 (d, 1H), 7.00 (d, 1H), 7.10 (s, 1H), 11.97 (s, 1H).

Compound 45

Acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester

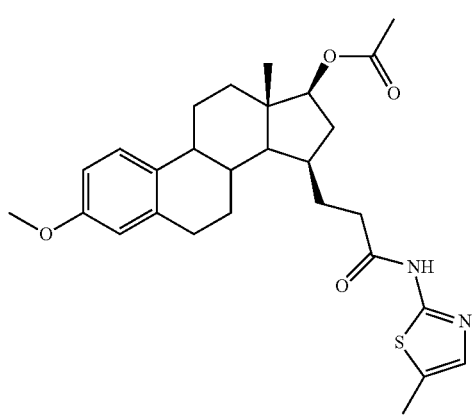 [SMILES: COc1ccc2c(c1)CCC1C2CC[C@@]2(C)C1[C@H](CCC(=O)Nc1ncc(C)s1)C[C@@H]2OC(C)=O]

Prepared from the compound 6 using the general esterification method.

1H-NMR (DMSO-d₆): 0.90 (s, 3H), 1.20-2.38 (m, 23H), 2.80 (m, 2H), 3.69 (s, 3H), 4.60 (t, 1H), 6.65 (m, 2H), 7.11 (s, 1H), 7.18 (d, 1H), 11.90 (s, 1H). MS m/z (TOF ES+): 519 (M+Na).

Compound 46

Phosphoric acid mono-{(13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester

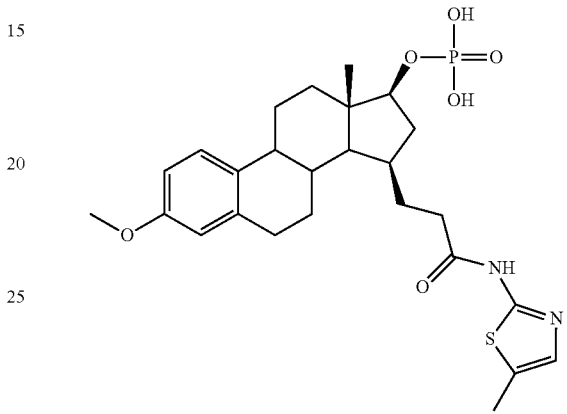

The compound 6 (100 mol %), diethylchlorophosphate (200 mol-%) and dry triethylamine (TEA) (200 mol-%) were dissolved in dry DCM (10 ml), and refluxed for 15 hours. The reaction mixture was diluted with DCM (30 ml), washed with sat. NaHCO₃ (2×20 ml) and brine (20 ml) and dried over sodium sulphate. The solvent was evaporated and the product was purified by chromatography.

1H-NMR (DMSO-d₆): 0.85 (s, 3H), 1.22-2.30 (m, 19H), 2.79 (m, 2H), 3.68 (s, 3H), 4.07 (m, 1H), 6.65 (m, 2H), 7.10 (s, 1H), 7.15 (d, 1H), 11.91 (s, 1H). MS m/z (TOF ES+): 535 (M+1), 557 (M+Na).

Compound 47

Phosphoric acid mono-{(13S,15R,17S)-3-methoxy-13-methyl-15-[2-(5-methyl-thiazol-2-ylcarbamoyl)-ethyl]-17-oxo-7,8,9,11,12,13,14,15,16,17-decahydro-6H-cyclopenta[a]phenanthren-17-yl}ester disodium salt

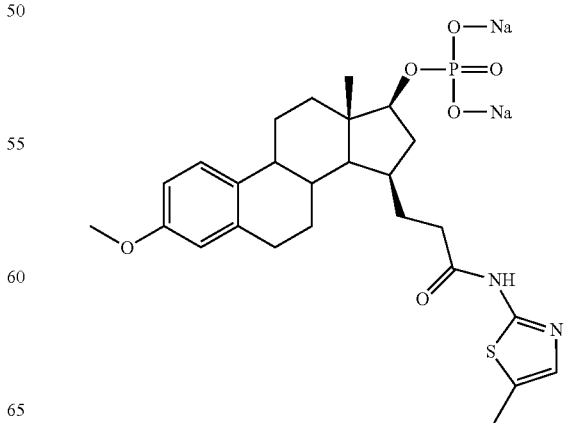

Prepared from the compound 46 by salt preparation by using NaOH solution in EtOH. The product was precipitated by addition of diethyl ether.

¹H-NMR (D₂O): 0.72 (s, 3H), 1.15-2.50 (m, 21H), 3.64 (s, 3H), 3.94 (m, 1H), 6.56 (m, 2H), 7.04 (m, 2H). MS m/z (TOF ES⁺): 579 (M+1), 601 (M+Na).

Compound 48 tert-Butoxycarbonylamino-acetic acid (13S,15R, 17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester

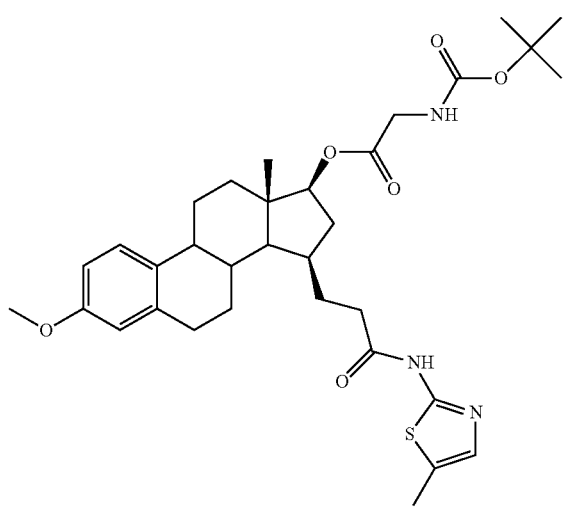 [SMILES: COc1ccc2c(c1)CCC1C2CC[C@@]2(C)C1[C@H](CCC(=O)Nc1ncc(C)s1)C[C@@H]2OC(=O)CNC(=O)OC(C)(C)C]

Prepared from the compound 6 using the EDCl esterification method described for the compound 5.

¹H-NMR (DMSO-d₆): 0.90 (s, 3H), 1.39 (s, 9H), 1.20-2.35 (m, 19H), 2.81 (m, 2H), 3.65 (m, 2H), 3.69 (s, 3H), 4.65 (t, 1H), 6.66 (m, 2H), 7.10 (s, 1H), 7.23 (d, 1H), 11.90 (s, 1H). MS m/z (TOF ES⁺): 634 (M+Na).

Compound 49

Amino-acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester

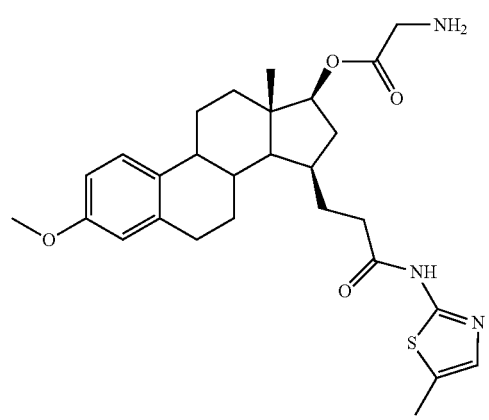 [SMILES: COc1ccc2c(c1)CCC1C2CC[C@@]2(C)C1[C@H](CCC(=O)Nc1ncc(C)s1)C[C@@H]2OC(=O)CN]

The compound 48 (100 mol-%) was dissolved in dry DCM (1 ml). To the cooled mixture TFA (1.6 ml) was added. After stirring for an hour the solvent was evaporated. The precipitate was triturated with diethyl ether.

¹H-NMR (DMSO-d₆): 0.94 (s, 3H), 1.20-2.35 (m, 19H), 2.85 (m, 2H), 3.64 (m, 2H), 3.70 (s, 3H), 4.78 (t, 1H), 6.68 (m, 2H), 7.12 (s, 1H), 7.14 (d, 1H), 8.21 (br s, 2H), 11.93 (s, 1H). MS m/z (TOF ES⁺): 512 (M+1).

Compound 50

Dimethylamino-acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester

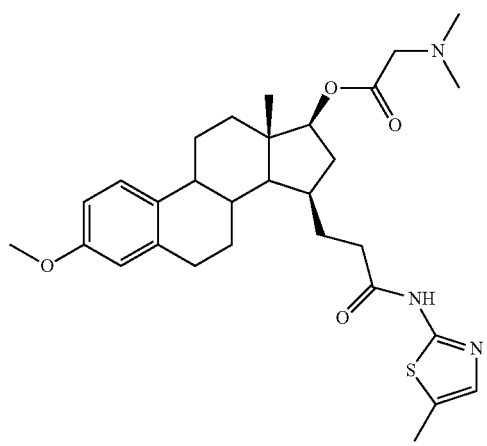 [SMILES: COc1ccc2c(c1)CCC1C2CC[C@@]2(C)C1[C@H](CCC(=O)Nc1ncc(C)s1)C[C@@H]2OC(=O)CN(C)C]

Prepared from the compound 6 using the general esterification method used for the compound 2.

¹H-NMR (DMSO-d₆): 0.91 (s, 3H), 1.20-2.35 (m, 19H), 2.27 (2×s, 6H), 2.81 (m, 2H), 3.20 (m, 2H), 3.69 (s, 3H), 4.66 (t, 1H), 6.65 (m, 2H), 7.10 (s, 1H), 7.13 (d, 1H), 11.90 (s, 1H). MS m/z (TOF ES⁺): 540 (M+1), 562 (M+Na).

Compound 51

Methanesulphonic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester

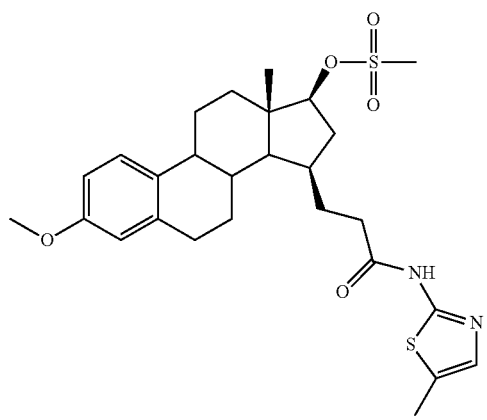 [SMILES: COc1ccc2c(c1)CCC1C2CC[C@@]2(C)C1[C@H](CCC(=O)Nc1ncc(C)s1)C[C@@H]2OS(C)(=O)=O]

Prepared from the compound 6 using the general esterification method using methanesulphonyl chloride as a reagent.

$^1$H-NMR (CDCl$_3$): 1.00 (s, 3H), 1.20-2.60 (m, 19H), 2.87 (m, 2H), 3.02 (s, 3H), 3.78 (s, 3H), 4.55 (t, 1H), 6.68 (m, 2H), 7.06 (s, 1H), 7.18 (d, 1H). MS m/z (TOF ES$^+$): 533 (M+1), 555 (M+Na).

Compound 52

Acetic acid (13S,15R,17S)-17-acetoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

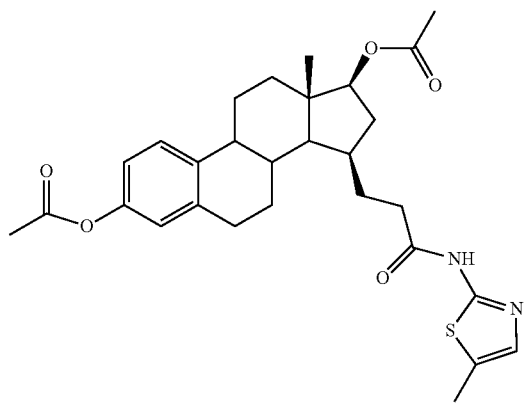 [SMILES: CC(=O)Oc1ccc2c(c1)CCC1C2CC[C@@]2(C)C1[C@H](CCC(=O)Nc1ncc(C)s1)C[C@@H]2OC(C)=O]

The diester 52 was prepared from the compound 1 using the general esterification method in 80% yield.

$^1$H-NMR (DMSO-d$_6$): 0.91 (s, 3H), 1.30-2.40 (m, 25H), 2.83 (m, 2H), 6.82-6.86 (m, 2H), 7.11 (s, 1H), 7.28 (d, 1H), 11.89 (s, 1H). MS m/z (TOF ES$^+$): 547 (M+Na).

Compound 53

Pentanoic acid (13S,15R,17S)-13-methyl-15-[2-(5-methylthiazol-2-ylcarbamoyl)-ethyl]-3-pentanoyloxy-7,8,9,11,12,13,14,15,16,17-decahydro-6H-cyclopenta[a]phenanthren-17-yl ester

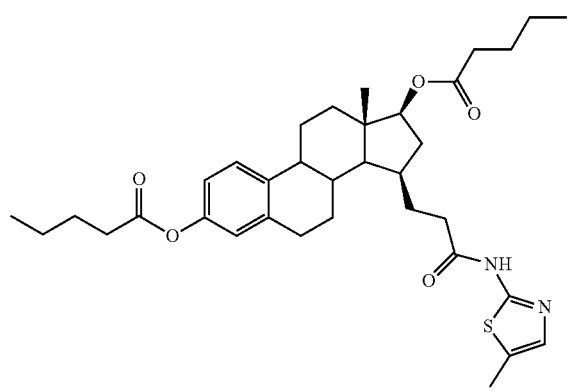 [SMILES: CCCCC(=O)Oc1ccc2c(c1)CCC1C2CC[C@@]2(C)C1[C@H](CCC(=O)Nc1ncc(C)s1)C[C@@H]2OC(=O)CCCC]

The diester 53 was isolated as a by-product in the preparation of the compound 38.

$^1$H-NMR (DMSO-d$_6$): 0.82-0.92 (m, 9H), 1.25-2.58 (m, 33H), 2.84 (m, 2H), 4.63 (t, 1H), 6.83 (m, 2H), 7.11 (s, 1H), 7.27 (d, 1H), 11.89 (s, 1H). MS m/z (TOF ES$^+$): 631 (M+Na).

Compound 54

Dodecanoic acid (13S,15R,17S)-3-dodecanoyloxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester

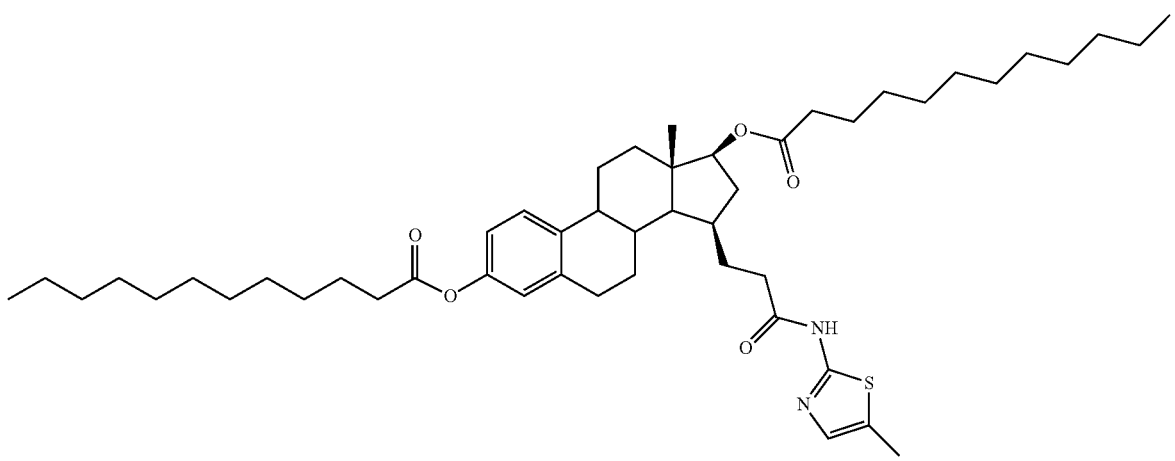 [SMILES: CCCCCCCCCCCC(=O)Oc1ccc2c(c1)CCC1C2CC[C@@]2(C)C1[C@H](CCC(=O)Nc1ncc(C)s1)C[C@@H]2OC(=O)CCCCCCCCCCC]

The compound 54 was isolated as a by-product in the preparation of the compound 40.

$^1$H-NMR (DMSO-d$_6$): 0.82-0.92 (m, 9H), 1.10-2.57 (m, 59H), 2.85 (m, 2H), 4.64 (m, 1H), 6.80-6.84 (m, 2H), 7.11 (s, 1H), 7.25-7.29 (m, 1H), 11.90 (s, 1H). MS m/z (TOF ES$^+$): 806 (M+1).

Compound 55

Benzoic acid (13S,15R,17S)-17-acetoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

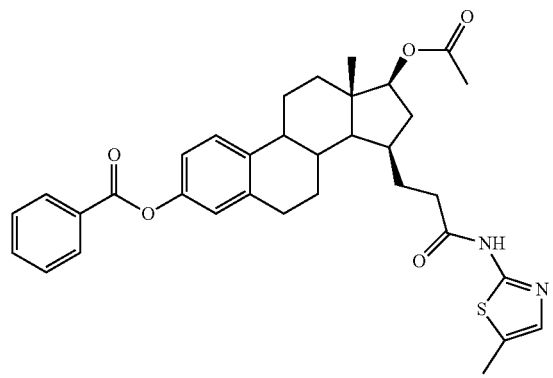 [SMILES: CC(=O)O[C@H]1C[C@@H](CCC(=O)Nc2ncc(C)s2)C2C3CCc4cc(OC(=O)c5ccccc5)ccc4C3CC[C@@]21C]

VII was esterified (step I) by using the general method using benzoyl chloride as a reagent in 81% yield. The C-17 carbonyl group was reduced (step II) as described for the compound 1 in 60% yield. Next, the esterification of the C-17 position (step 3) was performed according to the general method using acetyl chloride as a reagent, affording the compound 55.

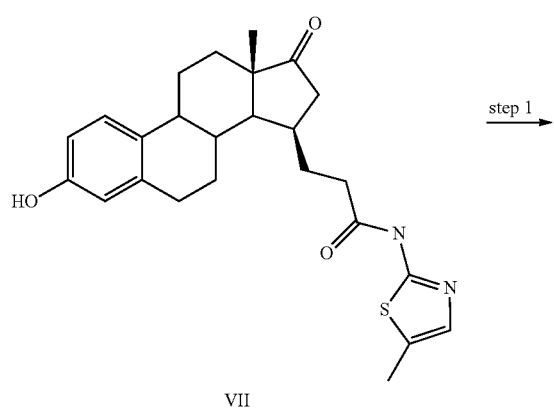

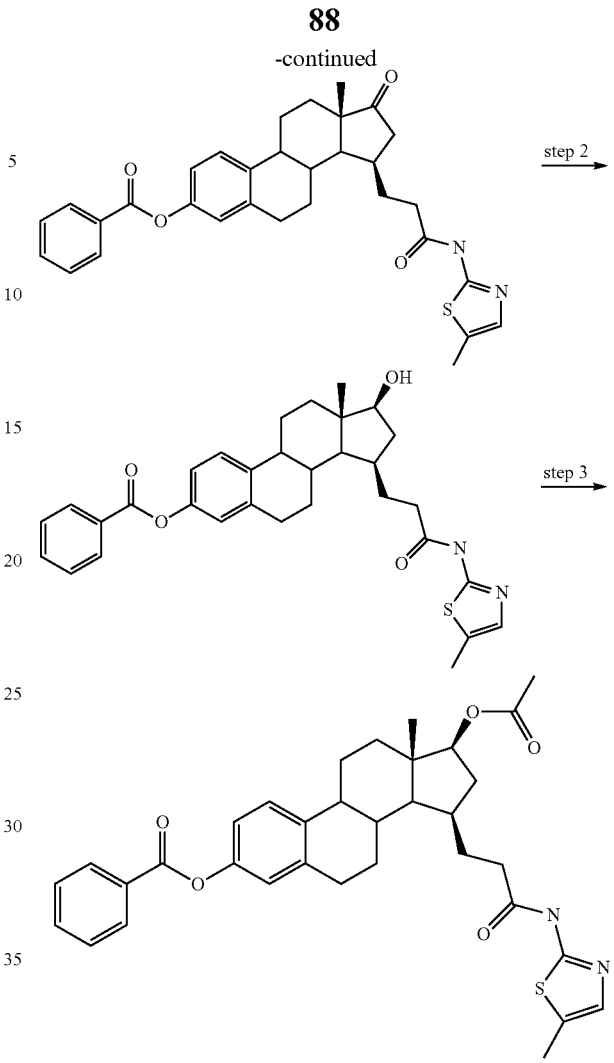

$^1$H-NMR (DMSO-$d_6$): 0.94 (s, 3H), 1.20-2.50 (m, 22H), 2.88 (m, 2H), 4.63 (t, 1H), 7.00-7.04 (m, 2H), 7.11 (s, 1H), 7.35 (d, 1H), 7.57-7.65 (m, 2H), 7.70-7.79 (m, 1H), 8.10-8.14 (m, 2H), 11.91 (s, 1H). MS m/z (TOF ES$^+$): 587 (M+1).

Compound 56

Undec-10-enoic acid (13S,15R,17S)-13-methyl-15-[2-(5-methylthiazol-2-ylcarbamoyl)-ethyl]-3-undec-10-enoyloxy-7,8,9,11,12,13,14,15,16,17-decahydro-6H-cyclopenta[a]phenanthren-17-yl ester

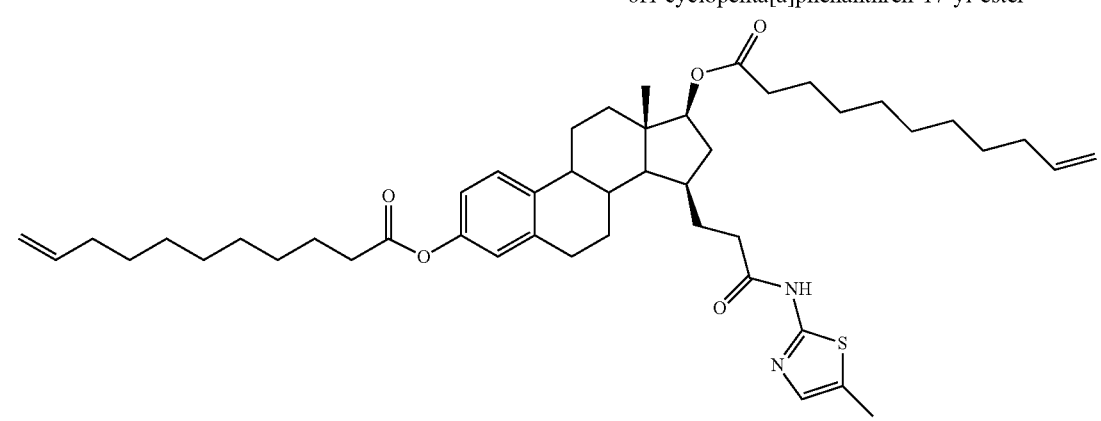

The compound 56 was isolated as a by-product in the preparation of the compound 42.

$^1$H-NMR (DMSO-d$_6$): 0.91 (s, 3H), 1.10-2.56 (m, 51H), 2.84 (m, 2H), 4.63 (t, 1H), 4.90-5.03 (m, 4H), 5.65-5.90 (m, 2H), 6.80-6.84 (m, 2H), 7.10 (s, 1H), 7.25-7.29 (m, 1H), 11.90 (s, 1H). MS m/z (TOF ES$^+$): 796 (M+Na).

Compound 57

Phosphoric acid mono-{(13S,15R,17S)-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester

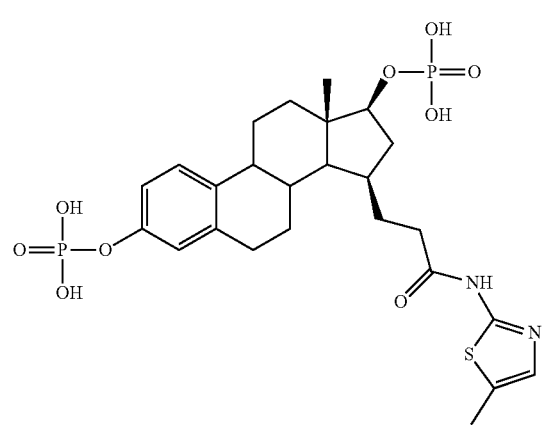 [SMILES: Cc1cnc(NC(=O)CC[C@@H]2C[C@H](OP(=O)(O)O)[C@@]3(C)CCC4c5ccc(OP(=O)(O)O)cc5CCC4C23)s1]

Prepared from the diol 1 using the general phosphorylation method described for the compound 46.

$^1$H-NMR (DMSO-d$_6$): 0.86 (s, 3H), 1.10-2.80 (m, 21H), 4.10 (m, 1H), 6.87 (m, 2H), 7.10 (s, 1H), 7.22 (d, 1H), 11.93 (s, 1H). MS m/z (TOF ES$^+$): 601 (M+1), 623 (M+Na).

Compound 58

Phosphoric acid mono-{(13S,15R,17S)-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester tetrasodium salt

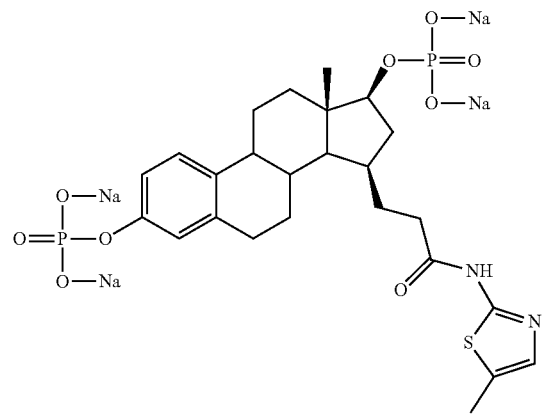

Prepared from the compound 57 by salt preparation by using NaOH solution in EtOH. The product was precipitated by addition of diethyl ether.

$^1$H-NMR (DMSO-d$_6$+D$_2$O): 0.74 (s, 3H), 1.10-2.70 (m, 21H), 3.91 (m, 1H), 6.79 (m, 2H), 6.99 (s, 1H), 7.09 (d, 1H).

Compound 59

Acetic acid (13S,15R,17S)-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester

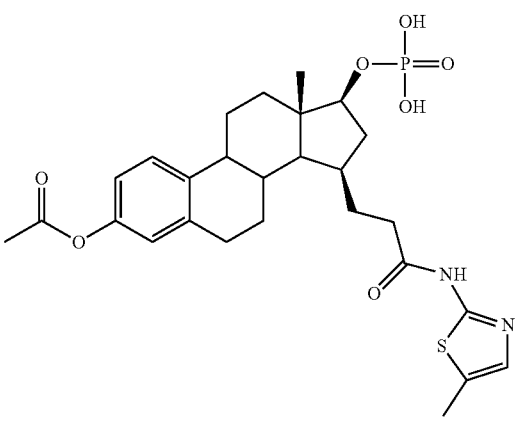 [SMILES: CC(=O)Oc1ccc2c(c1)CCC1C2CC[C@@]2(C)C1[C@H](CCC(=O)Nc1ncc(C)s1)C[C@@H]2OP(=O)(O)O]

The compound 3 (300 mg, 0.622 mmol) and pyridine (0.1 ml, 1.243 mmol) were dissolved in dry THF (10 ml). Phosphorus oxychloride (0.11 ml, 1.243) was added slowly using vigorous stirring. Reaction was stirred at rt for 3 h 50 min. Water (25 ml) was added carefully in to the cold reaction mixture and reaction stirred at rt for 1 h. Precipitate was filtered and washed several times with water. Precipitate was dissolved in toluene and evaporated. The yield of the compound 59 was 0.3 g, 86%.

$^1$H-NMR (DMSO-d$_6$): 0.87 (s, 3H), 1.20-2.50 (m, 24H), 2.83 (m, 2H), 4.06 (m, 1H), 6.82-6.90 (m, 2H), 7.10 (s, 1H), 7.28 (d, 1H), 11.92 (s, 1H). MS m/z (TOF ES$^-$): 561 (M+1).

Compound 60

Phosphoric acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester

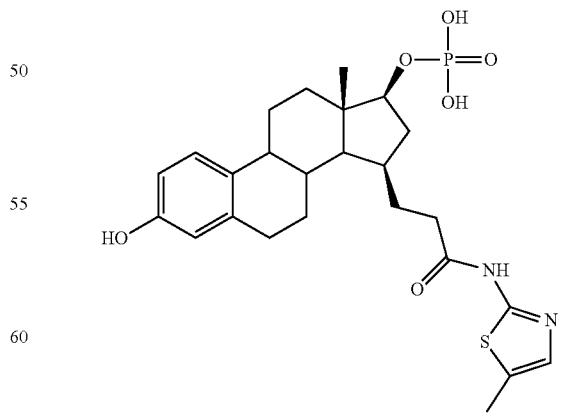

Prepared from the compound 59 by ester hydrolysis using NaOH-solution by stirring at rt for an hour. The reaction mixture was acidified with dilute HCl.

¹H-NMR (DMSO-d₆): 0.85 (s, 3H), 1.20-2.40 (m, 19H), 2.74 (m, 2H), 4.05 (t, 1H), 6.47 (m, 2H), 7.06 (d, 1H), 7.10 (s, 1H), 8.93 (br s, 1H), 11.91 (s, 1H). MS m/z (TOF ES⁻): 519 (M-1).

Compound 61

Phosphoric acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester trisodium salt

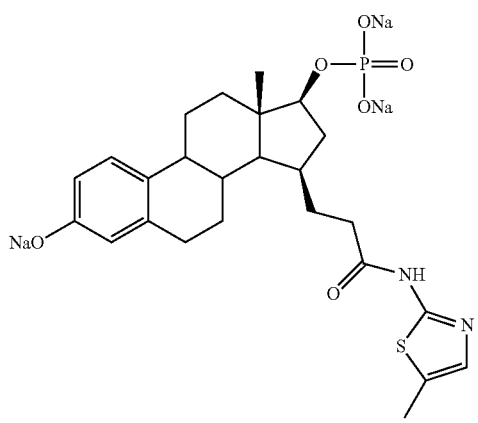

Prepared from the compound 59 by ester hydrolysis and subsequent salt preparation by using NaOH solution in EtOH. The product 61 was precipitated by addition of diethyl ether.

¹H-NMR (D₂O): 0.80 (s, 3H), 1.15-2.50 (m, 19H), 2.68 (m, 2H), 3.96 (m, 1H), 6.41 (m, 2H), 7.02 (s, 1H), 7.08 (d, 1H). MS m/z (TOF ES⁺): 587 (M+1).

Compound 62

3-Cyclopentyl-propionic acid (13S,15R)-3-acetoxy-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-17-yl ester

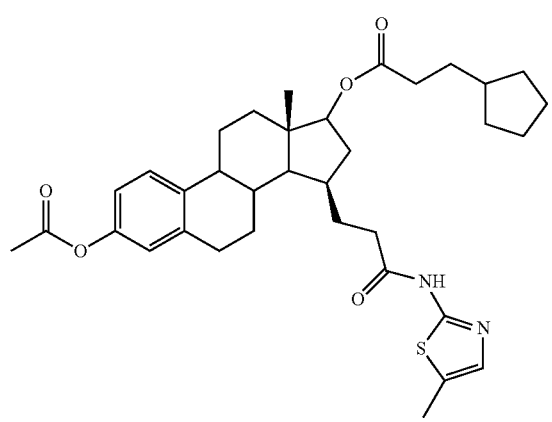 [SMILES: CC(=O)Oc1ccc2c(c1)CCC1C2CC[C@]2(C)C(OC(=O)CCC3CCCC3)C[C@@H](CCC(=O)Nc3ncc(C)s3)C12]

Prepared from the compound 3 using the general esterification method using cyclopentanepropionyl chloride.

¹H-NMR (DMSO-d₆): 0.91 (s, 3H), 1.00-2.50 (m, 35H), 2.83 (m, 2H), 4.62 (t, 1H), 6.82-6.86 (m, 2H), 7.10 (s, 1H), 7.27 (d, 1H), 11.90 (s, 1H). MS m/z (TOF ES⁺): 607 (M+1).

Compound 63 p-Tosylsulphonic acid (13S,15R,17S)-13-methyl-15-[2-(5-methylthiazol-2-ylcarbamoyl)-ethyl]-17-p-tosylsulphonyloxy-7,8,9,11,12,13,14,15,16,17-decahydro-6H-cyclopenta[a]phenanthren-3-yl ester

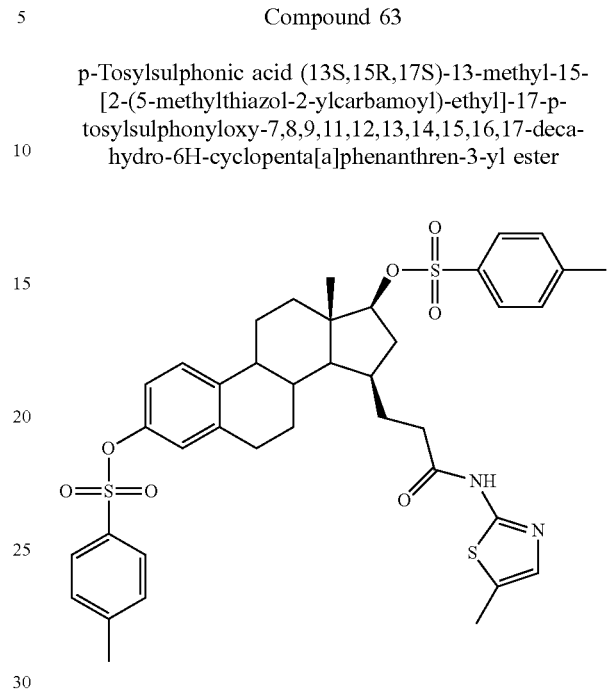

Prepared from the compound 1 using the general esterification method using p-toluenesulfonyl chloride in 91% yield.

¹H-NMR (DMSO-d₆): 0.86 (s, 3H), 1.20-2.50 (m, 27H), 2.74 (m, 2H), 4.31 (t, 1H), 6.68 (m, 2H), 7.10 (s, 1H), 7.19 (d, 1H), 7.47 (m, 4H), 7.78 (m, 4H), 11.86 (s, 1H). MS m/z (TOF ES⁺): 771 (M+Na).

Compound 64

Methanesulphonic acid (13S,15R,17S)-17-methanesulphonyloxy-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester

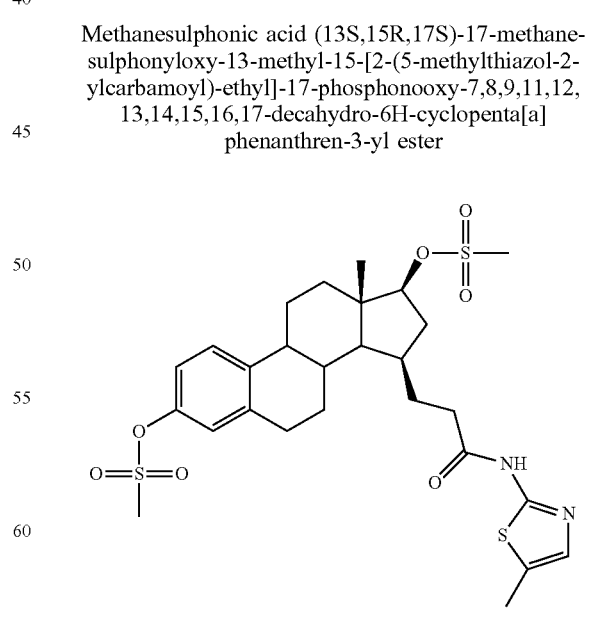

Prepared from the compound 1 using the general esterification method using methanesulfonyl chloride in 84% yield.

¹H-NMR (DMSO-d₆): 0.93 (s, 3H), 1.20-2.50 (m, 27H), 2.88 (m, 2H), 4.54 (t, 1H), 7.09 (m, 3H), 7.38 (d, 1H), 11.92 (s, 1H). MS m/z (TOF ES⁺): 597 (M+1).

Compound 65

Trifluoro-methanesulphonic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

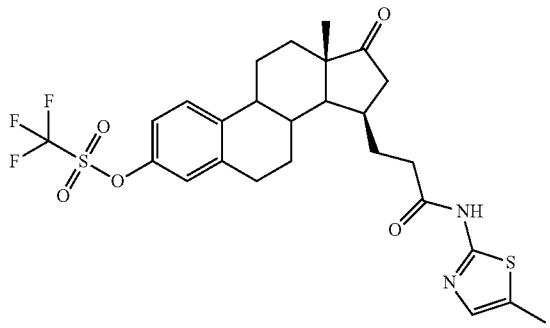 [SMILES: Cc1cnc(NC(=O)CC[C@@H]2CC(=O)[C@@]3(C)CCC4c5ccc(OS(=O)(=O)C(F)(F)F)cc5CCC4C23)s1]

The compound VII (877 mg, 2 mmol) was added into 16 ml of DCM under nitrogen atmosphere. TEA (1.0 g, 1 mmol) was added giving a clear solution. Into this solution at 0° C. was added triflic anhydride (512 μl, 3 mmol). Reaction mixture was then allowed to warm to rt and stirring was continued overnight. Reaction mixture was poured into ice-water. Phases were separated and aqueous phase was extracted twice with DCM. The combined extracts were washed twice with water, dried with Na₂SO₄ and evaporated giving after flash chromatography using DCM-MeOH (85:15) as an eluent 1.00 g (87%) of triflate 65.

¹H-NMR (DMSO-d₆): 0.98 (s, 3H), 1.25-2.50 (m, 19H), 2.85-3.00 (m, 2H), 7.11 (s, 1H), 7.22 (d+s, 2H), 7.46 (d, 1H), 11.91 (s, 1H). MS m/z (TOF ES⁺): 593 (M+Na).

Compound 66

3-((13S,15R)-13-Methyl-17-oxo-7,8,9,11,12,13,14,15,16,17-decahydro-6H-cyclopenta[a]phenanthren-15-yl)-N-(5-methylthiazol-2-yl)propanamide

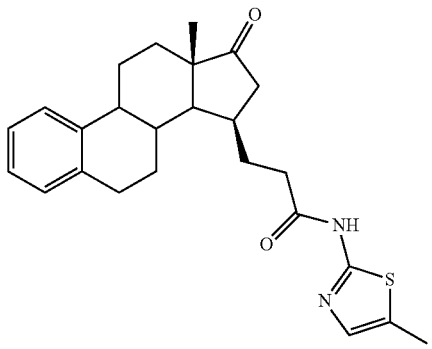 [SMILES: Cc1cnc(NC(=O)CC[C@@H]2CC(=O)[C@@]3(C)CCC4c5ccccc5CCC4C23)s1]

The compound 65 (257 mg, 0.45 mmol, 100 mol-%), 1,1'-Bis[(diphenylphosphino)ferrocene]dichloropalladium (11) (22 mg, 0.027 mmol, 6 mol-%), TEA (0.19 ml, 1.35 mmol, 300 mol-%) and 4 ml of toluene were charged into reaction vessel. The vessel was closed with a septum and flushed using vacuum/nitrogen, formic acid (33 μl, 0.9 mmol, 200 mol-%) was added and the mixture stirred at 90° C. for 3 h. The reaction mixture was filtered with celite and filtrate was washed several times with toluene. Combined toluene fractions were washed thrice with 1 N HCl and then with water, dried and evaporated giving 178 mg (92%) of crude product, after flash chromatography 133 mg (70%) of pure 66.

¹H-NMR (DMSO-d₆): 0.98 (s, 3H), 1.25-2.45 (m, 19H), 2.80-2.95 (m, 2H), 7.05-7.15 (m, 4H), 7.20-7.35 (m, 1H), 11.93 (s, 1H). MS m/z (TOF ES⁺): 445 (M+Na).

Compound 67

3-((13S,15R)-17-Hydroxy13-methyl-7,8,9,11,12,13,14,15,16,17-decahydro-6H-cyclopenta[a]phenanthren-15-yl)-N-(5-methylthiazol-2-yl)propanamide

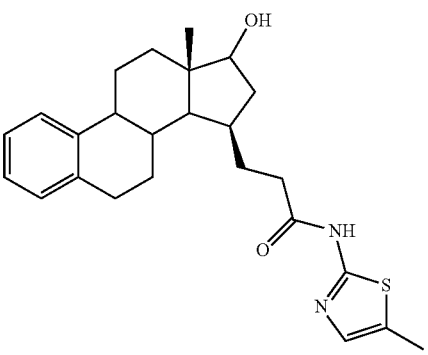 [SMILES: Cc1cnc(NC(=O)CC[C@@H]2CC(O)[C@@]3(C)CCC4c5ccccc5CCC4C23)s1]

The compound 67 was prepared from the compound 66 by using NaBH₄ in the reduction as described for the compound 1.

¹H-NMR (CDCl₃+MeOD-d₄): 0.90 (s, 3H), 1.2-2.6 (m, 21H), 3.69 (t, 1H), 7.02 (s, 1H), 7.05-7.2 (m, 3H), 7.30 (m, 1H). MS m/z (TOF ES⁺): 447 (M+Na).

Compound 68

3-{(13S,15R)-17-Formylamino-3-hydroxy-13-methyl-7,8,9,11,12,13,14,15,16,17-decahydro-6H-cyclopenta[a]phenanthren-15-yl}-N-(5-methylthiazol-2-yl)propanamide

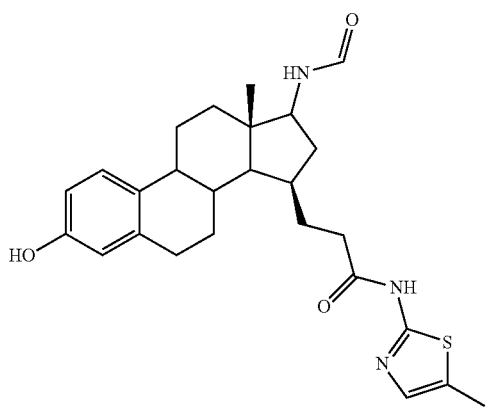 [SMILES: Cc1cnc(NC(=O)CC[C@@H]2CC(NC=O)[C@@]3(C)CCC4c5ccc(O)cc5CCC4C23)s1]

The compound VII (20 mg) was dissolved in formamide (0.7 ml) and heated with microwaves at 160° C. for 20 minutes. The product mixture was purified by chromatography affording the compound 68 as a main product.

¹H-NMR (CDCl3+MeOH-d4): 0.87 (s, 3H), 1.20-2.50 (m, 21H), 2.7-2.9 (m, 2H), 2.39 (s, 3H), 4.0 (t, 1H), 6.57 (s, 2H), 6.62 (d, 1H), 7.03 (d, 1H), 7.10 (d, 1H), 7.41 (s, 1H), 8.14 (s, 1H), 9.49 (s, 1H), 11.94 (br s, 1H). MS m/z (TOF ES⁺): 490 (M+Na).

Nitration of the Compound VII

The reaction vessel was charged with the compound VII (1.32 g, 3 mmol) and ethanol (45 ml) under nitrogen atmosphere. THF (30 ml) and ferric nitrate (600 mg, 1.5 mmol) were added. After stirring the reaction mixture for 4 h at 60° C., the solvents were evaporated. HPLC of the crude reaction mixture showed 45% of 2-nitro-isomer 69a and 35% of 4-nitroisomer 69b. Purification by flash chromatography gave 358 mg of 69a and 284 mg of 69b. In addition, the product mixture contained ca. 5% of 2,4-dinitro derivative 69c.

Compound 69a 3-((13S,15R)-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

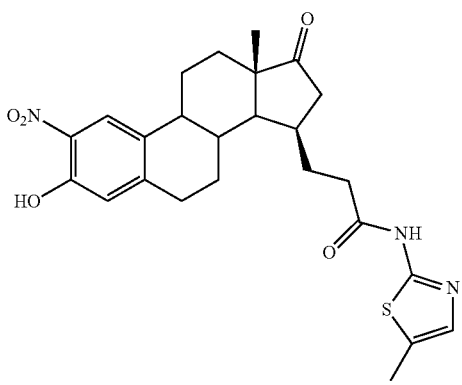 [SMILES: Cc1cnc(NC(=O)CC[C@@H]2CC(=O)[C@@]3(C)CCC4c5cc([N+](=O)[O-])c(O)cc5CCC4C23)s1]

$^1$H-NMR (CDCl$_3$): 1.07 (s, 3H), 1.30-2.75 (m, 19H), 2.9-3.05 (m, 2H), 6.89 (s, 1H), 7.05 (s, 1H), 7.98 (s, 1H). MS m/z (TOF ES$^+$): 506 (M+Na)

Compound 69b 3-((13S,15R)-3-hydroxy-13-methyl-4-nitro-17-oxo-7,8,9,11,12,13,14,15,16,17-decahydro-6H-cyclopenta[a]phenanthren-15-yl)-N-(5-methylthiazol-2-yl)propanamide

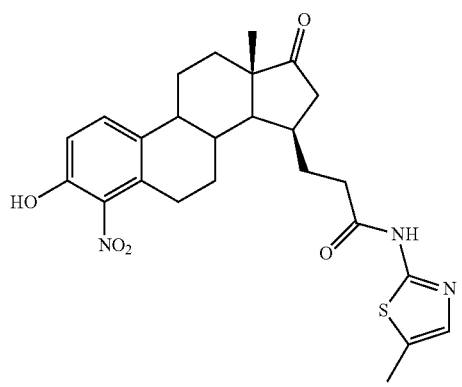 [SMILES: Cc1cnc(NC(=O)CC[C@@H]2CC(=O)[C@@]3(C)CCC4c5ccc(O)c([N+](=O)[O-])c5CCC4C23)s1]

$^1$H-NMR (CDCl$_3$): 1.08 (s, 3H), 1.3-3.4 (m, 21H), 6.96 (d, 1H), 7.05 (s, 1H), 7.45 (d, 1H). MS m/z (TOF ES$^+$): 506 (M+Na)

Compound 69c 3-((13S,15R)-3-hydroxy-13-methyl-2,4-dinitro-17-oxo-7,8,9,11,12,13,14,15,16,17-decahydro-6H-cyclopenta[a]phenanthren-15-yl)-N-(5-methylthiazol-2-yl)propanamide

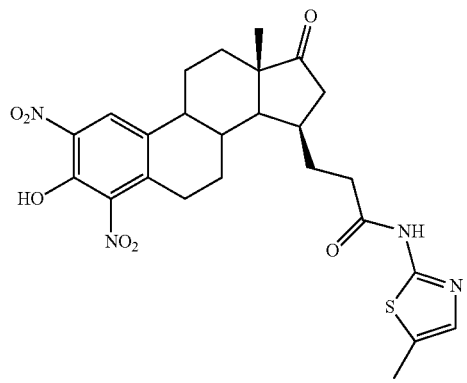 [SMILES: Cc1cnc(NC(=O)CC[C@@H]2CC(=O)[C@@]3(C)CCC4c5cc([N+](=O)[O-])c(O)c([N+](=O)[O-])c5CCC4C23)s1]

$^1$H-NMR (CDCl$_3$): 1.08 (s, 3H), 1.35-3.10 (m, 21H), 7.03 (s, 1H), 8.14 (s, 1H). MS m/z (TOF ES$^+$): 529 (M+H)

Compound 70

3-((13S,15R)-4-amino-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

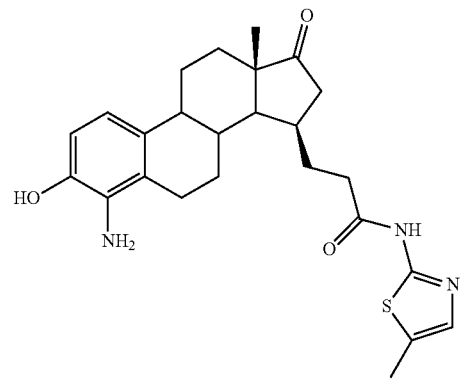

Hydrogenation of the compound 69b was carried out at atmospheric pressure at rt in ethanol/THF 1:1 using 10% Pd/C as catalyst. Catalyst was filtered off, solvents were evaporated and product 70 was purified by flash chromatography.

$^1$H-NMR (CDCl$_3$+MeOH-d$_4$): 1.03 (s, 3H), 1.35-2.65 (m, 19H), 2.75-3.00 (m, 2H), 6.63 (s, 2H), 7.03 (s, 1H). MS m/z (TOF ES$^+$): 476 (M+Na).

Compound 71

3-((13S,15R,17S)-3,17-Dihydroxy-4-isopropylamino-13-methyl-7,8,9,11,12,13,14,15,16,17-decahydro-6H-cyclopenta[a]phenanthren-15-yl)-N-(5-methylthiazol-2-yl)propionamide

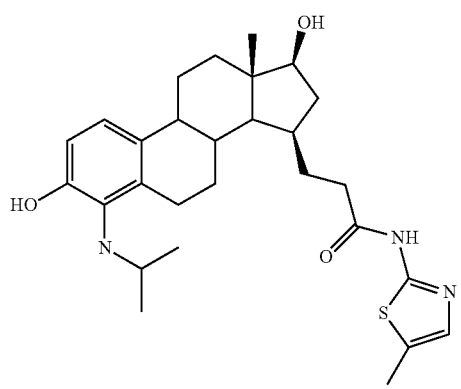 [SMILES: Cc1cnc(NC(=O)CC[C@@H]2C[C@H](O)[C@@]3(C)CCC4c5ccc(O)c(NC(C)C)c5CCC4C23)s1]

The compound 70 (50 mg, 0.11 mmol, 100 mol-%) and acetone (80 µl, 1.1 mmol, 1000 mol-%) were dissolved in dry THF (2 ml) with molecular sieves 4 Å (500 mg). After addition of acetic acid (40 µl, ~600 mol-%) and stirring for 30 minutes, NaBH$_4$ (17 mg, ~400 mol-%) was added. The reaction mixture was stirred at rt for 3.5 hours. Water (5 ml) was added and pH was adjusted to pH 8-9 with NaOH-solution. The product was extracted with EtOAc, and washed with water and brine. The crude product was purified by chromatography using 2% MeOH in DCM affording the product 71 (19 mg, yield 35%).

$^1$H-NMR (CDCl$_3$): 0.89 (s, 3H), 1.10 & 1.16 (2×d, 6H), 1.27-1.75 (m, 8H), 1.87-2.30 (m, 14H), 2.76 (m, 2H), 3.25 (m, 1H), 3.72 (t, 1H), 6.74 (d, 1H), 7.0 (d, 1H), 7.06 (s, 1H).

Compound 72

3-[(13S,15R,17S)-3,17-Dihydroxy-4-(2-hydroxy-1-methyl-ethylamino)-13-methyl-7,8,9,11,12,13,14,15,16,17-decahydro-6H-cyclopenta[a]phenanthren-15-yl]-N-(5-methylthiazol-2-yl)propionamide

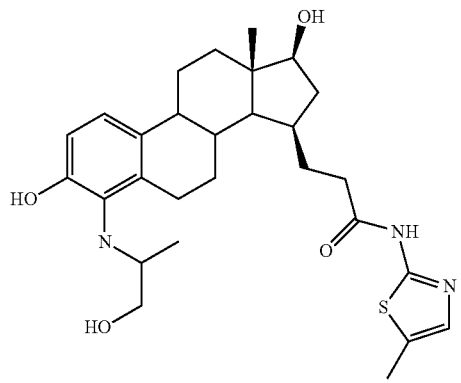 [SMILES: Cc1cnc(NC(=O)CC[C@@H]2C[C@H](O)[C@@]3(C)CCC4c5ccc(O)c(NC(C)CO)c5CCC4C23)s1]

The compound was prepared from the amine 70 using the same methods as used for the compound 71 except using hydroxyacetone as a ketone. The reaction was completed in two hours.

$^1$H-NMR (CDCl$_3$): 1.04 (s, 3H), 1.14 (d, 3H), 1.30-1.92 (m, 8H), 2.10-2.90 (m, 15H), 3.24 (m, 1H), 3.49 (s, 2H), 3.65-3.78 (m, 1H), 6.75 (d, 1H), 6.95 (d, 1H), 7.05 (s, 1H).

Compound 73

3-[(13S,15R)-3-Hydroxy-17-isopropylamino-13-methyl-7,8,9,11,12,13,14,15,16,17-decahydro-6H-cyclopenta[a]phenanthren-15-yl]-N-(5-methylthiazol-2-yl)propionamide

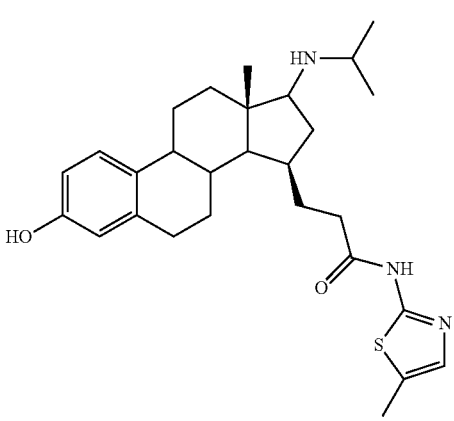 [SMILES: Cc1cnc(NC(=O)CC[C@@H]2CC(NC(C)C)[C@@]3(C)CCC4c5ccc(O)cc5CCC4C23)s1]

The compound VII (100 mg, 0.23 mmol, 100 mol-%) was dissolved in DCM (2 ml) and THF (2 ml). Isopropylamine (190 µl, 2.28 mmol, 10 eq.), Zn (90 mg, 1.36 mmol, 600 mol-%) and acetic acid (80 µl, 1.36 mmol, 600 mol-%) were added to the reaction mixture. After stirring at rt for two hours, NaBH$_4$ (35 mg, 0.9 mmol, 400 mol-%) was added. Stirring was continued at +40° C. for 4 hours, then rt overnight. The reaction mixture was poured to ice-water (10 ml) and EtOAc, stirred for 30 minutes. The precipitate was filtered and washed carefully with EtOAc. The filtrate was washed with water, which after acidification with 1N HCl-solution was washed with EtOAc. The water phase was neutralized and the product 73 was extracted in EtOAc, and washed with water and brine.

$^1$H-NMR (CDCl$_3$+MeOH-d$_4$): 0.86 (s, 3H), 1.11 (dd, 6H), 1.20-1.65 (m, 11H), 1.85-2.85 (m, 14H), 3.03 (t, 1H), 6.56-6.80 (m, 2H), 7.04-7.10 (m, 2H).

Compound 74

3-((13S,15R)-3-Hydroxy-17-isobutylamino-13-methyl-7,8,9,11,12,13,14,15,16,17-decahydro-6H-cyclopenta[a]phenanthren-15-yl]-N-(5-methylthiazol-2-yl)propionamide

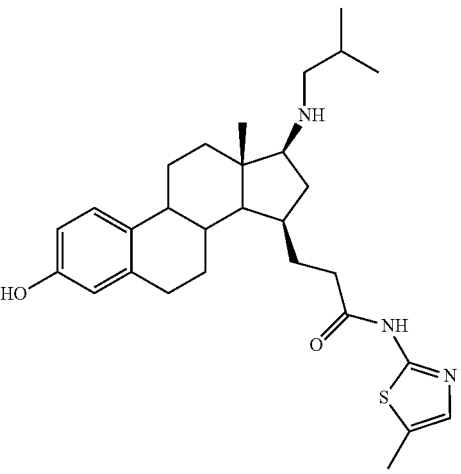 [SMILES: Cc1cnc(NC(=O)CC[C@@H]2C[C@H](NCC(C)C)[C@@]3(C)CCC4c5ccc(O)cc5CCC4C23)s1]

The synthesis was done by the same method as for the compound 73 using isobutylamine (600 mol-%) as a reagent. Reaction was stirred at rt for 1 hour and then at 40° C. for 5 hours. The crude product was purified by flash chromatography.

$^1$H-NMR (CDCl$_3$): 0.85 (s, 3H), 0.90 (dd, 6H), 1.10-1.60 (m, 7H), 1.71-2.75 (m, 18H), 6.53-6.61 (m, 2H), 7.05 (br s, 2H).

Compound 75a 3-((13S,15R)-2-(tert-butyl)-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

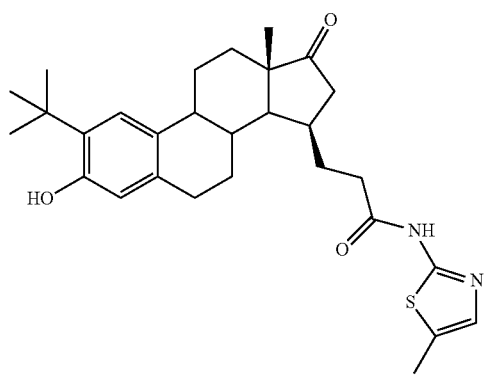 [SMILES: Cc1cnc(NC(=O)CC[C@@H]2CC(=O)[C@@]3(C)CCC4c5cc(C(C)(C)C)c(O)cc5CCC4C23)s1]

To a stirred suspension of the compound VII (2.0 g, 100 mol-%) in dry DCM, tert-butanol (1.5 ml) and boron trifluoride diethyl etherate (3.2 ml) were added with a syringe at rt and the reaction was followed by TLC. The mixture was stirred overnight at rt and additional amount of boron trifluoride diethyl etherate (1 ml) and tert-butanol (500 µl) were added. The resulting orange solution was stirred for 3 hours before water (40 ml) and DCM (40 ml) were added carefully. The layers were separated and the aqueous layer was extracted with DCM (3×30 ml). The combined organic layers were washed with water (3×30 ml), saturated aqueous NaHCO$_3$ (30 ml) and brine (3×30 ml). The solvents were evaporated and the precipitate was washed with heptane affording 1.8 g of the product 75a (yield 80%).

$^1$H-NMR (DMSO-d$_6$): 0.97 (s, 3H), 1.2-1.45 (m, 12H), 1.5-2.4 (m, 16H), 2.6-2.95 (m, 2H), 6.47 (s, 1H), 7.01 (s, 1H), 7.11 (s, 1H), 8.97 (s, 1H), 11.92 (s, 1H, —NH). MS m/z (TOF ES+): 517 (M+Na)

Compound 75b 3-((13S,15R)-2-tert-Butyl-3-Hydroxy-17-isobutylamino-13-methyl-7,8,9,11,12,13,14,15,16,17-decahydro-6H-cyclopenta[a]phenanthren-15-yl]-N-(5-methylthiazol-2-yl)propionamide

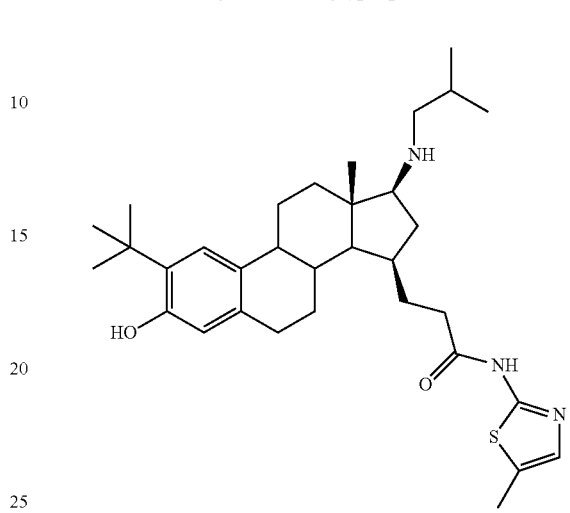

The compound 75b was prepared by the same method used for the compound 73 using isobutylamine (600 mol-%) as a reagent and the compound 75a as a starting material. Reaction was stirred at 40° C. for 4 hours and overnight at rt.

$^1$H-NMR (CDCl$_3$): 1.06 & 1.09 (2×s, 6H), 1.37 (s, 9H), 1.54-1.77 (m, 3H), 1.80-3.05 (m, 25H), 6.49 (s, 1H), 7.00 (s, 1H), 7.12 (s, 1H).

Compound 76

3-((13S,15R)-17-[(Furan-2-ylmethyl)-amino]-3-hydroxy-13-methyl-7,8,9,11,12,13,14,15,16,17-decahydro-6H-cyclopenta[a]phenanthren-15-yl]-N-(5-methylthiazol-2-yl)propionamide

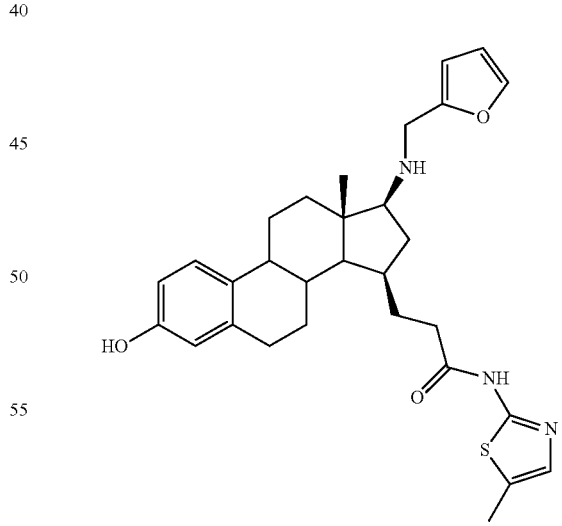

The compound 76 was prepared by the same method used for the compound 73 using furfurylamine (600 mol-%) as a reagent. Reaction was stirred at rt for an hour, then at 40° C. for 5 hours. The crude product was purified by flash chromatography.

$^1$H-NMR (CDCl$_3$+MeOH-d4): 1.04 (s, 3H), 1.35-1.79 (s, 8H), 2.00-2.89 (m, 17H), 4.06 (d, 2H), 6.42 (s, 1H), 6.53-6.63 (m, 3H), 7.05 (s, 1H), 7.47 (s, 1H).

Compound 77

3-((13S,15R)-3-Hydroxy-17-(2-methoxyethyl-amino)-13-methyl-7,8,9,11,12,13,14,15,16,17-decahydro-6H-cyclopenta[a]phenanthren-15-yl]-N-(5-methylthiazol-2-yl)propionamide

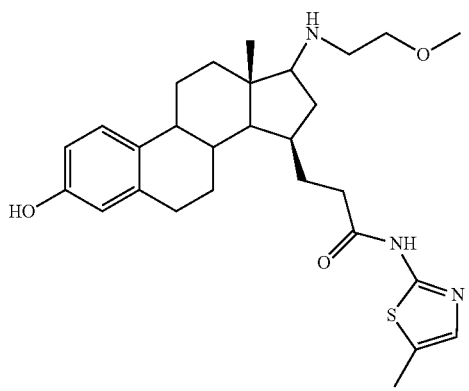 [SMILES: COCCNC1C[C@@H](CCC(=O)Nc2ncc(C)s2)C2C3CCc4cc(O)ccc4C3CC[C@]12C]

Starting material VII (100 mg, 0.23 mmol, 100 mol-%) was dissolved in THF (2 ml) and DCM (2 ml) under nitrogen atmosphere. 2-Methoxyethylamine (120 µl, 1.36 mmol, 600 mol-%), Zn (90 mg, 1.36 mmol, 600 mol-%) and acetic acid (80 µl, 1.36 mmol, 600 mol-%) were added. Reaction was stirred at rt for 30 min and NaBH$_4$ (34.5 mg, 0.91 mmol, 400 mol-%) was added. Reaction was stirred at rt for 1 hour and at 40° C. for 3 hours. Reaction was allowed to cool down and then poured in to ice-water (10 ml). Reaction was filtered through Celite and extracted with EtOAc (3×5 ml). Combined organic layers were washed with water (3×10 ml) and brine (3×10 ml) and dried with Na$_2$SO$_4$. Crude product (115 mg) was triturated with heptane and purified by flash chromatography affording 46 mg of the C-17 amine derivative 77.

$^1$H-NMR (CDCl$_3$): 0.86 (s, 3H), 1.25-1.65 (m, 7H), 1.75-2.86 (m, 17H), 3.34 (s, 4H), 3.51 (m, 2H), 6.54 (s, 1H), 6.59 (d, 1H), 7.04-7.08 (m, 2H).

Compound 78

3-((13S,15R)-3-Hydroxy-17-(2-hydroxyethyl-amino)-13-methyl-7,8,9,11,12,13,14,15,16,17-decahydro-6H-cyclopenta[a]phenanthren-15-yl]-N-(5-methylthiazol-2-yl)propionamide

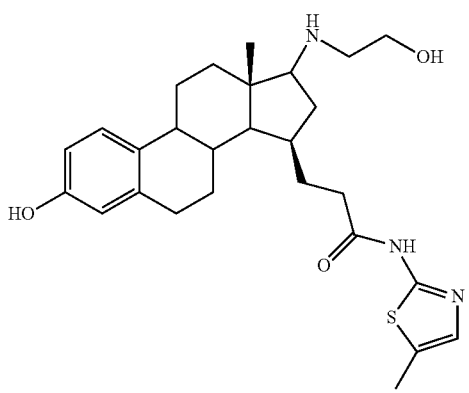 [SMILES: Cc1cnc(NC(=O)CC[C@@H]2CC(NCCO)[C@@]3(C)CCC4c5ccc(O)cc5CCC4C23)s1]

The compound 78 was prepared by the same method used for the compound 77 using ethanolamine (1000 mol-%) as reagent. Reaction was stirred at rt for 1 hour and at +40° C. for 3 hours.

$^1$H-NMR (CDCl$_3$+MeOH-d4): 0.91 (s, 3H), 1.23-1.61 (m, 8H), 1.95-2.89 (m, 17H), 3.70 (m, 2H), 6.57-6.64 (m, 2H), 7.03 (d, 1H), 7.09 (d, 1H).

Compound 79

3-((13S,15R)-2-tert-Butyl-3-hydroxy-17-(2-methoxyethylamino)-13-methyl-7,8,9,11,12,13,14,15,16,17-decahydro-6H-cyclopenta[a]phenanthren-15-yl)-N-(5-methylthiazol-2-yl)propionamide

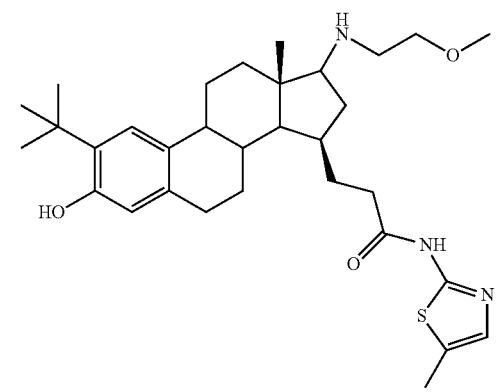 [SMILES: COCCNC1C[C@@H](CCC(=O)Nc2ncc(C)s2)C2C3CCc4cc(O)c(C(C)(C)C)cc4C3CC[C@]12C]

The compound 79 was prepared by the same method used for the compound 77 except that reaction temperature was +40° C. already from the beginning and starting material was the compound 75a. Reaction was stirred at 40° C. for 4.5 hours and overnight at rt.

$^1$H-NMR (CDCl$_3$): 0.88 (s, 3H), 1.23-1.62 (m, 17H), 1.94-2.86 (m, 20H), 3.50 (s, 2H), 6.40 (s, 1H), 7.03 (d, 1H), 7.15 (s, 1H).

Compound 80a

3-[(13S,15R)-17-(3-Dimethylamino-propylamino)-3-hydroxy-13-methyl-7,8,9,11,12,13,14,15,16,17-decahydro-6H-cyclopenta[a]phenanthren-15-yl]-N-(5-methylthiazol-2-yl)propionamide

Compound 80b

3-[(13S,15R)-17-(3-Dimethylamino-propylamino)-3-hydroxy-13-methyl-7,8,9,11,12,13,14,15,16,17-decahydro-6H-cyclopenta[a]phenanthren-15-yl]-N-(5-methylthiazol-2-yl)propionamide dihydrochloride

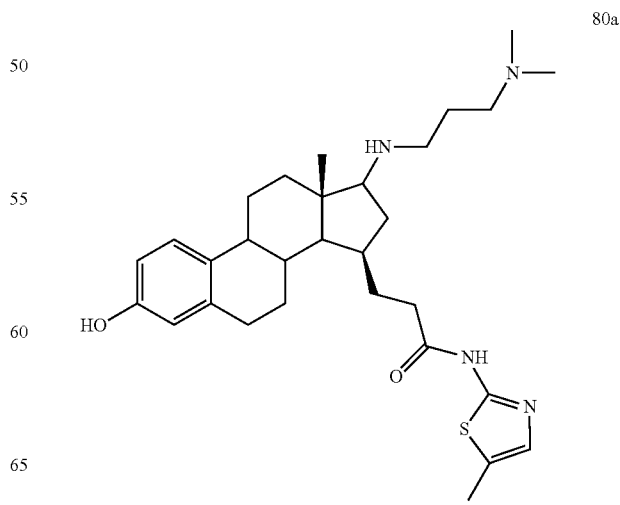

-continued

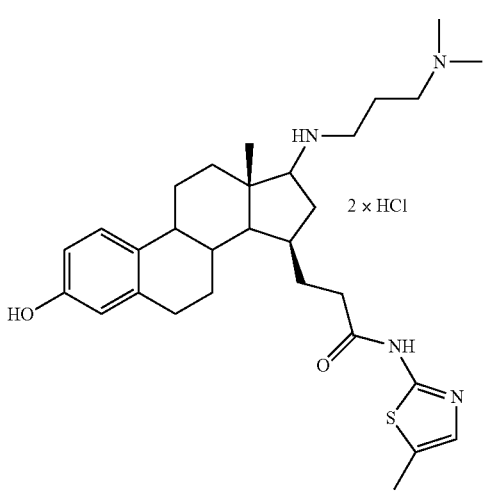

80b

The compound 80a was prepared by the same method used for the compound 77 using 3-dimethylamino-1-propylamine as reagent at +40° C. Reaction was stirred at +40° C. for 5.5 hours and overnight at rt. The crude product was purified by flash chromatography. The compound 80a was treated with dilute HCl in EtOAc producing the salt 80b.

80a: $^1$H-NMR (CDCl$_3$): 0.83 (s, 3H), 1.25-2.20 (m, 20H), 2.41 (s, 3H), 2.56 (s, 6H), 2.60-2.84 (m, 6H), 6.54 (s, 1H), 6.60 (d, 1H) 7.05-7.08 (m, 2H).

80b: $^1$H-NMR (CDCl$_3$+MeOH-d4): 0.88 (s, 3H), 1.19-2.18 (m, 20H), 2.25 (s, 3H), 2.38 (s, 6H), 2.58-2.77 (m, 6H), 6.54 (s, 1H), 6.58 (d, 1H) 7.02-7.05 (m, 2H).

Compound 81

3-[(13S,15R)-17-(2-Dimethylamino-ethylamino)-3-hydroxy-13-methyl-7,8,9,11,12,13,14,15,16,17-decahydro-6H-cyclopenta[a]phenanthren-15-yl]-N-(5-methylthiazol-2-yl)propionamide

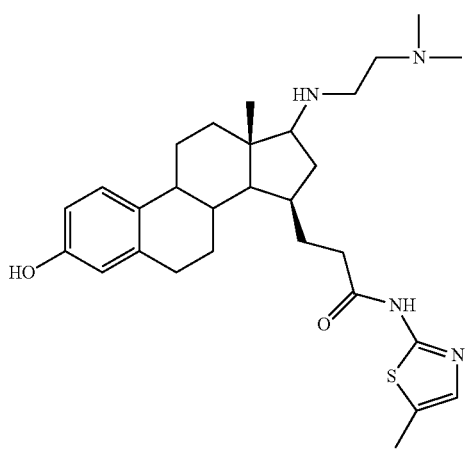 [SMILES: Cc1cnc(NC(=O)CC[C@@H]2CC(NCCN(C)C)[C@@]3(C)CCC4c5ccc(O)cc5CCC4C23)s1]

The compound 81 was prepared by the same method used for the compound 77 using 2-dimethylaminoethylamine as reagent. Reaction was refluxed for 2 hours and stirred at +60° C. for 2.5 hours and overnight at rt. The crude product was purified by flash chromatography.

$^1$H-NMR (CDCl$_3$+MeOH-d4): 0.82 (s, 3H), 1.18-1.48 (m, 7H), 1.91-2.10 (m, 13H), 2.25 (s, 3H), 2.39 (s, 6H), 2.58-2.77 (m, 4H), 6.53 (s, 1H), 6.58 (d, 1H) 7.04 (s, 1H), 7.06 (m, 1H).

Pharmacological Tests

The following tests are provided to demonstrate the present invention in illustrative way and should not be considered as limiting in the scope of invention. Further, the concentrations of the compound in the assays are exemplary and should not be taken as limiting. A person skilled in the art may define pharmaceutically relevant concentrations with method known in the art.

Inhibition of 17β-Hydroxysteroid Dehydrogenase Type 1 Enzyme

17β-HSD1 Production and Isolation:

Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested; the microsomal fraction was isolated as described by Puranen, T. J., Poutanen, M. H., Peltoketo, H. E., Vihko, P. T. and Vihko, R. K. (1994) Site-directed mutagenesis of the putative active site of human 17 β-hydroxysteroid dehydrogenase type 1. Biochem. J. 304: 289-293. Aliquots were stored frozen until determination of enzymatic activity.

Assay—Inhibition of Recombinant Human 17β-HSD1:

Recombinant protein (1 µg/ml) was incubated in 20 mM KH2PO4 pH 7.4 with 30 nM estrone (including 800.000 cpm/ml of $^3$H-estrone) and 1 mM NADPH for 30 min at RT, in the presence of the potential inhibitor at concentrations 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estrone to estradiol was calculated according to the following formula:

$$\% \text{ conversion} = 100 \times \frac{\{(\text{cpm estradiol in sample with inhibitor})/[(\text{cpm estrone in sample with inhibitor}) + (\text{cpm estradiol in sample with inhibitor})]\}}{[(\text{cpm estradiol in sample without inhibitor})/[(\text{cpm estrone in sample without inhibitor}) + (\text{cpm estradiol in sample without inhibitor})]\}}.$$

Percent inhibition was calculated flowingly: % inhibition=100–% conversion

The values % inhibition were determined for exemplified compounds and the results are summarized in Table 2.

Inhibition of the 17β-Hydroxysteroid Dehydrogenase Type 2 Enzyme

17β-HSD2 Production and Isolation:

Similarly to 17β-HSD1 the Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested and supernatant were fractionated by the following protocol:

cells were dissolved into 40 ml of A-buffer (40 mM TRIS, pH8.0, 20% glycerol, 20 µM NAD, 0.4 mM PMSF, 150 mM NaCl, 0.5% dodecyl-β-maltoside+protease inhibitor cocktail)
cells were sonicated
lysate was incubated on ice for 15 min
lysate was centrifuged 5000 rpm 15 min, +4° C.
centrifugation of the supernatant 180.000 g 30 min, +4° C.
pellet was dissolved into 8 ml of A-buffer
not resuspended material was removed by centrifugation 5000 rpm 15 min, +4° C.
the clear supernatant was divided into 100 µl aliquots and were stored frozen until determination of enzymatic activity.

The amount of 17β-HSD2 was analysed by immunoblotting and total protein concentration of each extract batch was determined.

Assay—Inhibition of Recombinant Human 17β-HSD2:

Recombinant protein (4 µg/ml) was incubated in 20 mM KH2PO4 pH 8.5 with 50 nM estradiol (including 800.000 cpm/ml of $^3$H-estradiol) and 1 mM NADH for 30 min at RT, in the presence of the potential inhibitor at concentrations 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estradiol to estrone was calculated according to the following formula:

$$\% \text{ conversion} = 100 \times \frac{\{(\text{cpm estrone in sample with inhibitor})/[(\text{cpm estradiol in sample with inhibitor}) + (\text{cpm estrone in sample with inhibitor})]\}}{[(\text{cpm estrone in sample without inhibitor})/[(\text{cpm estradiol in sample without inhibitor}) + (\text{cpm estrone in sample without inhibitor})]\}}$$

Percent inhibition was calculated flowingly: % inhibition=100−% conversion

The values % inhibition were determined for exemplified compounds and the results are summarized in Table 2.

Estrogen Receptor Binding Assay

The binding affinity of the compounds of the invention to the estrogen receptor a (ERα) may be determined according to the in vitro ER binding assay described by Koffmann et al REF. Alternatively, an estrogen receptor binding assay may be performed according to international patent application WO2000/07996.

Estrogen Receptor Transactivation Assays

Compound of the invention showing binding affinity towards the estrogen receptor may be further tested with regard to their individual estrogenic or anti-estrogenic potential (Agonistic or antagonistic binding to the ERα or ERβ). The determination of the estrogen receptor antagonistic activity may be performed according to an in vitro assay system using the MMTV-ERE-LUC reporter system for example described in US patent application US2003/0170292.

Metabolic Stability Assay

The in vitro metabolic stability of the compounds of the invention was determined for exemplified compounds using human liver microsome and homogenate incubations. The incubation time points used with or without appropriate cofactors were 0 min and 60 min. Samples were collected at both time points and substrates were detected using LC/PDA/TOF-MS. In vitro metabolic stability (% remaining after 60 min in human liver homogenate or microsomes) of the compounds were calculated and the results are summarized in Table 3.

Pharmacological Test Results

TABLE 2

| # | 17β-HDS1 Inhibition % at 1 µM | 17β-HSD2 Inhibition % at 1 µM |
|---|---|---|
| 1 | 98 | 48 |
| 6 | 58 | 3 |
| 17 | 79 | 4 |
| 19 | 93 | 6 |
| 21 | 76 | 6 |
| 22 | 71 | 1 |
| 23 | 82 | 3 |
| 24 | 51 | 4 |
| 28 | 91 | 15 |
| 29 | 67 | 3 |
| 30 | 52 | 7 |
| 36 | 64 | 3 |
| 43 | 97 | 1 |
| 44 | 94 | 2 |
| 46 | 84 | 1 |
| 60 | 74 | 0 |
| 67 | 74 | 30 |
| 71 | 49 | 10 |
| 72 | 50 | 0 |
| 73 | 86 | 11 |
| 74 | 80 | 2 |
| 75b | 77 | 13 |
| 76 | 85 | 4 |
| 77 | 84 | 1 |
| 78 | 88 | 2 |
| 79 | 75 | 17 |
| 80a | 70 | 1 |
| 80b | 61 | 2 |
| 81 | 71 | 2 |

TABLE 3

| # | In vitro metabolic stability, % remaining after 60 min |
|---|---|
| VII | 13 |
| 17 | 37 |
| 19 | 90 |
| 55 | 47 |

Utility of the Invention

Compounds of the invention show selective inhibitory potential of the 17β-HSD1 enzyme and little or no inhibitory activity to the 17β-HSD2 enzyme and therefor, and may be useful for the treatment of a steroid hormone dependent malign or benign disease or disorder, in particular for treatment and prevention of several estrogen dependent diseases and disorders. Further, compounds of the present invention may be useful for the treatment of diseases and disorders associated with increased levels of estradiol and which may be prevented, treated, and/or ameliorated by an inhibitor of 17β-HSD1 enzyme.

Examples of inflammatory diseases and conditions include, but are not limited to, breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts.

"Treatment or prevention" as used herein includes prophylaxis, or prevention of, as well as lowering the individual's risk of falling ill with the named disorder or condition, or alleviation, amelioration, elimination, or cure of the said disorder once it has been established.

Compounds of the present invention may be administered in an effective amount within the dosage range of about 0.1 μg/kg to about 300 mg/kg, preferably between 1.0 μg/kg to 10 mg/kg body weight. Compounds of the present invention may be administered in a single daily dose, or the total daily dosage may be administered in divided doses of two, three or four times daily.

"An effective amount" refers to an amount of a compound that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

Compounds of the invention are most preferably used alone or in combination i.e. administered simultaneously, separately or sequentially with other active ingredients. Compounds of the invention may be administered by various routes, for example, parenteral, subcutaneous, intravenous, intraarticular, intrathecal, intramuscular, intraperitoneal, and by intradermal injections, and via transdermal, rectal, buccal, oromucosal, nasal, ocular routes and via inhalation and via implant.

Compounds may be formulated into a suitable composition; suitable administration forms include, for example, solutions, dispersions, suspensions, powders, capsules, tablet, pills, controlled release capsules, controlled release tablets and controlled release pills. In addition to the pharmacologically active compounds, the pharmaceutical compositions of the compounds can contain suitable pharmaceutically acceptable carriers comprising excipients and auxiliaries that facilitate processing of the active compounds into preparations that can be used pharmaceutically.

Furthermore, compounds of formula (I) can be used as synthesis intermediates for the preparation of other compounds, in particular of other pharmaceutically active ingredients, which are obtainable from compounds of formula (I), for example by introduction of substituents or modification of functional groups.

It will be obvious to a person skilled in the art that, as the technology advances, the inventive concept can be implemented in various ways. The invention and its embodiments are not limited to the examples described above but may vary within the scope of the claims.

The invention claimed is:
1. A compound of formula (I)

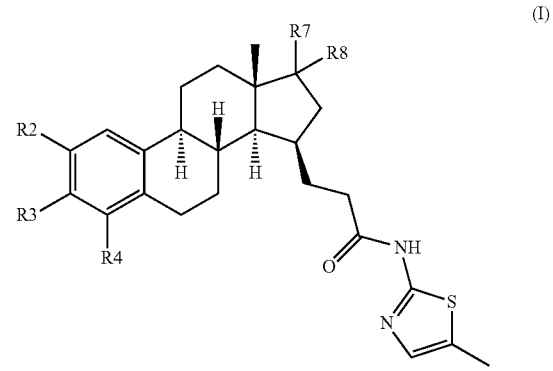

wherein
(i-a) R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_n$ $N(R)_2$, OR', $(CH_2)_n$OR', $CO_2R'$, CONHR', NHCOR", SCOR', or COR", and
R3 is selected from the group consisting of H, $C_{1-6}$-alkyl, $C_{1-3}$-haloalkyl, $C_{1-3}$-perhaloalkyl, $N(R')_2$, $N_3$, and $OR_3'$, wherein R3' is selected from the group consisting of R', benzyl, succinyl, optionally acylated glucuronyl, saturated 5 to 6 membered heterocyclic ring comprising 1 or 2 heteroatoms independently selected from N and O, $(CH_2)_n$OH, $SO_2OH$, $SO_2R"$, tosyl, $SO_2N(R')_2$, $PO(OR')_2$, $C(O)N(R')_2$, $C(O)(CH_2)_nN(R)_2$, and $C(O)R"'$; or
(i-b) R2 and R3 or R3 and R4, together with the ring carbon atoms to which they are attached, form an unsaturated or aromatic 5-membered heterocyclic ring comprising 1 or 2 heteroatoms each independently selected from N and O, optionally substituted with methyl or oxo; and
R4 or R2, respectively, is H and;
(ii-a) one of R7 and R8 is OR7', wherein R7' is selected from the group consisting of H or $C_{1-6}$-alkyl
and the other is selected from the group consisting of H, $C_{1-6}$-alkyl, $C_{1-3}$-haloalkyl, $C_{1-3}$-perhaloalkyl, $C_{2-6}$-alkenyl, $C_{2-6}$-alkynyl, benzyl, $(CH_2)_n$CN, $(CH_2)_n$OH, $N(R')_2$, $(CH_2)_nN(R')_2$, C(O)OR', $(CH_2)_nC(O)OR'$, $C(O)N(R')_2$, $(CH_2)_nC(O)NH_2$, OR7', COR', NHCO—$C_{1-6}$-alkyl, —$COCH_2O$—$P(O)(OH)_2$; or
(ii-b) one of R7 and R8 is H and the other is selected from the group consisting of halogen, $C_{1-3}$-haloalkyl, $C_{1-3}$-perhaloalkyl, $(CH_2)_n$CN, $OSO_2OH$, $OSO_2R"$, O-tosyl, $OC(O)R"'$, $OC(O)(CH_2)_n$COOR', $OC(O)(CH_2)_nN(R)_2$, $OC(O)CH_2NHC(O)OR'$, $OPO(OR')_2$, $N_3$, $N(R')_2$, $NH(CH_2)_mOR'$, $NH(CH_2)_mSR'$, $NH(CH_2)_mNR'_2$, NHOR', and NHC(O)R'; or
(ii-c) R7 and R8 form together a group selected from the group consisting of =$CH_2$, =CHR8', and CHCOOR7', wherein R8' is $C_{1-6}$-alkyl, $C_{1-6}$-alkoxy, or phenyl;
R' is H or $C_{1-6}$-alkyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O,
R" is $C_{1-6}$-alkyl, $C_{1-3}$-haloalkyl, or $C_{1-3}$-perhaloalkyl, R''' is C1-18-alkyl, C2-18-alkenyl, —(CH$_2$)$_n$—C$_{3-6}$-cycloalkyl, or optionally substituted phenyl, and n is 0, 1 or 2;

m is 1, 2 or 3;

or a pharmaceutically acceptable salt thereof.

2. A compound as claimed in claim 1, having the formula (Ia)

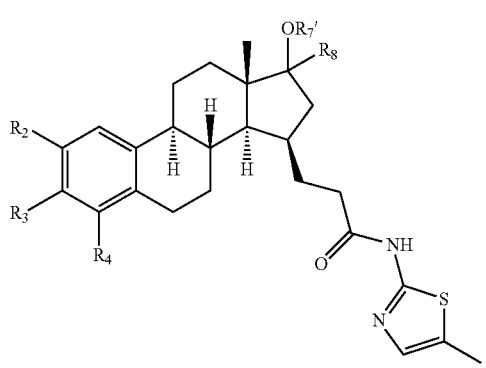

wherein R2 to R4 and R8 are as claimed in claim 1.

3. A compound as claimed in claim 1, having the formula (Ib)

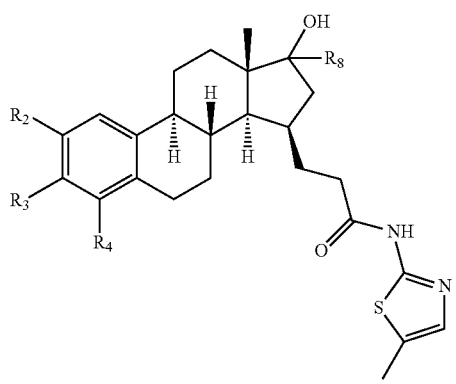

wherein R2 to R4 and R8 are as claimed in claim 1.

4. A compound as claimed in claim 2, wherein R8 is selected from the group consisting of C$_{1-6}$-alkyl, C$_{1-3}$-haloalkyl, C$_{1-3}$-perhaloalkyl, (CH$_2$)$_n$CN, (CH$_2$)$_n$OH, (CH$_2$)$_n$N(R')$_2$, (CH$_2$)$_n$C(O)OR', C(O)N(R')$_2$, and (CH$_2$)$_n$C(O)NH$_2$.

5. A compound as claimed in claim 3, wherein R8 is selected from the group consisting of C$_{1-6}$-alkyl, C$_{1-3}$-haloalkyl, C$_{1-3}$-perhaloalkyl, (CH$_2$)$_n$CN, (CH$_2$)$_n$OH, (CH$_2$)$_n$N(R)$_2$, (CH$_2$)$_n$C(O)OR', C(O)N(R')$_2$, and (CH$_2$)$_n$C(O)NH$_2$.

6. A compound of formula (I) or a pharmaceutically acceptable salt thereof as claimed in claim 1, having formula (Ic)

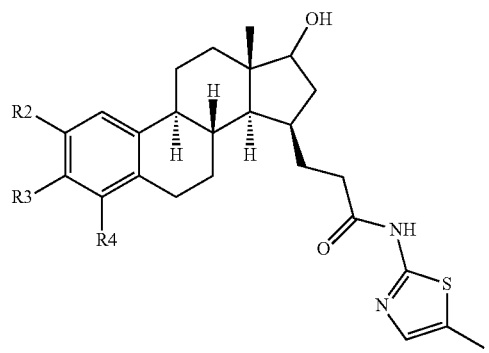

wherein R2 to R4 are as defined in claim 1.

7. A compound as claimed in claim 1, wherein R2 and R4 are each independently selected from the group consisting of H, halogen, C$_{1-6}$-alkyl, C$_{1-3}$-haloalkyl, C$_{1-3}$-perhaloalkyl, CN, NO$_2$, N$_3$, N(R')$_2$, (CH$_2$)$_n$N(R)$_2$, OR', (CH$_2$)$_n$OR', CO$_2$R', CONHR', COR'', NHCOR'', SCOR', or COR'''; and R3 is selected from the group consisting of H, halogen, C$_{1-6}$-alkyl, C$_{1-3}$-haloalkyl, C$_{1-3}$-perhaloalkyl, N(R')$_2$, (CH$_2$)$_n$NH$_2$, (CH$_2$)$_n$OR', N$_3$, and OR$_3$', wherein R3' is selected from the group consisting of R', benzyl, succinyl, optionally acylated glucuronyl, saturated 5 to 6 membered heterocyclic ring comprising 1 or 2 heteroatoms independently selected from N and O, (CH$_2$)$_n$OH, SO$_2$OH, SO$_2$R'', tosyl, SO$_2$N(R')$_2$, PO(OR')$_2$, C(O)N(R')$_2$, C(O)(CH$_2$)$_n$N(R)$_2$, and C(O)R'''.

8. A compound as claimed in claim 1, wherein R2 and R4 are each independently H or halogen.

9. A compound as claimed in claim 1, wherein R3 is selected from the group consisting of H, OH, C$_{1-6}$-alkoxy, and acyloxy.

10. A compound as claimed in claim 1, having formula (Ie)

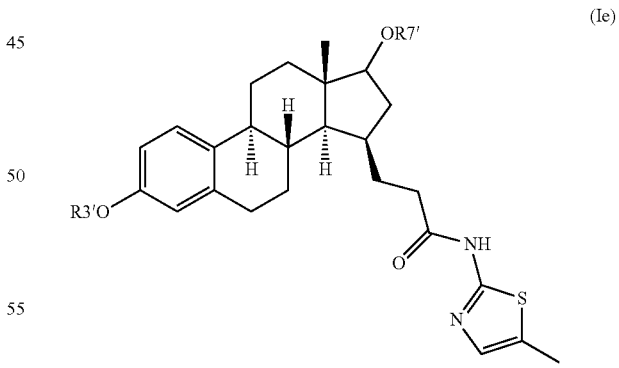

wherein R3' and R7' are as defined in claim 1.

11. A compound as claimed in claim 10, wherein one of R3' and R7' is H and the other one is selected from the group consisting of SO$_2$OH, SO$_2$R'', tosyl, SO$_2$N(R')$_2$, PO(OR')$_2$, C(O)N(R')$_2$, C(O)(CH$_2$)$_n$N(R)$_2$, and C(O)R''', or both R3' and R7' are independently selected from the group consisting of SO$_2$OH, SO$_2$R'', tosyl, SO$_2$N(R')$_2$, PO(OR')$_2$, C(O)N(R')$_2$, C(O)(CH$_2$)$_n$N(R)$_2$, and C(O)R'''.

12. A compound as claimed in claim 1, having formula (If)

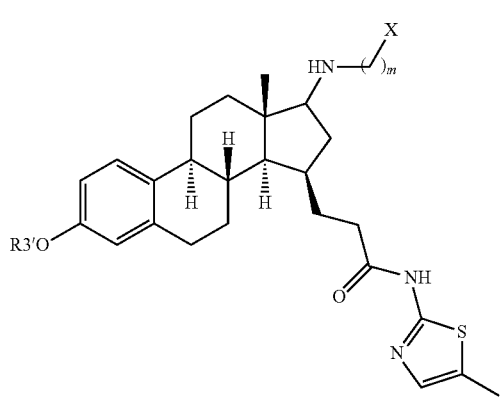

(If)

wherein m is 1, 2 or 3, X is OR', SR', NR'$_2$, and R' is H or C$_{1-6}$-alkyl, C$_{1-3}$-haloalkyl, or C$_{1-3}$-perhaloalkyl, or when part of any N(R')$_2$ both R's together with the nitrogen they are attached to may form an 5 to 6 membered aliphatic or aromatic heterocyclic ring comprising 1 or 2 heteroatoms each independently selected from N and O.

13. A compound as claimed in claim 12, wherein R' is selected from H and C$_{1-3}$-alkyl.

14. A compound of formula (I) as claimed in claim 1, selected from the group consisting of:
Compound 1 3-((13S,15R,17S)-3,17-Dihydroxy-13-methyl-7,8,9,11,12,13,14,15,16,17decahydro-6H-cyclopenta[a]phenanthren-15-yl)-N-(5-methylthiazol-2-yl)propanamide;
Compound 3 Acetic acid (13S,15R,17S)-17-hydroxyl-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;
Compound 6 3-((13S,15R,17S)-17-Hydroxy-3-methoxy-13-methyl-7,8,9, 11,12, 13, 14, 15, 16,17-decahydro-6H-cyclopenta[a]phenanthren-15-yl)-N-(5-methylthiazol-2-yl)propanamide;
Compound 8 3-((13S,15R,17S)-17-Hydroxy-3-methoxy-13-methyl-7,8,9,11,12,13,14,15,16,17-decahydro-6H-cyclopenta[a]phenanthren-15-yl)-propionic acid methyl ester;
Compound 9 3-((13S,15R,17S)-3,17-Dimethoxy-13-methyl-7,8,9,11,12,13,14,15,16,17-decahydro-6H-cyclopenta[a]phenanthren-15-yl)-propionic acid methyl ester;
Compound 10 3-((13S,15R,17S)-3,17-Dimethoxy-13-methyl-7,8,9,11,12,13,14,15,16,17-decahydro-6H-cyclopenta[a]phenanthren-15-yl)-propionic acid;
Compound 11 3-((13S,15R,17S)-3,17-Dimethoxy-13-methyl-7,8,9,11,12,13,14,15,16,17-decahydro-6H-cyclopenta[a]phenanthren-15-yl)-N-(5-methylthiazol-2-yl)propanamide;
Compound 13 Methyl 3-((13S,15R,17S)-3-(benzyloxy)-17-hydroxy-13-methyl-7,8,9,11,12,13,14,15,16,17-decahydro-6H-cyclopenta[a]phenanthren-15-yl)propanoate;
Compound 14 Methyl 3-((13S,15R,17S)-3-(benzyloxy)-17-methoxy-13-methyl-7,8,9,11,12,13,14,15,16,17-decahydro-6H-cyclopenta[a]phenanthren-15-yl)propanoate;
Compound 15 3-((13S,15R,17S)-3-(benzyloxy)-17-methoxy-13-methyl-7,8,9,11,12,13,14,15,16,17-decahydro-6H-cyclopenta[a]phenanthren-15-yl)propanoic acid;
Compound 16 3-((13S,15R,17S)-3-hydroxy-17-methoxy-13-methyl-7,8,9,11,12,13,14,15,16,17-decahydro-6H-cyclopenta[a]phenanthren-15-yl)propanoic acid;
Compound 17 3-((13S,15R,17S)-3-hydroxy-17-methoxy-13-methyl-7, 8,9, 11,12, 13, 14, 15, 16, 17-decahydro-6H-cyclopenta[a]phenanthren-15-yl)-N-(5-methylthiazol-2-yl)propanamide;
Compound 18 (13S,15R,17S)-17-methoxy-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate;
Compound 19 3-((13S,15R,17S)-17-butyl-3, 17-dihydroxy-13-methyl-7,8,9,11,12,13,14,15,16,17-decahydro-6H-cyclopenta[a]phenanthren-15-yl)-N-(5-methylthiazol-2-yl)propanamide;
Compound 20 3-((13S,15R,17S)-17-butyl-17-hydroxy-3-methoxy-13-methyl-7,8,9,11,12,13,14,15,16,17-decahydro-6H-cyclopenta[a]phenanthren-15-yl)-N-(5-methylthiazol-2-yl)propanamide;
Compound 21 3-((13S,15R,17S)-17-cyano-3,17-dihydroxy-13-methyl-7,8,9,11,12,13,14,15,16,17-decahydro-6H-cyclopenta[a]phenanthren-15-yl)-N-(5-methylthiazol-2-yl)propanamide;
Compound 22 (13S,15R,17S)-17-cyano-17-hydroxy-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate;
Compound 23 3-((13S,15R,17S)-17-cyano-17-hydroxy-3-methoxy-13-methyl-7,8,9,11,12,13,14,15,16,17-decahydro-6H-cyclopenta[a]phenanthren-15-yl)-N-(5-methylthiazol-2-yl)propanamide;
Compound 24 3-((13S,15R,17R)-17-(cyanomethyl)-3,17-dihydroxy-13-methyl-7,8,9,11,12,13,14,15,16,17-decahydro-6H-cyclopenta[a]phenanthren-15-yl)-N-(5-methylthiazol-2-yl)propanamide;
Compound 25 3-((13S,15R,17R)-17-(cyanomethyl)-17-hydroxy-3-methoxy-13-methyl-7,8,9,11,12,13,14,15,16,17-decahydro-6H-cyclopenta[a]phenanthren-15-yl)-N-(5-methylthiazol-2-yl)propanamide;
Compound 26 3-((13S,15R,17R)-17-(2-amino-2-oxoethyl)-3,17-dihydroxy-13-methyl-7,8,9,11,12,13,14,15,16,17-decahydro-6H-cyclopenta[a]phenanthren-15-yl)-N-(5-methylthiazol-2-yl)propanamide;
Compound 28 3-((13S,15R,17S)-2,4-dibromo-3,17-dihydroxy-13-methyl-7,8,9,11,12,13,14,15,16,17-decahydro-6H-cyclopenta[a]phenanthren-15-yl)-N-(5-methylthiazol-2-yl)propanamide;
Compound 29 3-((13S,15R,17S)-2,4-dibromo-3-hydroxy-17-methoxy-13-methyl-7,8,9,11,12,13,14,15,16,17-decahydro-6H-cyclopenta[a]phenanthren-15-yl)-N-(5-methylthiazol-2-yl)propanamide;
Compound 30 3-((13S,15R,17R)-2,4-dibromo-17-(cyanomethyl)-3,17-dihydroxy-13-methyl-7,8,9,11,12,13,14,15,16,17-decahydro-6H-cyclopenta[a]phenanthren-15-yl)-N-(5-methylthiazol-2-yl)propanamide;
Compound 31 3-((13S,15R,17S)-2,4-dibromo-17-butyl-3,17-dihydroxy-13-methyl-7,8,9,11,12,13,14,15,16,17-decahydro-6H-cyclopenta[a]phenanthren-15-yl)-N-(5-methylthiazol-2-yl)propanamide;
Compound 33 3-((13S,15R,17S)-17-hydroxy-13-methyl-3-((tetrahydro-2H-pyran-2-yl)oxy)-7,8,9,11,12,13,14,15,16,17-decahydro-6H-cyclopenta[a]phenanthren-15-yl)-N-(5-methylthiazol-2-yl)propanamide;

Compound 35 3-((13S,15R,17S)-3-(benzyloxy)-17-hydroxy-13-methyl-7,8,9,11,12,13,14,15,16,17-decahydro-6H-cyclopenta[a]phenanthren-15-yl)-N-(5-methylthiazol-2-yl)propanamide;

Compound 36 Acetic acid (13S,15R,17S)-3-hydroxy-13-methyl-15-[2-(5-methyl-thiazol-2-ylcarbamoyl)-ethyl]-17-oxo-7,8,9,11,12,13,14,15,16,17-decahydro-6H-cyclopenta[a]phenanthren-17-yl ester;

Compound 37 (13S,15R,17S)-3-(benzyloxy)-13-methyl-15-(3-((5-methylthiazol-2-yl)amino)-3-oxopropyl)-7,8,9,11,12,13,14,15,16,17-decahydro-6H-cyclopenta[a]phenanthren-17-yl pentanoate;

Compound 38 Pentanoic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 39 3-Cyclopentyl-propionic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 40 Dodecanoic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 41 Dodecanoic acid (13S,15R,17S)-17-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 42 Undec-10-enoic acid (13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 43 Succinic acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester;

Compound 44 Succinic acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester sodium salt;

Compound 45 Acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 46 Phosphoric acid mono-{(13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester;

Compound 47 Phosphoric acid mono-{(13S,15R,17S)-3-methoxy-13-methyl-15-[2-(5-methyl-thiazol-2-ylcarbamoyl)-ethyl]-17-oxo-7,8,9,11,12,13,14,15,16,17-decahydro-6H-cyclopenta[a]phenanthren-17-yl}ester disodium salt;

Compound 48 tert-Butoxycarbonylamino-acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 49 Amino-acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 50 Dimethylamino-acetic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 51 Methanesulphonic acid (13S,15R,17S)-3-methoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 52 Acetic acid (13S,15R,17S)-17-acetoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 53 Pentanoic acid (13S,15R,17S)-13-methyl-15-[2-(5-methylthiazol-2-ylcarbamoyl)-ethyl]-3-pentanoyloxy-7,8,9,11,12,13,14,15,16,17-decahydro-6H-cyclopenta[a]phenanthren-17-yl ester;

Compound 54 Dodecanoic acid (13S,15R,17S)-3-dodecanoyloxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl ester;

Compound 55 Benzoic acid (13S,15R,17S)-17-acetoxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 56 Undec-10-enoic acid (13S,15R,17S)-13-methyl-15-[2-(5-methylthiazol-2-ylcarbamoyl)-ethyl]-3-undec-10-enoyloxy-7,8,9,11,12,13,14,15,16,17-decahydro-6H-cyclopenta[a]phenanthren-17-yl ester;

Compound 57 Phosphoric acid mono-{(13S,15R,17S)-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester;

Compound 58 Phosphoric acid mono-{(13S,15R,17S)-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester tetrasodium salt;

Compound 59 Acetic acid (13S,15R,17S)-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester;

Compound 60 Phosphoric acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester;

Compound 61 Phosphoric acid mono-{(13S,15R,17S)-3-hydroxy-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-17-yl}ester trisodium salt;

Compound 62 3-Cyclopentyl-propionic acid (13S,15R)-3-acetoxy-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-17-yl ester;

Compound 63 p-Tosylsulphonic acid (13S,15R,17S)-13-methyl-15-[2-(5-methylthiazol-2-ylcarbamoyl)-ethyl]-17-p-tosylsulphonyloxy-7,8,9,11,12,13,14,15,16,17-decahydro-6H-cyclopenta[a]phenanthren-3-yl ester;

Compound 64 Methanesulphonic acid (13S,15R,17S)-17-methanesulphonyloxy-13-methyl-15-[2-(5-methylthiazol-2-ylcarbamoyl)-ethyl]-17-phosphonooxy-7,8,9,11,12,13,14,15,16,17-decahydro-6H-cyclopenta[a]phenanthren-3-yl ester;

Compound 67 3-((13S,15R)-17-Hydroxy13-methyl-7,8,9,11,12,13,14,15,16,17-decahydro-6H-cyclopenta[a]phenanthren-15-yl)-N-(5-methylthiazol-2-yl)propanamide; and Compound 68 3-{(13S,15R)-17-Formylamino-3-hydroxy-13-methyl-7,8,9,11,12,13,14,15,16,17-decahydro-6H-cyclopenta[a]phenanthren-15-yl}-N-(5-methylthiazol-2-yl)propanamide;

Compound 71 3-((13S,15R,17S)-3,17-Dihydroxy-4-isopropylamino-13-methyl-7,8,9,11,12,13,14,15,16,17-decahydro-6H-cyclopenta[a]phenanthren-15-yl)-N-(5-methylthiazol-2-yl)propionamide;

Compound 72 3-[(13S,15R,17S)-3,17-Dihydroxy-4-(2-hydroxy-1-methyl-ethylamino)-13-methyl-7,8,9,11,12,13,14,15,16,17-decahydro-6H-cyclopenta[a]phenanthren-15-yl]-N-(5-methylthiazol-2-yl)propionamide;

Compound 73 3-[(13S,15R)-3-Hydroxy-17-isopropylamino-13-methyl-7,8,9,11,12,13,14,15,16,17-decahydro-6H-cyclopenta[a]phenanthren-15-yl]-N-(5-methylthiazol-2-yl)propionamide;

Compound 74 34-(13S,15R)-3-Hydroxy-17-isobutylamino-13-methyl-7,8,9, 11,12, 13, 14,15, 16,17-decahydro-6H-cyclopenta[a]phenanthren-15-yl]-N-(5-methylthiazol-2-yl)propionamide;

Compound 75b 34-(13S,15R)-2-tert-Butyl-3-Hydroxy-17-isobutylamino-13-methyl-7,8,9, 11,12, 13, 14,15, 16,17-decahydro-6H-cyclopenta[a]phenanthren-15-yl]-N-(5-methylthiazol-2-yl)propionamide;

Compound 76 3-((13S,15R)-17-[(Furan-2-ylmethyl)-amino]-3-hydroxy-13-methyl-7,8,9, 11,12, 13, 14,15, 16,17-decahydro-6H-cyclopenta[a]phenanthren-15-yl]-N-(5-methylthiazol-2-yl)propionamide;

Compound 77 34-(13S,15R)-3-Hydroxy-17-(2-methoxyethylamino)-13-methyl-7,8,9,11,12,13,14,15,16,17-decahydro-6H-cyclopenta[a]phenanthren-15-yl]-N-(5-methylthiazol-2-yl)propionamide;

Compound 78 34-(13S,15R)-3-Hydroxy-17-(2-hydroxyethylamino)-13-methyl-7,8,9,11,12,13,14,15,16,17-decahydro-6H-cyclopenta[a]phenanthren-15-yl]-N-(5-methylthiazol-2-yl)propionamide;

Compound 79 3-((13S,15R)-2-tert-Butyl-3-hydroxy-17-(2-methoxyethylamino)-13-methyl-7,8,9,11,12,13,14,15,16,17-decahydro-6H-cyclopenta[a]phenanthren-15-yl)-N-(5-methylthiazol-2-yl)propionamide;

Compound 80a 3-[(13S,15R)-17-(3-Dimethylamino-propylamino)-3-hydroxy-13-methyl-7,8,9,11,12,13,14,15,16,17-decahydro-6H-cyclopenta[a]phenanthren-15-yl]-N-(5-methylthiazol-2-yl)propionamide;

Compound 80b 3-[(13S,15R)-17-(3-Dimethylamino-propylamino)-3-hydroxy-13-methyl-7,8,9,11,12,13,14,15,16,17-decahydro-6H-cyclopenta[a]phenanthren-15-yl]-N-(5-methylthiazol-2-yl)propionamide dihydrochloride;

Compound 81 3-[(13S,15R)-17-(2-Dimethylamino-ethylamino)-3-hydroxy-13-methyl-7,8,9,11,12,13,14,15,16,17-decahydro-6H-cyclopenta[a]phenanthren-15-yl]-N-(5-methylthiazol-2-yl)propionamide;

or a pharmaceutically acceptable salt thereof.

15. A pharmaceutical composition comprising an effective amount of one or more compounds as claimed in claim 1, together with one or more pharmaceutically acceptable excipient(s).

16. The pharmaceutical composition as claimed in claim 15 comprising one or more other active ingredients.

17. A method of treating a steroid hormone dependent malign or benign disease or disorder, comprising administering a compound as claimed in claim 1 to a patient in need thereof.

18. The method of treating a steroid hormone dependent malign or benign disease or disorder as claimed in claim 17, wherein the said disease or disorder is selected from the group consisting of breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts.

19. The method of treating a steroid hormone dependent malign or benign disease or disorder as claimed in claim 17, wherein the said disease or disorder is an estradiol dependent disease or disorder.

20. A method of treating of disease or disorder requiring the inhibition of 17β-HSD enzyme comprising administering a compound as claimed in claim 1 to a patient in need thereof.

* * * * *